US012622613B2

(12) United States Patent
Wang et al.

(10) Patent No.: US 12,622,613 B2
(45) Date of Patent: May 12, 2026

(54) REMOTE MONITORING OF OXYGENATION STATUS AND BLOOD PULSATION WITHIN SKIN TISSUE

(71) Applicant: University of Washington, Seattle, WA (US)

(72) Inventors: Ruikang K. Wang, Seattle, WA (US); Qinghau He, Seattle, WA (US)

(73) Assignee: University of Washington, Seattle, WA (US)

( * ) Notice: Subject to any disclaimer, the term of this patent is extended or adjusted under 35 U.S.C. 154(b) by 333 days.

(21) Appl. No.: 18/547,198

(22) PCT Filed: Feb. 25, 2022

(86) PCT No.: PCT/US2022/017848
§ 371 (c)(1),
(2) Date: Aug. 21, 2023

(87) PCT Pub. No.: WO2022/182956
PCT Pub. Date: Sep. 1, 2022

(65) Prior Publication Data
US 2024/0148289 A1 May 9, 2024

Related U.S. Application Data

(60) Provisional application No. 63/154,100, filed on Feb. 26, 2021.

(51) Int. Cl.
*A61B 5/1455* (2006.01)
*A61B 5/00* (2006.01)
(Continued)

(52) U.S. Cl.
CPC ...... *A61B 5/14551* (2013.01); *A61B 5/02427* (2013.01); *A61B 5/6898* (2013.01);
(Continued)

(58) Field of Classification Search
CPC . A61B 5/0059; A61B 5/1455; A61B 5/14551; A61B 5/7225; A61B 5/742
See application file for complete search history.

(56) References Cited

U.S. PATENT DOCUMENTS 5,502,799 A 3/1996 Tsuji
8,335,550 B2 * 12/2012 Segman ............... A61B 5/1455
600/310
(Continued)

FOREIGN PATENT DOCUMENTS

WO 9013091 A1 11/1990
WO 9837811 A1 9/1998
(Continued)

OTHER PUBLICATIONS

D. Castaneda, A. Esparza, M. Ghamari, C. Soltanpur, and H. Nazeran, "A review on wearable photoplethysmography sensors and their potential future applications in health care," International journal of biosensors & bioelectronics 4, 195 (2018).
(Continued)

*Primary Examiner* — Eric F Winakur
(74) *Attorney, Agent, or Firm* — CHRISTENSEN O'CONNOR JOHNSON KINDNESS PLLC

(57) ABSTRACT

A method of measuring blood oxygenation including acquiring one or more images of a portion of a body with an RGB camera, converting RGB colors in the one or more images into a multispectral data imaging cube, wherein the multispectral date imaging cube comprises a red channel, a blue channel, and a green channel, decoupling an oxygenated blood information and a deoxygenated blood information from the multispectral data imaging cube based on a first reflectance of the green channel and a second reflectance of
(Continued)

the red channel, and determining a blood measurement based on the oxygenated blood information and the deoxygenated blood information.

18 Claims, 28 Drawing Sheets

(51) Int. Cl.
| | |
|---|---|
| *A61B 5/024* | (2006.01) |
| *G06T 7/00* | (2017.01) |
| *G06T 7/70* | (2017.01) |
| *G06T 7/90* | (2017.01) |

(52) U.S. Cl.
CPC ............ *A61B 5/7225* (2013.01); *A61B 5/742* (2013.01); *G06T 7/0012* (2013.01); *G06T 7/70* (2017.01); *G06T 7/90* (2017.01); *G06T 2207/10016* (2013.01); *G06T 2207/10024* (2013.01); *G06T 2207/30088* (2013.01)

(56) References Cited

U.S. PATENT DOCUMENTS

| | | | |
|---|---|---|---|
| 9,474,506 | B2 | 10/2016 | Magnin |
| 2008/0146918 | A1 | 6/2008 | Magnin |
| 2008/0278592 | A1 | 11/2008 | Kuno |
| 2009/0018422 | A1 | 1/2009 | Banet |
| 2013/0051827 | A1 | 2/2013 | Fukumuro |
| 2013/0289941 | A1 | 10/2013 | Keydar |
| 2014/0118736 | A1 | 5/2014 | Norris |
| 2014/0195189 | A1 | 7/2014 | Norris |
| 2016/0166150 | A1 | 6/2016 | Vilenskii |
| 2017/0347886 | A1 | 12/2017 | Tran |
| 2018/0255280 | A1 | 9/2018 | Gutierrez |
| 2019/0200941 | A1 | 7/2019 | Chandran |
| 2019/0274619 | A1 | 9/2019 | Gareau |
| 2019/0320875 | A1 | 10/2019 | Jones |
| 2021/0201479 | A1 | 7/2021 | Fan |
| 2022/0240786 | A1 | 8/2022 | Subhash |
| 2022/0329767 | A1 | 10/2022 | Wang |

FOREIGN PATENT DOCUMENTS

| | | | |
|---|---|---|---|
| WO | 2011070357 | A1 | 6/2011 |
| WO | 2016152900 | A1 | 9/2016 |
| WO | 2017012675 | A1 | 1/2017 |
| WO | 2022003308 | | 1/2022 |

OTHER PUBLICATIONS

J. Liu, B. P.-Y. Yan, W.-X. Dai, X.-R. Ding, Y.-T. Zhang, and N. Zhao, "Multi-wavelength photoplethysmography method for skin arterial pulse extraction," Biomed. Opt. Express 7, 4313-4326 (2016).

A. A. R. Kamal, J. B. Harness, G. Irving, and A. J. Mearns, "Skin photoplethysmography a review," Computer methods and programs in biomedicine 28, 257-269 (1989).

D. Biswas, N. Simoes-Capela, C. Van Hoof, and N. Van Helleputte, "Heart rate estimation from wrist-worn photoplethysmography: A review," IEEE Sensors Journal 19, 6560-6570 (2019).

N. Paradkar and S. R. Chowdhury, "Cardiac arrhythmia detection using photoplethysmography," in IEEE, 113-116, (2017).

O. S. Hoilett, A. M. Twibell, R. Srivastava, and J. C. Linnes, "Kick LL: A smartwatch for monitoring respiration and heart rate using photoplethysmography," in (IEEE, 3821-3824, (2019).

M. van Gastel, S. Stuijk, and G. de Haan, "Robust respiration detection from remote photoplethysmography," Biomed. Opt. Express 7, 4941-4957 (2016).

V. V. Zaytsev, S. V. Miridonov, O. V. Mamontov, and A. A. Kamshilin, "Contactless monitoring of the blood-flow changes in upper limbs," Biomed. Opt. Express 9, 5387-5399 (2018).

W. Wang, A. C. den Brinker, and G. De Haan, "Full video pulse extraction," Biomed. Opt. Express 9, 3898-3914 (2018).

W. W. Muir and M. L. Wellman, "Hemoglobin solutions and tissue oxygenation," Journal of veterinary internal medicine 17, 127-135 (2003).

D. A. Low, H. Jones, N. T. Cable, L. M. Alexander, and W. L. Kenney, "Historical reviews of the assessment of human cardiovascular function: interrogation and understanding of the control of skin blood flow," European journal of applied physiology 120, 1-16 (2020).

M. Hellmann, M. Roustit, and J. L. Cracowski, "Skin microvascular endothelial function as a biomarker in cardiovascular diseases?," Pharmacological Reports 67, 803-810 (2015).

Q. He and R. Wang, "Hyperspectral imaging enabled by an unmodified smartphone for analyzing skin morphological features and monitoring hemodynamics," Biomed. Opt. Express 11, 895-910 (2020).

Q. He and R. K. Wang, "Analysis of skin morphological features and real-time monitoring using snapshot hyperspectral imaging," Biomed. Opt. Express 10, 5625-5638 (2019).

Q. He, Z. Sun, Y. Li, W. Wang, and R. K. Wang, "Smartphone-enabled snapshot multispectral autofluorescence imaging and its application for bacteria assessments in skin and oral cavity," Optics and Lasers in Engineering 140, 106546 (2021).

J. Eckhard, T. Eckhard, E. M. Valero, J. L. Nieves, and E. G. Contreras, "Outdoor scene reflectance measurements using a Bragg-grating-based hyperspectral imager," Applied Optics 54, D15-D24 (2015).

J. Hernandez-Andres, J. Romero, and R. L. Lee, "Colorimetric and spectroradiometric characteristics of narrow-field-of-view clear skylight in Granada, Spain," JOSA A 18, 412-420 (2001).

W. Karlen, J. Lim, J. M. Ansermino, G. Dumont, and C. Scheffer, "Design challenges for camera oximetry on a mobile phone," in 2012 Annual International Conference of the IEEE Engineering in Medicine and Biology Society, 2012, 2448-2451.

R. D. Muir, S. Z. Sullivan, R. A. Oglesbee, and G. J. Simpson, "Synchronous digitization for high dynamic range lock-in amplification in beam-scanning microscopy," Review of Scientific Instruments 85, 033703 (2014).

A. A. Kamshilin, S. Miridonov, V. Teplov, R. Saarenheimo, and E. Nippolainen, "Photoplethysmographic imaging of high spatial resolution," Biomed. Opt. Express 2, 996-1006 (2011).

K. Jackman and C. Iadecola, "Neurovascular regulation in the ischemic brain," Antioxidants & redox signaling 22, 149-160 (2015).

HH. Billett. "Hemoglobin and Hematocrit." in Clinical Methods: The History, Physical, and Laboratory Examinations. (Boston: Butterworths, 1990), Chap. 151.

P. Oltulu, B. Ince, N. Kokbudak, S. Findik, and F. Kilinc, "Measurement of epidermis, dermis, and total skin thicknesses from six different body regions with a new ethical histometric technique," Turkish Journal of Plastic Surgery 26, 56-61 (2018).

L. Wang, S. L. Jacques, and L. Zheng, "MCML—Monte Carlo modeling of light transport in multi-layered tissues," Computer methods and programs in biomedicine 47, 131-146 (1995).

R. K. Wang, "Signal degradation by multiple scattering in optical coherence tomography of dense tissue: a Monte Carlo study towards optical clearing of biotissues," Physics in Medicine & Biology 47, 2281 (2002).

S. L. Jacques, "Optical properties of biological tissues: a review," Physics in Medicine & Biology 58, R37 (2013).

J. Lee, M. Kim, H.-K. Park, and I. Y. Kim, "Motion Artifact Reduction in Wearable Photoplethysmography Based on Multi-Channel Sensors with Multiple Wavelengths," Sensors 20, 1493 (2020).

C.-C. Chang, C.-T. Wu, B. I. Choi, and T.-J. Fang, "MW-PPG sensor: An on-chip spectrometer approach," Sensors 19, 3698 (2019).

F. P. Wieringa, F. Mastik, and A. F. W. van der Steen, "Contactless multiple wavelength photoplethysmographic imaging: A first step toward "SpO 2 camera" technology," Annals of biomedical engineering 33, 1034-1041 (2005).

J. Zheng, S. Hu, V. Azorin-Peris, A. Echiadis, V. Chouliaras, and R. Summers, "Remote simultaneous dual wavelength imaging

(56)　　　　References Cited

OTHER PUBLICATIONS photoplethysmography: a further step towards 3-D mapping of skin blood microcirculation," in (International Society for Optics and Photonics, 68500S, (2008).

Janis Spigulis—non-patent publication, May 2017—Multispectral, Fluorescent and Photoplethysmographic Imaging for Remote Skin Assessment.

Zaunseder et al.—non-patent publication, Jun. 2018—Cardiovascular Assessment by Imaging Photoplethysmography.

Spigulis—non-patent publication, Aug. 2017—In vivo skin imaging prototypes "made in Latvia".

Pan & Shen—non-patent publication, Apr. 2019—Multispectral Image Super-Resolution via RGB Image Fusion and Radiometric Calibration.

T. B. Fitzpatrick, "Soleil et peau," J. de Medecine Esthetique 2, 33-34 (1975).

J. M. Bland and D. G. Altman, "Statistical methods for assessing agreement between two methods of clinical measurement," Lancet 327(8476), 307-310 (1986).

Michael W Browne, "Cross-Validation Methods," Journal of Mathematical Psychology 44 (1), 108-132 (2000).

Richard R. Picard and R. Dennis Cook, "Cross-Validation of Regression Models," Journal of the American Statistical Association 79 (387), 575-583(1984).

G. Zonios, J. Bykowski, and N. Kollias, "Skin melanin, hemoglobin, and light scattering roperties can be quantitatively assessed in vivo using diffuse reflectance spectroscopy," J. Invest. Dermatol. 117(6), 1452-1457 (2001).

S. Kwon, H. Kim and K. S. Park, "Validation of heart rate extraction using video imaging on a built-in camera system of a smartphone," Annual International Conference of the IEEE Engineering in Medicine and Biology Society, 2174-2177 (2012).

T.B. Plante, B. Urrea, Z.T. MacFarlane, R.S. Blumenthal, E.R. Miller, L.J. Appel and S.S. Martin, "Validation of the Instant Blood Pressure Smartphone App," JAMA Intern Med. 176(5):700-702 (2016).

J. W. Severinghaus, "Discovery of pulse oximetry," Anesth. Analg. 105(6), S1-S4 (2007).

Yoon, J. et al., "A clinically translatable hyperspectral endoscopy (HySE) system for imaging the gastrointestinal tract," Nature Commubications; (2019) 10:1902; https://doi.org/10.1038/s41467-019-09484-4; pp. 1-13.

He, et al., Hyperspectral imaging enabled by an unmodified smartphone for analyzing skin morphological features and monitoring hemodynamics, (Jan. 14, 2020), URL: https://opg.optica.org/boe/fulltext.cfm?uri=boe-11-2-895, (Apr. 13, 2022), XP055965074.

Jonghee Yoon, Joseph James, Waterhouse Dale J., Luthman A. Siri, Gordon George S. D., Di Pietro Massimiliano, Januszewicz Wladyslaw, Fitzgerald Rebecca C., Bohndiek Sarah E., "A clinically translatable hyperspectral endoscopy (HySE) system for imaging the gastrointestinal tract", Nature Communications, Nature Publishing Group, (Apr. 23, 2019), vol. 10, No. 1, doi: 10.1038/s41467-019-09484-4, XP055650821.

Hata, Ryuji, et al. "A reproducible model of middle cerebral artery occlusion in mice: hemodynamic, biochemical, and magnetic resonance imaging." Journal of Cerebral Blood Flow & Metabolism 18.4 (1998): 367-375.

Goel, Mayank, et al. "HyperCam: hyperspectral imaging for ubiquitous computing applications." UbiComp 2015.

International Preliminary Report on Patentability mailed Apr. 5, 2022, issued in the corresponding International Application No. PCT/US2020/053564, filed Sep. 30, 2020, 8 pages.

International Search Report and Written Opinion mailed Jan. 6, 2021, issued in the corresponding International Application No. PCT/US2020/053564, filed Sep. 30, 2020, 9 pages.

Achten, Juul, and Asker E. Jeukendrup. "Heart rate monitoring." Sports medicine 33.7 (2003): 517-538.

Basiri, Ali, et al. "Use of a multi-spectral camera in the characterization of skin wounds." Optics express 18.4 (2010): 3244-3257.

Benedetto, Simone, et al. "Assessment of the Fitbit Charge 2 for monitoring heart rate." PloS one 13.2 (2018): e0192691.

Hirohara, Y., et al. "Development of fundus camera for spectral imaging using liquid crystal tunable filter." Investigative Ophthalmology & Visual Science 45.13 (2004): 2418-2418.

Chen, Xinlin, et al. "In vivo real-time imaging of cutaneous hemoglobin concentration, oxygen saturation, scattering properties, melanin content, and epidermal thickness with visible spatially modulated light." Biomedical optics express 8.12 (2017): 5468-5482.

Cheong, Wai-Fung, Scott A. Prahl, and Ashley J. Welch. "A review of the optical properties of biological tissues." IEEE journal of quantum electronics 26.12 (1990): 2166-2185.

Clancy, Neil T., et al. "Intraoperative measurement of bowel oxygen saturation using a multispectral imaging laparoscope." Biomedical optics express 6.10 (2015): 4179-4190.

Diaz, Keith M., et al. "Fitbit®: An accurate and reliable device for wireless physical activity tracking." International journal of cardiology 185 (2015): 1-5.

Diebele, Ilze, et al. "Clinical evaluation of melanomas and common nevi by spectral imaging." Biomedical optics express 3.3 (2012): 467-472.

Dugel, Pravin U., and Cheryl N. Zimmer. "Imaging of melanin disruption in age-related macular degeneration using multispectral imaging." Ophthalmic Surgery, Lasers and Imaging Retina 47.2 (2016): 134-141.

Fujiwara, Masaru, et al. "Spectroscopic imaging of blood vessels only near the skin surface for non-invasive blood glucose measurement." Proc. SPIE 9537, Clinical and Biomedical Spectroscopy and Imaging IV, 953714 (Jul. 15, 2015).

Gao, Liang, R. Theodore Smith, and Tomasz S. Tkaczyk. "Snapshot hyperspectral retinal camera with the Image Mapping Spectrometer (IMS)." Biomedical optics express 3.1 (2012): 48-54.

Ghassemi, Pejhman, et al. "A polarized multispectral imaging system for quantitative assessment of hypertrophic scars." Biomedical optics express 5.10 (2014): 3337-3354.

Jackson, James E., Averil O. Mansfield, and David J. Allison. "Treatment of high-flow vascular malformations by venous embolization aided by flow occlusion techniques." Cardiovascular and interventional radiology 19.5 (1996): 323-328.

Jakovels, Dainis, and Janis Spigulis. "2-D mapping of skin chromophores in the spectral range 500-700 nm." Journal of biophotonics 3.3 (2010): 125-129.

Kainerstorfer, Jana M., et al. "Principal component model of multispectral data for near real-time skin chromophore mapping." Journal of Biomedical Optics 15.4 (2010): 046007.

Kapsokalyvas, Dimitrios, et al. "Spectral morphological analysis of skin lesions with a polarization multispectral dermoscope." Optics express 21.4 (2013): 4826-4840.

Kellett, S. C., and D. J. Gawkrodger. "The psychological and emotional impact of acne and the effect of treatment with isotretinoin." British journal of Dermatology 140.2 (1999): 273-282.

Kim, Bumju, et al. "In vivo visualization of skin inflammation by optical coherence tomography and two-photon microscopy." Biomedical Optics Express 6.7 (2015): 2512-2521.

Kim, Sewoong, et al. "Smartphone-based multispectral imaging: system development and potential for mobile skin diagnosis." Biomedical optics express 7.12 (2016): 5294-5307.

Kuzmina, Ilona, et al. "Towards noncontact skin melanoma selection by multispectral imaging analysis." Journal of Biomedical optics 16.6 (2011): 060502.

Manson, Paul N., et al. "Improved survival in free skin flap transfers in rats." Surgery 99.2 (1986): 211-215.

Matthews, Thomas E., et al. "In vivo and ex vivo epi-mode pump-probe imaging of melanin and microvasculature." Biomedical optics express 2.6 (2011): 1576-1583.

Tanaka, Kenichi, et al. "Skin autofluorescence is associated with renal function and cardiovascular diseases in pre-dialysis chronic kidney disease patients." Nephrology Dialysis Transplantation 26.1 (2011): 214-220.

Nkengne, A., et al. "SpectraCam: A new polarized hyperspectral imaging system for repeatable and reproducible in vivo skin quan-

(56) References Cited

OTHER PUBLICATIONS tification of melanin, total hemoglobin, and oxygen saturation." Skin Research and Technology 24.1 (2018): 99-107.

Pearson, Thomas C. "Hemorheologic considerations in the pathogenesis of vascular occlusive events in polycythemia vera." Seminars in thrombosis and hemostasis. vol. 23. No. 05. 1997.

Rehak, Jiri, and Matus Rehak. "Branch retinal vein occlusion: pathogenesis, visual prognosis, and treatment modalities." Current eye research 33.2 (2008): 111-131.

Penachini, M., et al. "Comparison of Polarfi RS800G3TM heart rate monitor with Polarfi S810iTM and electrocardiogram to obtain the series of RR intervals and analysis of heart rate variability at rest." Clin Physiol Funct Imaging (2016) 36, pp. 112-117.

Robles, Francisco E., Jesse W. Wilson, and Warren S. Warren. "Quantifying melanin spatial distribution using pump-probe microscopy and a 2-D morphological autocorrelation transformation for melanoma diagnosis." Journal of biomedical optics 18.12 (2013): 120502.

Rosen, Cheryl F., et al. "Immediate pigment darkening: visual and reflectance spectrophotometric analysis of action spectrum." Photochemistry and photobiology 51.5 (1990): 583-588.

Tseng, Sheng-Hao, et al. "Chromophore concentrations, absorption and scattering properties of human skin in-vivo." Optics express 17.17 (2009): 1-28.

Spigulis, Janis. "Multispectral, fluorescent and photoplethysmographic imaging for remote skin assessment." Sensors 17.5 (2017): 1165.

Spigulis, Janis, et al. "Smartphone snapshot mapping of skin chromophores under triple-wavelength laser illumination." Journal of Biomedical Optics 22.9 (2017): 091508.

Srivastava, Ruchir, et al. "Three-dimensional graph-based skin layer segmentation in optical coherence tomography images for roughness estimation." Biomedical Optics Express 9.8 (2018): 3590-3606.

Stamatas, Georgios N., and Nikiforos Kollias. "In vivo documentation of cutaneous inflammation using spectral imaging." Journal of Biomedical optics 12.5 (2007): 051603.

Tracy, C., et al. "Characterization of Renal Ischemia Using DLP Hyperspectral Imaging: A Pilot Study Comparing Artery-Only Occlusion Versus Artery and Vein Occlusion," Journal Of Endourology 24.3 (2010) 321-325.

Van Waateringe, Robert P., et al. "Skin autofluorescence predicts incident type 2 diabetes, cardiovascular disease and mortality in the general population." Diabetologia 62.2 (2019): 269-280.

Vasefi, Fartash, et al. "Polarization-sensitive hyperspectral imaging in vivo: a multimode dermoscope for skin analysis." Scientific reports 4.4924 (2014): 1-10.

Yaroslavsky, Anna N., Victor Neel, and R. Rox Anderson. "Demarcation of nonmelanoma skin cancer margins in thick excisions using multispectral polarized light imaging." Journal of investigative dermatology 121.2 (2003): 259-266.

Zhang, Rui-Lan, et al. "Temporal profile of ischemic tissue damage, neutrophil response, and vascular plugging following permanent and transient (2H) middle cerebral artery occlusion in the rat." Journal of the neurological sciences 125.1 (1994): 3-10.

Zonios, George, Julie Bykowski, and Nikiforos Kollias. "Skin melanin, hemoglobin, and light scattering properties can be quantitatively assessed in vivo using diffuse reflectance spectroscopy." Journal of Investigative Dermatology 117.6 (2001): 1452-1457.

Office Action (Non-Final Rejection) dated Jan. 4, 2024 for U.S. Appl. No. 17/765,317 (pp. 1-13).

Akhtar, N. and A. Mian, "Hyperspectral Recovery from RGB Images using Gaussian Processes," IEEE Transactions on Pattern Analysis and Machine Intelligence, vol. 42, No. 1, Jan. 2020.

Allen, J. "Photoplethysmography and its application in clinical physiological measurement," Physiol. Meas. 28 (2007) R1-R39; doi:10.1088/0967-3334/28/3/R01.

International Search Report and Written Opinion mailed Feb. 28, 2024, issued in corresponding International Application No. PCT/US2023/077963, filed Oct. 26, 2023, 9 pages.

Office Action (Final Rejection) dated Jul. 8, 2024 for U.S. Appl. No. 17/765,317 (pp. 1-14).

Office Action (Notice of Allowance and Fees Due (PTOL-85)) dated Oct. 30, 2024 for U.S. Appl. No. 17/765,317 (pp. 1-8).

Brunton, Steven L., et al. "Singular Value Decomposition (SVD)." Data-Driven Science and Engineering (Cambridge University Press, Cambridge, United Kingdom, 2019, 44 pages.

An, L. et al., "Ultrahigh sensitive optical microangiography for in vivo imaging of microcirculations within human skin tissue beds," Opt Express. Apr. 12, 2010; 18(8): 8220-8228.

Avci, MD, P. et al., "Low-level laser (light) therapy (LLLT) in skin: stimulating, healing, restoring," Semin Cutan Med Surg. Mar. 2013 ; 32(1): 41-52.

Baker, W. B. et al., "Modified Beer-Lambert law for blood flow," Biomedical Optics Express; Nov. 1, 2014; vol. 5, No. 11; DOI:10.1364/BOE.5.004053.

Bakermans, PhD, A. J. et al., "Dynamic Magnetic Resonance Measurements of Calf Muscle Oxygenation and Energy Metabolism in Peripheral Artery Disease," J. Magn. Reson. Imaging 2020;51:98-107.

Bal., U. "Non-contact estimation of heart rate and oxygen saturation using ambient light," Biomedical Optics Express; Jan. 1, 2015; vol. 6, No. 1; DOI:10.1364/BOE.6.000086; pp. 86-97.

Benaron, M.D., D. A. et al., "Continuous, Noninvasive, and Localized Microvascular Tissue Oximetry Using Visible Light Spectroscopy," Anesthesiology 2004; 100:1469-75.

C. A. Lewis, W. Fergusson, T. Eaton, I. Zeng, and J. Kolbe, "Isolated nocturnal desaturation in COPD: prevalence and impact on quality of life and sleep," Thorax 64(2), 133-138 (2009).

W. W. Flemons, D. Buysse, S. Redline, A. Oack, K. Strohl, J. Wheatley, T. Young, N. Douglas, P. Levy, W. McNicolas, J. Fleetham, D. White, W. Schmidt-Nowarra, D. Carley, and J. Romaniuk, "Sleep-related breathing disorders in adults: recommendations for syndrome definition and measurement techniques in clinical research. The Report of an American Academy of Sleep Medicine Task Force," Sleep 22(5), 667-689 (1999).

Thirumalaisamy P. Velavan, and Christian G. Meyer, "The COVID-19 epidemic," Tropical medicine & international health 25 (3), 278-280 (2020).

A. D. Pitkin, C. M. Roberts and J. A. Wedzicha, "Arterialised earlobe blood gas analysis: an underused technique," Thorax 49, 364-366(1994).

J. W. Severinghaus, P. Astrup, and J. F. Murray, "Blood Gas Analysis and Critical Care Medicine," American Journal of Respiratory and Critical Care Medicine 157(4), S114-S122 (1998).

J. W. Severinghaus and Y. Honda, "History of blood gas analysis. VII. Pulse oximetry," J. Clin. Monitor Comput. 3, 135-138 (1987).

Y. Sun, S. Hu, V. Azorin-Peris, R. Kalawsky, and S. Greenwald, "Noncontact imaging photoplethysmography to effectively access pulse rate variability," J. Biomed. Opt. 18(6), 061205 (2012).

L. Tarassenko, M. Villarroel, A. Guazzi, J. Jorge, D. A. Clifton, and C. Pugh, "Non-contact video-based vital sign monitoring using ambient light and auto-regressive models," Physiol. Meas. 35(5), 807-831 (2014).

D. Shao, Y. Yang, C. Liu, F. Tsow, H. Yu, and N. Tao, "Noncontact monitoring breathing pattern, exhalation flow rate and pulse transit time," IEEE Trans. Biomed. Eng. 61(11), 2760-2767 (2014).

A. Castillo, A. Sola, H. Baquero, F. Neira, R. Alvis, R. Deulofeut and A. Critz, "Pulse Oxygen Saturation Levels and Arterial Oxygen Tension Values in Newborns Receiving Oxygen Therapy in the Neonatal Intensive Care Unit: Is 85% to 93% an Acceptable Range?," Pediatrics 121(5), 882-889 (2008).

C. Guilleminault, S. J. Connolly and R. A. Winkle, "Cardiac arrhythmia and conduction disturbances during sleep in 400 patients with sleep apnea syndrome," The American Journal of Cardiology 52(5), 490-494(1983).

F. P. Wieringa, F. Mastik, and A. F. W. van der Steen, "Contactless Multiple Wavelength Photoplethysmographic Imaging: A First Step Toward "SpO2 Camera" Technology," Ann. Biomed. Eng. 33, 1034-1041 (2005).

K. Humphreys, T. Ward and C. Markham, "Noncontact simultaneous dual wavelength photoplethysmography: a further step toward noncontact pulse oximetry," Rev. Sci. Instrum. 78, 044304 (2007).

(56)         References Cited

OTHER PUBLICATIONS

L. Kong, Y. Zhao, Y. Dong, Y. Jian, X. Jin, B. Li, Y. Feng, M. Liu, X. Liu, and H. Wu, "Non-contact detection of oxygen saturation based on visible light imaging device using ambient light," Opt. Express 21(15), 1764-1771 (2013).

I. Nishidate, K. Sasaoka, T. Yuasa, J. Niizeki, T. Maeda, and Y. Aizu, "Visualising of skin chromophore concentrations by use of RGB images," Opt. Lett. 33(19), 2263-2265 (2008).

D. F. Swinehart, "The Beer-Lambert Law", Journal of chemical education 39(7), 333-335 (1962).

I. Fine and A. Weinred, "Multiple-scattering effects in transmission oximetry," Med. Biol. Eng. Comput. 31, 516-522 (1993).

I. Fine and A. Weinred, "Multiple scattering effect in transmission pulse oximetry," Med. Biol. Eng. Comput. 33, 709-712 (1995).

A. R. Guazzi, M. Villarroel, J. Jorge, J. Daly, M. C. Frise, P. A. Robbins, and L. Tarassenko, "Non-contact measurement of oxygen saturation with an RGB camera," Biomed. Opt. Express 6, 3320-3338 (2015).

W. Karlen, G. Dumont, C. Petersen, J. Gow, J. Lim, J. Sleiman, and J. M. Ansermino, "Human-centered Phone Oximeter Interface Design for the Operating Room," Proceedings of the Int. Conf. on Health Informatics, 433-438 (2011).

F. Lamonaca, D. L. Carnì, D. Grimaldi, A. Nastro, M. Riccio and V. Spagnolo, "Blood oxygen saturation measurement by smartphone camera," 2015 IEEE International Symposium on Medical Measurements and Applications (MeMeA) Proceedings, 359-364 (2015).

X. Ding, D. Nassehi and E. C. Larson, "Measuring Oxygen Saturation with Smartphone Cameras Using Convolutional Neural Networks," IEEE Journal of Biomedical and Health Informatics 23(6), 2603-2610 (2019).

Y. Shimada, I. Yoshiya, N. Oka and K. Hamaguri, "Effects of multiple scattering and peripheral circulation on arterial oxygen saturation measured with a pulse-type oximeter," Med. Biol. Eng. Comput. 22, 475-478 (1984).

M. H. Smith, "Optimum wavelength combinations for retinal vessel oximetry," Appl. Opt. 38, 258-67 (1999).

J. G. Webster, Design of Pulse Oximeters (CRC Press, Oxfordshire, United Kingdom, 1997).

G. Guven, M. P. Hilty, and C. Ince, "Microcirculation: physiology, pathophysiology, and clinical application," Blood purification 49, 143-150 (2020).

D. Lopez and C. M. Kramer, "Oxygenation and flow in the limbs: Novel methods to characterize peripheral artery disease," Current cardiovascular imaging reports 6, 150-157 (2013).

M. J. Sullivan, J. D. Knight, M. B. Higginbotham, and F. R. Cobb, "Relation between central and peripheral hemodynamics during exercise in patients with chronic heart failure. Muscle blood flow is reduced with maintenance of arterial perfusion pressure," Circulation 80, 769-781 (1989).

A. A. Frazier, T. J. Franks, T.-L. H. Mohammed, I. H. Ozbudak, and J. R. Galvin, "Pulmonary veno-occlusive disease and pulmonary capillary hemangiomatosis," Radiographics 27, 867-882 (2007).

H. M. A. Hofstee, A. V. Noordegraaf, A. E. Voskuyl, B. A. C. Dijkmans, P. E. Postmus, Y. M. Smulders, and E. H. Serné, "Nailfold capillary density is associated with the presence and severity of pulmonary arterial hypertension in systemic sclerosis," Annals of the rheumatic diseases 68, 191-195 (2009).

G. London, A. Covic, D. Goldsmith, A. Wiecek, G. Suleymanlar, A. Ortiz, Z. Massy, B. Lindholm, A. Martinez-Castelao, and D. Fliser, "Arterial aging and arterial disease: interplay between central hemodynamics, cardiac work, and organ flow—implications for CKD and cardiovascular disease," Kidney international supplements 1, 10-12 (2011).

L. Ostergaard, S. N. Jespersen, T. Engedahl, E. G. Jiménez, M. Ashkanian, M. B. Hansen, S. Eskildsen, and K. Mouridsen, "Capillary dysfunction: its detection and causative role in dementias and stroke," Current neurology and neuroscience reports 15, 37 (2015).

P. H. Tomlins and R. K. Wang, "Theory, developments and applications of optical coherence tomography," Journal of Physics D: Applied Physics 38, 2519-2535 (2005).

S. Eriksson, J. Nilsson, and C. Sturesson, "Non-invasive imaging of microcirculation: a technology review," Med Devices (Auckl) 7, 445-452 (2014).

J. Hansell, L. Henareh, S. Agewall, and M. Norman, "Non-invasive assessment of endothelial function—relation between vasodilatory responses in skin microcirculation and brachial artery," Clinical physiology and functional imaging 24, 317-322 (2004).

G. E. Gokcek, D. Kartal, N. Kalay, S. L. çinar, G. Savaş, and M. Borlu, "The relationship between the severity of coronary artery disease and skin measurement parameters," Skin Research and Technology: Official Journal of International Society for Bioengineering and the Skin (ISBS)[and] International Society for Digital Imaging of Skin (ISDIS)[and] International Society for Skin Imaging (ISSI) (2020).

M. Ohmi, M. Kuwabara, and M. Haruna, "Dynamic imaging of a small artery underneath skin surface of a human finger by optical coherence tomography," (2013).

Q. He, T. Liu, and R. K. Wang, "Enhanced spatial resolution for snapshot hyperspectral imaging of blood perfusion and melanin information within human tissue," Journal of Biophotonics 13, e202000019 (2020).

V. Y. Toronov, X. Zhang, and A. G. Webb, "A spatial and temporal comparison of hemodynamic signals measured using optical and functional magnetic resonance imaging during activation in the human primary visual cortex," Neuroimage 34, 1136-1148 (2007).

C.-L. Chen and R. K. Wang, "Optical coherence tomography based angiography," Biomed. Opt. Express 8, 1056-1082 (2017).

S. L. Davis, P. J. Fadel, J. Cui, G. D. Thomas, and C. G. Crandall, "Skin blood flow influences near-infrared spectroscopy-derived measurements of tissue oxygenation during heat stress," Journal of applied physiology 100, 221-224 (2006).

Z. Marcinkevics, U. Rubins, J. Zaharans, A. Miuks, E. Urtane, and L. Ozolina-Moll, "Imaging photoplethysmography for clinical assessment of cutaneous microcirculation at two different depths," Journal of Biomedical Optics 21, 035005 (2016).

M. Paul, A. F. Mota, C. H. Antink, V. Blazek, and S. Leonhardt, "Modeling photoplethysmographic signals in camera-based perfusion measurements: optoelectronic skin phantom," Biomed. Opt. Express 10, 4353-4368 (2019).

T. Tamura, Y. Maeda, M. Sekine, and M. Yoshida, "Wearable photoplethysmographic sensors past and present," Electronics 3, 282-302 (2014).

* cited by examiner lock-in amplification 0.00 ▭ 1.00

-180 ▭ 180

REMOTE MONITORING OF OXYGENATION STATUS AND BLOOD PULSATION WITHIN SKIN TISSUE

CROSS-REFERENCE(S) TO RELATED APPLICATION

This application is a National Stage of International Application No. PCT/US2022/017848 filed Feb. 25, 2022, which claims the benefit of U.S. Provisional Patent Application No. 63/154,100, filed Feb. 26, 2021, the disclosures of each of which are expressly incorporated herein by reference in their entirety.

BACKGROUND

Oxygen saturation (SO$_2$) is a measure of the relative concentration of oxygenated hemoglobin with respect to the total amount of hemoglobin. The human body tissue demands and auto-regulates a precise and specific balance of oxygen content within blood circulation throughout various organs and tissue types. Oxygen saturation, including peripheral SO$_2$ (SpO$_2$), is one of the key physiological indices commonly used to indicate the physical and medical conditions of a person. For instance, an abnormal level of oxygen saturation is often associated with severe medical conditions, e.g., hypoxia, chronic obstructive pulmonary disease and obstructive sleep apnea. More importantly, in the devastating COVID-19 pandemic, SpO$_2$ is a vital parameter to monitor as its decrease may reflect a compromised oxygen intake through the respiratory system, thus be alarming for a suspected infection of the coronavirus. Therefore, regular measurement and monitoring of SpO$_2$ is of great importance for at-home health monitoring and clinical practices in dealing with various medical conditions and the pandemic of COVID-19.

Current clinical gold standard for SpO$_2$ measurement is blood gas analysis with invasive blood sampling. It was not until the early 1980s that SpO$_2$ was continuously measured non-invasively with a contact-mode light-based pulse oximetry, which has revolutionized the way blood oxygen is monitored in clinical practice as well as in-hospital monitoring. The detecting principle of pulse oximetry is based on the distinct absorption difference between oxygenated (HbO$_2$) and deoxygenated hemoglobin (Hb) in the visible and near infrared wavelength range. This fact is being continually utilized in the popular development of remote, non-contact measurements of SpO$_2$ using imaging photoplethysmography (iPPG), by leveraging the advances in area array sensors, for example CCD cameras. The ability to remotely assess SpO$_2$ information could benefit both clinical and research efforts such as in the intensive care unit and sleep studies. In addition to the efforts of developing monochromatic camera-based devices, there are intense research activities over the recent years focusing on developing devices and algorithms for estimating SpO$_2$ from the RBG-channel signals provided by a color CCD camera.

The success of almost all the prior studies was essentially based on the observed relationship of the oxygen saturation to the ratio of AC/DC ratios between two wavelengths of interest, which was derived from the Beer-Lambert law. However, when using the Beer-Lambert law, only the absorbances from the chromophores within skin tissue were considered in the derivation, for example skin pigmentation, reduced and oxygenated hemoglobin.

Accordingly, methods and systems for measuring SpO$_2$ remotely with a communication device are needed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The effect of the variation caused by light scattering on the measured reflectance images was neglected in the prior art technologies, which may cause considerable errors or misinterpretation of the measured SpO$_2$. According to biomedical optics, the light scattering properties of the heterogeneous skin tissue and the absorption and scattering strength of the effective blood volume would inevitably affect the appearance of reflectance images recorded by the CCD camera. The change in reflectance depends mainly on the effective blood volume, which may be determined by many physiological factors, such as local temperature, cardiac index and peripheral vasoconstriction. Therefore, even under a stable illumination condition, the reflectance variation due to the changes in scattering and absorption can lead to a poor estimation of the relationship of oxygen saturation to the ratio of AC/DC ratios, giving rise to a considerable deviation of measured SpO$_2$ from the true value.

While the camera-array sensor approach has been the main stay for the development of remote SpO$_2$ monitoring, there is an increasing interest in the development of smartphone-based approach simply because of its ever-growing accessibility and affordability in the community. In this regard, effort has been paid to develop pulse oximeter in which a contact light sensor is connected to smartphone-based mobile devices. Mobile devices offer many advantages, such as user-friendly customer interfaces. However, the most efforts so far are based on contact-mode, requiring hardware attachments and a relative long data-recording period. This attribute makes smartphone-based contact method less attractive compared to the traditional pulse oximeter.

In one aspect, a method of measuring blood oxygenation comprising acquiring one or more images of a portion of a body with an RGB camera, converting RGB colors in the one or more images into a multispectral data imaging cube, wherein the multispectral date imaging cube comprises a red channel, a blue channel, and a green channel, decoupling an oxygenated blood information and a deoxygenated blood information from the multispectral data imaging cube based on a first reflectance of the green channel and a second reflectance of the red channel, and determining a blood measurement based on the oxygenated blood information and the deoxygenated blood information is disclosed.

In another aspect, a computer-implemented method comprising acquiring one or more images of a portion of a body with an RGB camera, converting RGB colors in the one or more images into a multispectral data imaging cube, wherein the multispectral date imaging cube comprises a red channel, a blue channel, and a green channel, decoupling an oxygenated blood information and a deoxygenated blood information from the multispectral data imaging cube based on a first reflectance of the green channel and a second reflectance of the red channel, and determining a blood measurement based on the oxygenated blood information and the deoxygenated blood information is disclosed.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
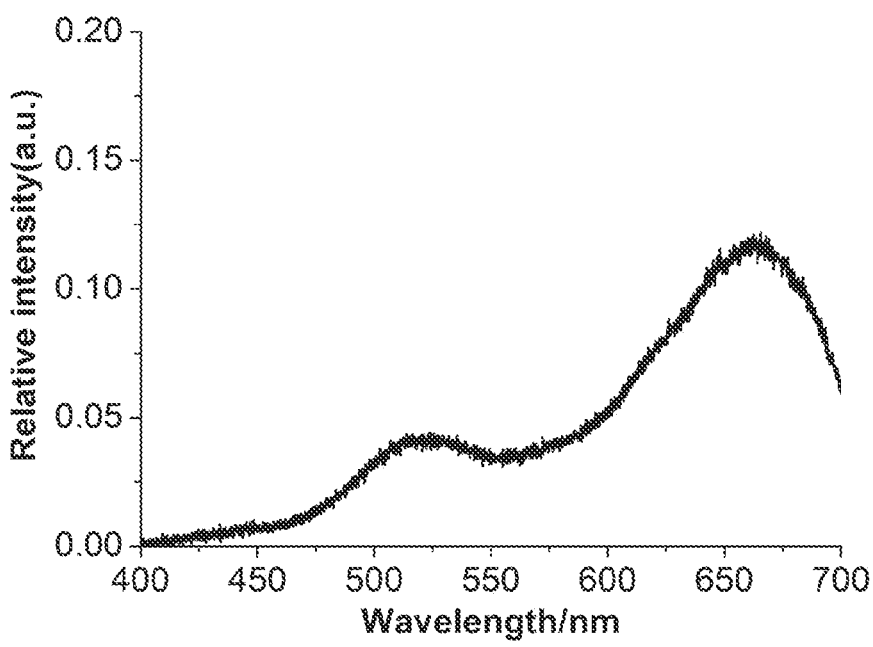
FIG. 1A is a graph of the spectral power distribution of the smartphone flashlight used in this study, in accordance with the present technology.

Described herein is a robust non-contact method to accurately estimate peripheral oxygen saturation ($SpO_2$) using a smartphone-based imaging photoplethysmography. In some embodiments, a method of measuring blood oxygenation includes acquiring one or more images of a portion of a body with an RGB camera, converting RGB colors in the one or more images into a multispectral data imaging cube, where the multispectral date imaging cube comprises a red channel, a blue channel, and a green channel. The method also includes decoupling an oxygenated blood information and a deoxygenated blood information from the multispectral data imaging cube based on a first reflectance of the green channel and a second reflectance of the red channel, and determining a blood measurement based on the oxygenated blood information and the deoxygenated blood information is disclosed. In some embodiments, the method utilizes the built-in color camera of a smartphone as a remote sensor and the built-in flashlight of a smartphone as illumination to estimate the $SpO_2$. In some embodiments, following the ratio of ratios between green and red channels, a multiple linear regression algorithm is used to improve the $SpO_2$ estimation. The algorithm considers the ratio of ratios and the reflectance images recorded at the RGB channels during a calibration process to obtain a set of weighting coefficients to weigh each contributor to the final determination of $SpO_2$.

Demonstrated herein is a smartphone-based method of estimating the $SpO_2$ on five healthy volunteers whose arms are conditioned by a manual pressure cuff to manipulate the $SpO_2$ between 90~100% as detected simultaneously by a medical-grade pulse oximeter. Experimental results indicate that the overall estimated error between the smartphone and the reference pulse oximeter is 0.029±1.141%, leading to a 43% improvement over the conventional ratio of ratios method (0.008±2.008%). In addition, the data sampling time in the current method is 2 seconds, similar to the sampling cycle used in the commercial medical-grade pulse oximeters.

Described herein is a non-contact method to estimate $SpO_2$ using smartphone-enabled imaging photoplethysmography. Following the relationship between ratio of ratios of the reflectance images recorded in RGB channels and oxygen saturation, a method of multiple linear regression (MLR) algorithm is employed to minimize the effect of changes in the light scattering due to the variations of physiological conditions on the final $SpO_2$ estimation. Demonstrate herein is a smartphone-based remote measurement of $SpO_2$ by imaging volunteers' hands conditioned by a manual blood pressure cuff to provide oxygen saturation between 90% and 100%. In parallel, the $SpO_2$ of the conditioned hands is also simultaneously measured by a medical grade contact mode pulse oximeter at fingers for training the proposed multiple linear regression algorithm as well as for comparison.

In one embodiment, a smartphone-enabled remote multispectral photoplethysmography (SP-rmPPG) system and method is used to realize spatiotemporal monitoring of perfusion changes and pulsations of the oxyhemoglobin ($HbO_2$). Deoxyhemoglobin (Hb) information within the effective blood volume within light interrogated skin tissue beds is disclosed. The system may be implemented using an unmodified smartphone utilizing its built-in camera and flashlight to acquire videos of the skin reflectance. The SP-rmPPG method converts the RGB video into multispectral cubes, upon which to decouple the dynamic changes in $HbO_2$ and Hb information using a modified Beer-Lambert law and the selective wavelength bands of 500 nm and 650 nm. Blood pulsation amplitudes are then obtained by applying a window-based lock-in amplification on the derived spatiotemporal changes in $HbO_2$ or Hb signals. To demonstrate the feasibility of proposed method, two experiments on the skin tissue beds that are conditioned by occlusive maneuver of supplying arteries were conducted: one using the popular blood cuff pressure maneuver on the upper arm, and another artificially inducing a transient ischemic condition on the facial skin tissue beds by finger pressing on the supplying external carotid artery are disclosed. The results from the two experiments sufficiently demonstrate the feasibility of the proposed method to monitor the spatiotemporal changes in the skin hemodynamics, including blood oxygenation and pulsation amplitudes. Considering the ever-growing accessibility and affordability of the smartphone to the general public, the proposed inventive technology promises the early screening of vascular diseases and improving general public health particularly in rural areas with low resource settings.

The primary function of the microcirculation is to supply oxygen and nutrients to the local tissue. Microcirculation status, hence capillary hemodynamics, plays an important role in regulating blood flow and tissue oxygenation, thus being well recognized in the vital sign monitoring, as well as in the study of vascular function, peripheral artery diseases and cardiovascular disorders. Therefore, non-invasive and contactless techniques to assess microcirculatory behaviors and hemodynamic contents are indispensable for clinical practices and daily assessment of medical conditions.

Skin, being the largest and capillary-rich organ, provides an easily accessible window for developing such techniques to access the hemodynamic information inside the human body. Thanks to the translucent property of skin at visible and near infrared (NIR) wavelengths, optical methods may be developed to derive signals (measurands) that are indicative of blood hemodynamics, for example blood perfusion, oxygen saturation, pulsation etc. Among these optical methods, photoplethysmography (PPG) is becoming one of the most popular techniques and being widely used for in-hospital monitoring and even in wearable devices nowadays. Due to the strong absorption of blood to the light, PPG works by recording time-elapsed optical reflectance modulated by the effective blood volume within light interrogated tissue volume to indicate the dynamic pulsatile behavior of the blood flow (volume) caused by cardiac heartbeat. With this dynamic and pulsatile blood flow behavior directly obtained from the human skin tissue, PPG can be used to monitor the heart rate, cardiac cycle and respiration.

However, PPG is often implemented through a contact approach between sensors and skin, prone to motion artifacts. To solve this problem, remote PPG (rPPG) has been proposed and developed. rPPG is typically implemented by a camera-based system that is used to acquire the video of skin surface, from which to derive the pulse waveforms. Using dedicated signal processing algorithms, subtle momentary changes in the skin reflection in the video can be extracted. The remote attribute of rPPG is its most attractive advantage compared to the conventional PPG. However, since global parameters are addressed in the above applications, there is still a demand to develop techniques that can be used to perform the spatiotemporal analysis of rPPG and explore its potential applications.

As exciting as the rPPG delivers, however, previous developments were not able to decouple the hemoglobin compositions from the acquired signals, e.g., oxygenated (HbO$_2$) and deoxygenated (Hb) blood. This additional information is critical for improved understanding of the microcirculatory function and hemodynamic regulations. In most cases, changes in pulsation and oxygenation detected at the peripheral site would manifest changes in supplying arteries or systemic blood flow Herein, a smartphone-enabled remote multispectral photoplethysmography (SP-rmPPG) system and method to provide a spatiotemporal monitoring of the perfusion changes and pulsations of HbO$_2$ and Hb in the human skin is disclosed. The method first converts the RGB video into the multispectral data imaging cube (or multispectral data cube) 500, upon which to derive and decouple spatiotemporal HbO$_2$ and Hb information within the effective blood volume utilizing a modified Beer-Lambert law and dual-waveband processing method. Then, a method is used to obtain the spatiotemporal pulsation amplitudes of both two types of oxygenated and deoxygenated bloods by applying a window-based lock-in amplification approach. To demonstrate the feasibility and performance of the proposed method, two experiments are performed by imaging two peripheral skin sites in health volunteers while conditioning the upstream blood supply and drainage, with an aim to delineate the changes in HbO$_2$ and Hb modulation and pulsation strength upon the challenging.

In some embodiments, decoupling oxygenated blood information and the deoxygenated blood information includes recording the first reflectance at the green channel and the second reflectance the red channel calculating a ratio of ratios from the first reflectance of the green channel and the second reflectance of the red channel, wherein the ratio of ratios is determined as

8

$$R = \frac{\varepsilon_{Hb}(\lambda_1) + [\varepsilon_{HbO_2}(\lambda_1) - \varepsilon_{Hb}(\lambda_1)]SO_2}{\varepsilon_{Hb}(\lambda_2) + [\varepsilon_{HbO_2}(\lambda_2) - \varepsilon_{Hb}(\lambda_2)]SO_2}$$

where $\varepsilon Hb$ is an extinction coefficient of the deoxygenated blood, $\varepsilon HbO_2$ is an extinction coefficient of the oxygenated blood, $\lambda 1$ is a first wavelength, $\lambda 2$ is a second wavelength, and $SO_2$ is an oxygen saturation and measuring an average gray value of the red channel, green channel, and blue channel, wherein the average gray value is the sum of the gray values of all the pixels in the image divided by the number of pixels.

Oxygen saturation is used to indicate the extent to which hemoglobin is saturated with oxygen, which is defined as:

$$SO_2 = \frac{HbO_2}{Hb + HbO_2} \tag{1}$$

where $HbO_2$ is oxygenated hemoglobin, and Hb is reduced hemoglobin. The concentrations of oxygenated hemoglobin ($cHbO_2$) and reduced hemoglobin (cHb) can be expressed as a function of $SO_2$:

$$c_{HbO_2} = SO_2(c_{HbO_2} + c_{Hb}) \tag{2}$$

$$c_{Hb} = (1 - SO_2)(c_{HbO_2} + c_{Hb}) \tag{3}$$

During propagation within skin tissue, the light intensity is progressively reduced due to the presence of absorbing chromophores, e.g., skin pigmentation, bones, the arterial and venous blood, following the Beer-Lambert law. The heartbeat also leads to the pulsatile variation in the blood volume. Thus, the total absorbance represented at the reflectance captured by the remote cameras contains DC component and AC component. The DC component is due to the absorbance caused by venous blood, a constant amount of arterial blood and other non-pulsatile components such as skin pigmentation. And the AC component is due to the pulsatile nature of the blood volume within the light interrogated skin tissue volume.

At diastole, the diameter of the arterial vessels is minimal and therefore the absorbance due to the hemoglobin in arterial blood is minimal, leading to higher reflectance recorded by the camera (IH). On the other hand, the arteries contain more blood during systolic phase, and therefore, the optical path length in the arteries increases. The amount of light being absorbed reaches maximum, giving rise to a minimal reflectance (IL). According to the Beer-Lambert law, IH and IL could be expressed as:

$$I_H = I_0 e^{-A_{DC}} e^{-A_{t,H}} \tag{4}$$

$$I_L = I_0 e^{-A_{DC}} e^{-A_{t,L}} \tag{5}$$

where $I_0$ is the intensity of incident light. $A_t = \varepsilon_{Hb}(\lambda) c_{Hb} d_{Hb} + \varepsilon_{HbO_2}(\lambda) c_{HbO_2} d_{HbO_2}$ is the absorbance that only containing reduced (Hb) and oxygenated (HbO$_2$) hemoglobin as the absorbing substances with their corresponding extinction coefficient, concentration and optical pathlength as being represented by $\varepsilon$, c and d, respectively. All DC components except the pulsating arterial blood are collectively represented by the effective $A_{DC} = \ominus_{DC}(\lambda) c_{DC} d_{DC}$.

In order to eliminate the influence of DC components, the ratio of absorbances at two wavelengths (defined as ratio of ratios) could be expressed as:

$$R = \frac{A_t \lambda_1}{A_t \lambda_2} = \frac{\ln(I_L \lambda_1 / I_H \lambda_1)}{\ln(I_L \lambda_2 / I_H \lambda_2)} \quad (6)$$

Assuming that the optical path length d is the same for the oxygenated hemoglobin ($d_{HbO_2}$) and reduced hemoglobin ($d_{Hb}$) and the optical path lengths for the two wavelengths are equal, using Eqs. (2) and (3), Eq (6) can be reduced to:

$$R = \frac{\varepsilon_{Hb}(\lambda_1) + [\varepsilon_{HbO_2}(\lambda_1) - \varepsilon_{Hb}(\lambda_1)]SO_2}{\varepsilon_{Hb}(\lambda_2) + [\varepsilon_{HbO_2}(\lambda_2) - \varepsilon_{Hb}(\lambda_2)]SO_2} \quad (7)$$

In this form, the ratio of ratios (R) is not a function of the optical path length and can be derived from the oxygen saturation instead of the concentration of the hemoglobin in the blood.

Equation (7) can be rewritten in a form where $SO_2$ is a function of the measured and calculated ratio R:

$$SO_2 = \frac{\varepsilon_{Hb}(\lambda_1) - \varepsilon_{Hb}(\lambda_2)R}{[\varepsilon_{Hb}(\lambda_1) - \varepsilon_{HbO_2}(\lambda_1)] + [\varepsilon_{Hb}(\lambda_2) - \varepsilon_{HbO_2}(\lambda_2)]} \times 100\% \quad (8)$$

Equation (8) is the calibration equation used for estimating oxygen saturation based on the ratio of ratios method. However, the derivation procedures described above are valid based on several assumptions. The most important one is that the Beer-Lambert law assumes no effect of light scattering on the images recorded by the remote CCD sensors, which is however not true in practice. It has been demonstrated that the influence of light scattering on the measurement cannot be removed by simply subtracting the DC signals. In this case, the total absorbance due to whole blood volume within the interrogated tissue volume should be expressed as the sum of absorbance as described by the Beer-Lambert law (At) and a second term representing the changes in light scattering (ΔAt). Thus, according to the non-linear variation of pulsatile blood volume in Eq. (6) and using Eq. (8), the $SO_2$ is actually the function of R and ΔR:

$$S\hat{O}_2 \sim R + \Delta R \quad (9)$$

where ΔR is the deviation of ratio of ratios caused by the change in light scattering.

To account for scattering effect, an optimal set of three wavelengths in the implementation of oximetry where two isosbestic wavelengths are used to estimate the contribution by optical scattering, and a third wavelength is used for $SO_2$ sensitivity was introduced. While three-wavelength oximetry may offer improved accuracy over two-wavelength oximetry by accounting for scattering, the choice of potential imaging wavebands is rather specific and in fact limited, which would not be suitable for the development of smartphone-based remote pulse oximetry.

As stated, the effective blood volume within the light interrogated tissue volume is influenced by many physiological factors such as the local temperature, cardiac index, peripheral vasoconstriction etc. In the meantime, the variations in effective blood volume due to its pulsatile nature from the heartbeats cause a change in the light scattering in addition to light absorption, which subsequently alters the appearance of light reflectance recorded by the CCD camera. This change in the reflectance images would be represented by a change in the gray value of images recorded at all the RGB channels. Therefore, AR may be mainly represented by the gray value variation recorded by the RGB sensors, which can be utilized to improve the $SpO_2$ estimation.

In some embodiments, determining the blood measurement includes applying a multiple linear regression algorithm to the oxygenated blood information and the deoxygenated blood information based on the calculated ratio of ratios and the averaged gray values of the red channel, green channel, and blue channel.

Incorporating the reflectance changes at the RGB channels into the SpO2 estimation in addition to the ratio of ratios, the problem may be taken as a multifactorial process. To deal with this problem, the multifactorial process was approximated using multiple linear regression (MLR) method in which the oxygen saturation is expressed by:

$$y = \beta_0 + \beta_1 \cdot R + \beta_2 \cdot h_{Green} + \beta_3 \cdot h_{Red} + \beta_4 \cdot h_{Blue} + \epsilon \quad (10)$$

where y is the oxygen saturation. R, $h_{Green}$, $h_{Red}$ and $h_{Blue}$ are the variables determined by the actual measurements, which represent the ratio of ratios, the mean gray values of the reflectance images recorded at Green, Red and Blue channels, respectively. $\beta_i$ (i=0, 1, . . . , 4) are the weighting coefficients used to weigh the contribution of the measured variables to y. $\epsilon$ is a noise term in the process. The problem now is reduced to the determination of a set of weighting coefficients $\beta_i$ (i=0, 1, . . . , 4).

In some embodiments, the method further comprises calibrating the RGB camera with a Weiner estimation method and a color-checker. In this case, the determination can be achieved with a calibration process, given a set of reference measurements of the oxygen saturation, y. In the calibration process, the target sample is conditioned to provide a range of known $SpO_2$ and in the meantime, it is sampled by the smartphone 100 to give the measured signals at the RGB channels. This process gives rise to the training datasets. For each measurement in the training, the $SpO_2$ can be indicated by $$y_i = \beta_0 + \beta_1 \cdot R_i + \beta_2 \cdot h_{Green,i} + \beta_3 \cdot h_{Red,i} + \beta_4 \cdot h_{Blue,i} + \epsilon_i \quad (11)$$

where i=1, 2, . . . , N, meaning the target sample is conditioned to provide N levels of $SpO_2$.

Given the N measurements, the Eq. (11) can be expressed in a matrix form:

$$y = X\beta + \varepsilon \text{ where,} \quad (12)$$

$$y = \begin{bmatrix} 1 & R_1 & h_{Green,1} & h_{Red,1} & h_{Blue,1} \\ 1 & R_2 & h_{Green,2} & h_{Red,2} & h_{Blue,2} \\ \vdots & \vdots & \vdots & \vdots & \vdots \\ 1 & R_n & h_{Green,N} & h_{Red,N} & h_{Blue,N} \end{bmatrix}, \beta = \begin{bmatrix} \beta_0 \\ \beta_1 \\ \beta_2 \\ \beta_3 \\ \beta_4 \end{bmatrix}$$

Each element in the matrix X is directly determined from the measurements at the RGB channels in the smartphone 100. Since $X \in CN \times 5$ is not a square and invertible form when $N \neq 5$, singular value decomposition [28] can be used to calculate $\beta$. X could thus be expressed as:

$$X = U\Sigma V^* \quad (13)$$

where the columns of U and V are left singular vectors and right singular vectors, respectively. The diagonal elements of $\Sigma$ are the singular values. Here * denotes the complex conjugate transpose. Thus, Eq. (12) could be expressed as $$y = U\Sigma V^* \beta + \epsilon \quad (14)$$

Finally, the optimized β at minimal sum of squared errors can be obtained by $$\beta = V\Sigma{-1}U^*y \qquad (15)$$

After calibrating with the training dataset, β is then obtained and stored for later use in the multiple linear regression of Eq. (10) for each smartphone 100 imaging session to estimate the SpO$_2$ of the target sample.

In some embodiments, the date from the image taken with the smartphone 100 is converted into a multispectral data imaging cube. In some embodiments, the multispectral data imaging cube represents spectral information at wavelengths of 450, 500, 550, 600, 650 and 700 nm Conventional contact-sensor based pulse oximeter generally adopts the wavelengths of 660 nm (Red) and 940 nm (Infrared). In some embodiments, the present technology uses the intact and unmodified smartphone 100 to provide the oximetry function without employing additional add-on hardware. However, the use of the standard red and infrared LEDs for illumination on a consumer smartphone 100 is not possible without modification of the smartphone 100 hardware. In addition, the RGB sensors in the smartphone 100 present very low QE (Quantum Efficiency) at infrared waveband. Therefore, the selection of wavelengths for the smartphone-based non-contact oximetry should consider the characteristics of the built-in RGB sensors and the use of built-in flashlight for illumination.

Figure 1B:
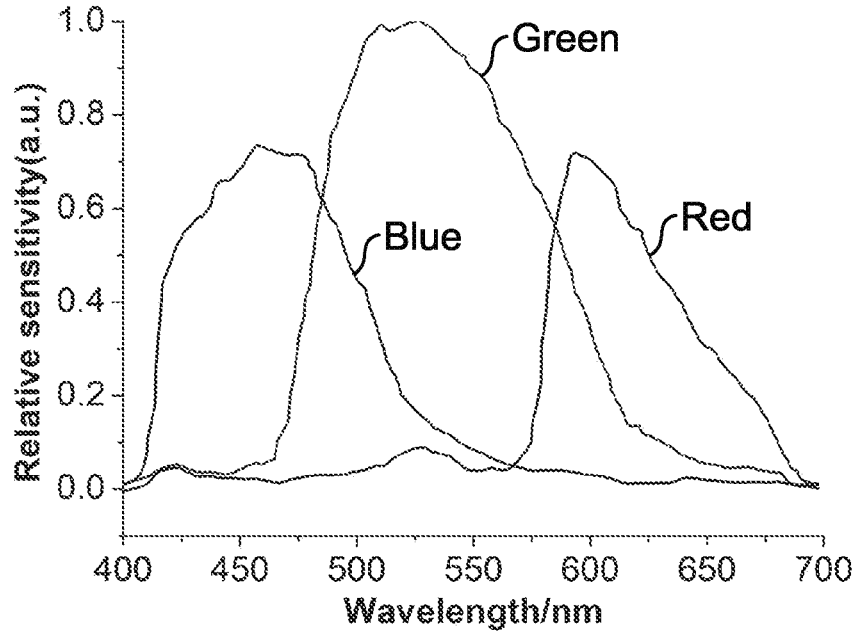
FIG. 1B shows the relative spectral sensitivity of Red, Green and Blue channels of the smartphone camera, in accordance with the present technology.
Figure 1C:
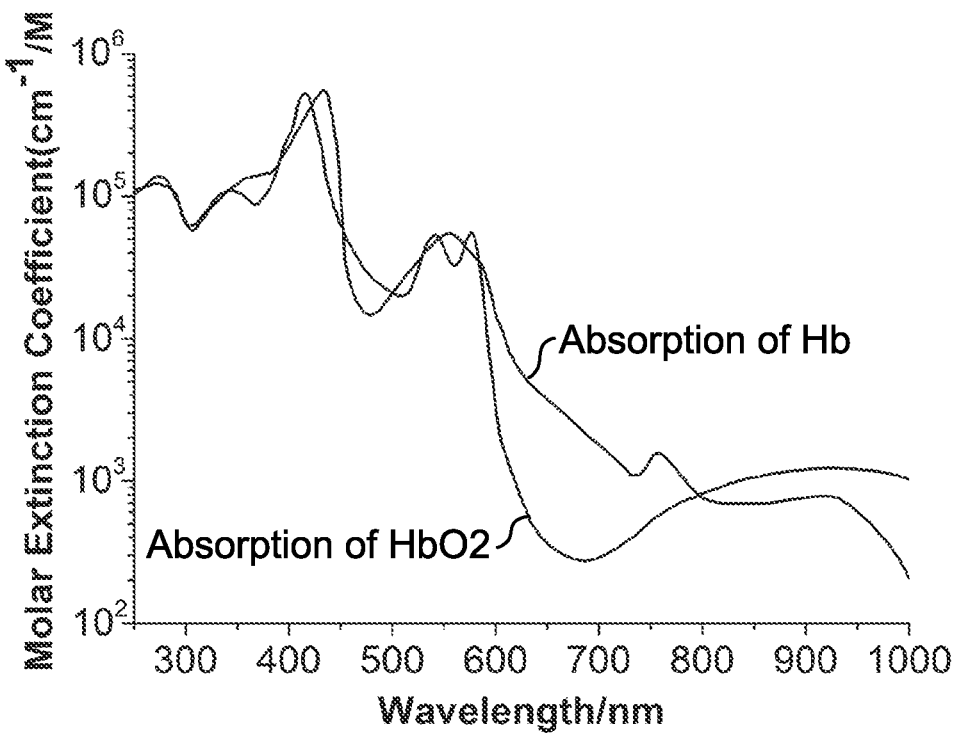
FIG. 1C is a graph of the absorption spectra of oxyhemoglobin and hemoglobin, in accordance with the present technology.
Figure 1D:
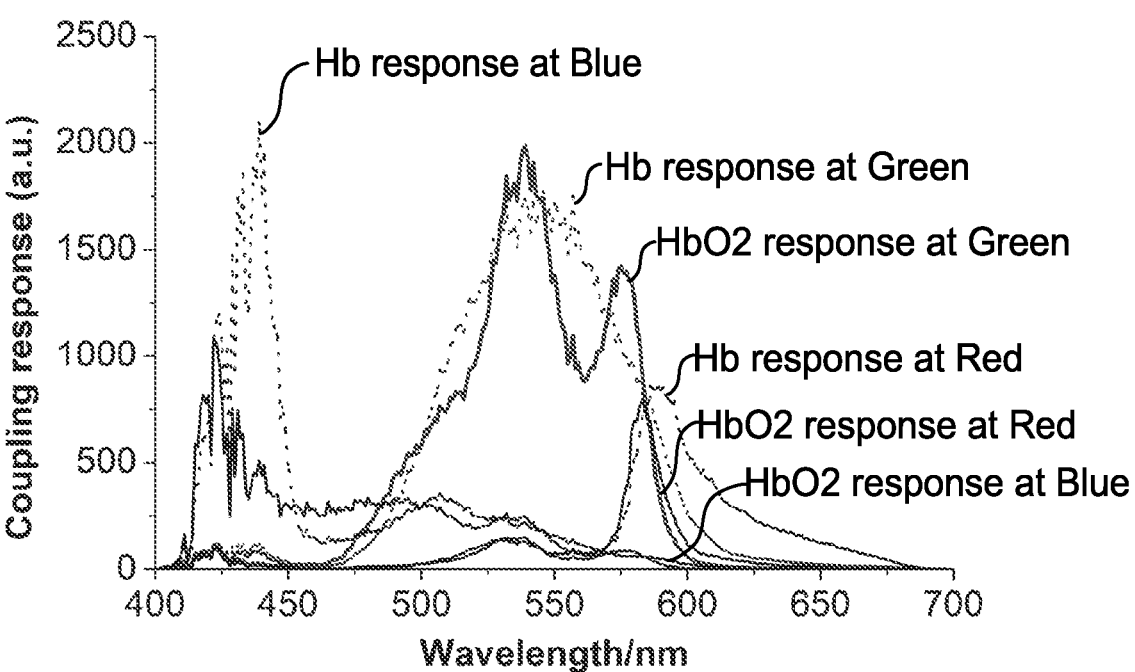
FIG. 1D is a graph of the combined response curves of flashlight, hemoglobin and camera RGB sensors when recording the reflectance images, in accordance with the present technology.

FIGS. 1A-1D are a selection of wavelengths for oxygen saturation calculation. FIG. 1A is a graph of the spectral power distribution of the smartphone flashlight 300 used in this study, in accordance with the present technology. On the horizontal axis is the wavelength in nanometers. On the vertical axis is the relative intensity in arbitrary units (a.u.). FIG. 1B shows the relative spectral sensitivity of Red, Green and Blue channels of the smartphone camera 200, in accordance with the present technology. On the horizontal axis is the wavelength in nanometers. On the vertical axis is the relative sensitivity in arbitrary units. FIG. 1C is a graph of the absorption spectra of oxyhemoglobin and hemoglobin, in accordance with the present technology. On the horizontal axis is the wavelength in nanometers. On the vertical axis is the molar extinction coefficient in cm$^{-1}$/M. FIG. 1D is a graph of the combined response curves of flashlight, hemoglobin and camera RGB sensors when recording the reflectance images, in accordance with the present technology. On the horizontal axis is wavelength in nanometers. On the vertical axis is the coupling response in arbitrary units.

When recording the reflectance images emerging at the sample illuminated by the built-in flashlight, the end-result would be a combined effect among the power spectral distribution of the flashlight, the spectral sensitivity of each RGB sensor at the smartphone camera 200 and the absorption spectra of the chromophores of interest presented in the sample. In order to simulate the response of HbO$_2$ and Hb at specific RGB channels of smartphone camera 200 with built-in flashlight illumination, an iPhone X from Apple Inc was used as an example smartphone 100 and illumination source 300. FIG. 1A shows the spectral power distribution of its flashlight across the wavelength range from 400 nm to 700 nm. FIG. 1B illustrates the spectral response curves of the red, green and blue channels of its built-in camera, respectively. FIG. 1C gives the absorption spectra of the HbO$_2$ and Hb, respectively, where HbO$_2$ and Hb has similar absorption coefficient at green channel whereas they exhibit a relatively large difference between blue and red channels. Therefore, the end-product of the camera that records the reflectance images due to the absorbance of HbO$_2$ or Hb is the product of the three spectral curves presented in FIG. 1A-C, respectively. The results are shown in FIG. D.

The wavelength selection of dual-wavelength oximeter should obey the following requirements. First, the absorption coefficients of HbO$_2$ and Hb should differ greatly at one wavelength. Second, there should be approximately equal absorption coefficient in terms of HbO$_2$ and Hb at the other wavelength. In this case, the difference of integral value between HbO$_2$ and Hb at Red channel is about 2×104, whereas the corresponding difference at Green channel is about 1×103. Therefore, the red channel would approximately satisfy the first requirement, whereas the green channel meets the 2nd requirement. In addition, because the flashlight illumination presents relatively low spectral power intensity at blue channel (425~500 nm), it inevitably exhibits relatively low signal to noise ratio (SNR), thus should be avoided for the evaluation of the ratio of ratios. Consequently, the reflectance images recorded at green and red channels are chosen for calculating the ratio of ratios, which, together with the averaged gray values obtained at the RGB channels, are used in the MLR algorithm to estimate the oxygen saturation of the target sample.

In some embodiments, the method further comprises taking the oxygenated blood information and the deoxygenated blood information from a first region of a body and a second region of a body in an image. In some embodiments, the one or more images shown in FIG. 3A comprise a video. In some embodiments, the method further comprises taking the oxygenated blood information and the deoxygenated blood information from a first region of a body and a second region of a body in the video. In some embodiments, a method and system of micro-motion imaging (μMI) to realize non-contact measurement and bilateral symmetry analysis of neck pulses is disclosed. In some embodiments, the system employs a 16-bit resolution of camera to acquire videos of the neck skin, containing the reflectance variation caused by the neck pulses. Regional amplitudes and phases of pulse-induced reflection variation are then obtained by applying a lock-in amplification algorithm on the acquired videos. In some embodiments, the method further comprises performing bilateral asymmetry analysis on the oxygenated blood information and the deoxygenated blood information of both the first region of the body and the second region of the body. In some embodiments, performing bilateral asymmetry analysis comprises generating a phase map and an amplitude map, and regionally extracting a first pulse signal from the first region of the body, and a second pulse signal from the second region of the body. In some embodiments, generating the phase map and the amplitude map comprises filtering the first pulse signal and the second pulse signal with one or more heartbeat frequencies to generate a filtered signal, and using the filtered signal as a reference function to extract and amplify the first pulse signal and the second pulse signal with the same frequency as the filtered signal at each voxel of the image or video.

In some embodiments, the first region of the body comprises a carotid region of a neck and the second region of the body comprises a jugular region of a neck. In some embodiments, the first pulse signal comprises a carotid pulse, and the second pulse signal comprises a jugular vein pulse. Following the guidance of the phase maps, carotid pulse (CP) and jugular vein pulse (JVP) waveforms are extracted. Meanwhile, the derived phase map is used to monitor the bilateral asymmetry of neck pulses induced by warm-water pad stimulation on the distal scalp tissue beds of unilateral head. Experimental results sufficiently demonstrate the feasibility of the method to accurately extract and analyze CP and JVP waves. Compared with conventional methods, the proposed strategy works in a non-contact and non-invasive manner, which is important for patient compliance in the measurements. Besides, the measurements and analyses of neck pulse waves are highly independent and self-guided, which can be achieved without a need of dedicated experts to operate, eliminating the issue of operator-dependency in the measurements. Considering the close relationship between neck pulses and cardiovascular diseases, for example carotid artery stenosis, the proposed µMI system and method promise an early screening tool for potential cardiovascular diseases.

Cardiovascular diseases lead to millions of deaths worldwide each year, giving rise to heavy social burden due to its high morbidity and fatality. Numerous methods, such as computed tomography angiography and cardiovascular magnetic resonance imaging, have been developed in response to fighting cardiovascular diseases, aiming for diagnosis, monitoring and treatment management. However, let alone their high cost, these devices require special and dedicated expertise to properly operate, which somehow prevent them from being easily accessible by public. Currently, the lack of accessible diagnostic and monitoring tools is responsible for the slow development of possible effective screening method for this disease. To meet this challenge, researchers have made good attempts to develop camera-enabled skin imaging methods, including thermal imaging, autofluorescence imaging and hemodynamics imaging methods, to assess the cardiovascular functions. However, the derived signals from the body-skin surface in these methods are highly dependent on cutaneous tissue structures, capillary beds, and pigment features, which can affect their accuracy to predict dysfunctions in large blood vessels and hearts. Therefore, there is a demand to develop more cost-effective techniques that can directly reflect the health status of cardiovascular system.

Following the contraction and relaxation of each heart cycle, a pressure wave would be generated that propagates through the body via blood vessels. When it passes across the carotid artery and the jugular vein, it causes the blood flow volume in them to show pulsatile variations, producing carotid pulsation (CP) and jugular vein pulsation (JVP) waves. A CP waveform usually consists of a forward wave and a reflective wave, whereas a typical JVP waveform shows three positive deflections, "a", "c" and "v" waves, and two descents, "x" and "y" waves. These sub-waves are closely related to cardiac cycle and blood flow conditions, thus may be leveraged for clinical use in the monitoring and even prediction of cardiac and cardiovascular abnormalities. As a result, accurate measurements of CP and JVP waveforms would be of clinical interests in both the assessment and the screening of cardiovascular diseases.

In response to this clinical interest, researchers have attempted a number of methods to assess the CP and JVP waveforms, including both invasive and non-invasive strategies. For example, central venous catheterization is used to measure JVP waveforms by inserting a catheter into jugular veins. This invasive method is currently the gold standard in clinic but requires surgical expertise and often causes the pain to patients. Doppler ultrasound imaging is another commonly-used tool for the measurement of pulse waves from the carotid artery and jugular vein. However, Doppler ultrasound imaging requires both expensive devices and well-trained operators. Recently, photoplethysmography (PPG) technique has been applied to provide pulse waveforms by placing an optical sensor on the skin regions of interest (ROI), overlaying the arteries or veins. The blood pulsation in these large vessels gives rise to the variations of light absorption, thus can be detected by the optical sensor. However, typical PPG device works in a contact mode. In addition to the possible discomfort to patients, it requires an accurate positioning to guide the extraction of pulse waveform from the measurements. This guidance is usually provided by additional techniques, unavoidably increasing the complexity in measurements.

In some embodiments, a camera-based micro-motion imaging (µMI) method to image regional motions of neck skin to enable a non-contact measurement and analysis of CP and JVP waves is disclosed. Blood pulsation in large vessels introduces periodical pressures to the surrounding tissue. Due to relatively stronger pulses and more superficial positions of common carotid arteries and jugular veins, the pressure waves generated by the CP and JVP pulsation located within the neck skin tissue beds can propagate to the skin surface, leading to relatively larger surface motions at the region overlying these vessels than other regions. In some embodiments, videos of the light reflectance were taken from the skin surface located at the neck region to capture the tissue micro-motions, upon which to extract their blood-pulsation-related components with lock-in amplification algorithm. Since the blood pulsations in arteries and veins vary in phases and amplitudes (strengths), the generated tissue motions are assumed to show regional diversity as well. In the measurements, the waveforms of CP and JVP are then regionally extracted under the guidance of phase map for more accurate assessments. Besides, the extracted phase information of motions is further used to conduct bilateral asymmetry analysis when the scalp skin tissue on unilateral head is challenged with a warm-water pad. The experimental results show that pulse waveforms can be faithfully extracted, and their phases successfully detect the simulated cardiovascular abnormality.

EXAMPLE #1

Figure 2:
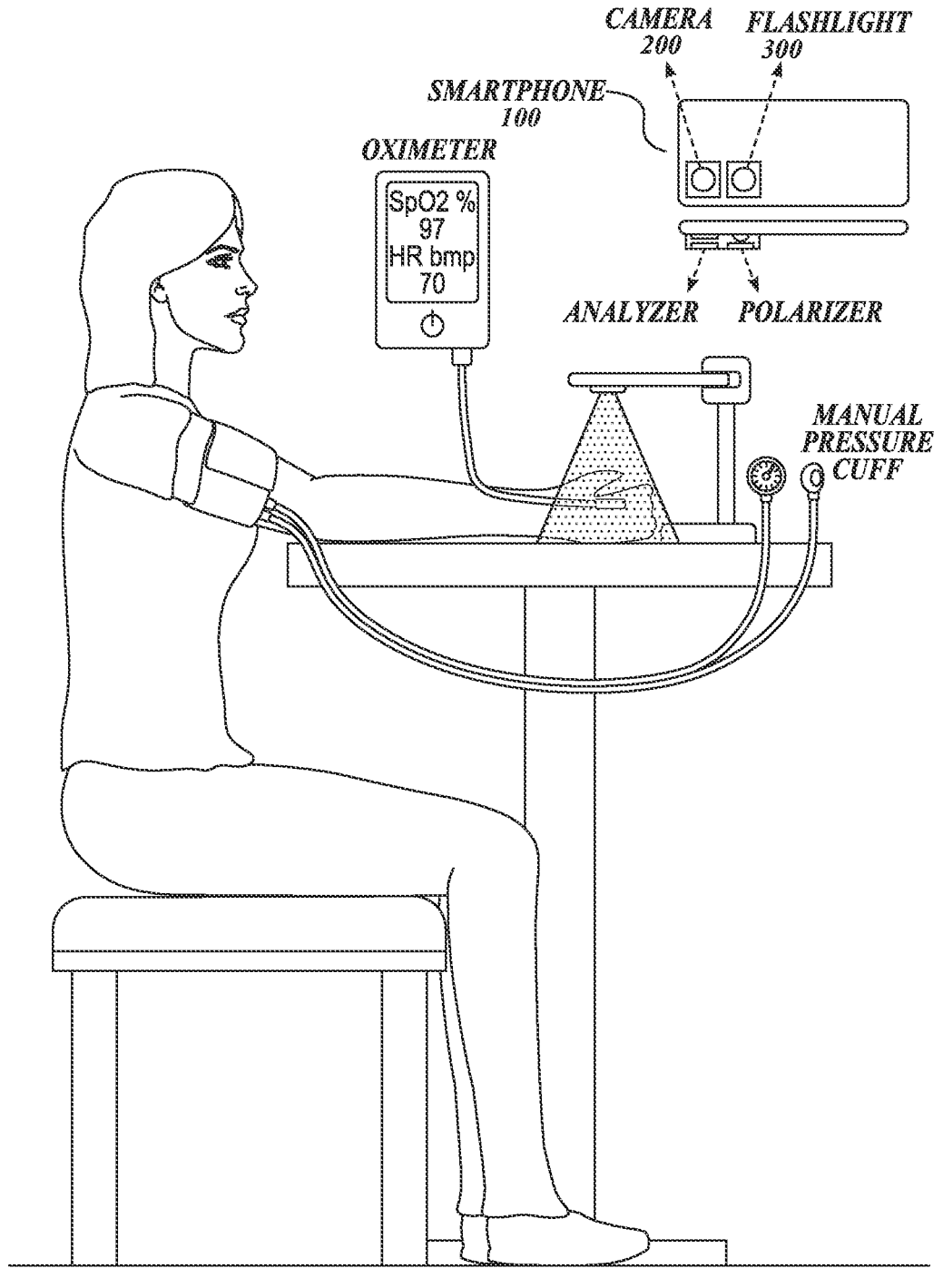
FIG. 2 is a schematic of calibrating oxygen saturation with smartphone and commercial oximeter, in accordance with the present technology.

FIG. 2 is a schematic of calibrating oxygen saturation with smartphone 100 and commercial oximeter, in accordance with the present technology. Illustrated is a schematic diagram of the experimental setup used to provide remote measurement of SpO$_2$ at the dorsal site of the volunteer's hand, consisting of a smartphone 100 (iPhone X, Apple Inc, USA), a reference contact-mode sensor-based pulse oximeter (PC-66H Handheld Pulse Oximeter, CMI Health, USA), and a manual blood pressure cuff (Aneroid sphygmomanometer, ParaMed, Canada).

In some embodiments, the method further includes illuminating the portion of the body with a light source while acquiring the one or more images of the portion of the body. In some embodiments, the light source is on the communication device. The video reflectance images from the skin surface illuminated by the built-in flashlight in the iPhone were recorded by the built-in rear camera. The iPhone X was used for demonstration purpose only, but any other types of smartphones or communication device, such as a laptop or a tablet can be used. The distance between the smartphone camera 200 and the dorsal skin surface of the volunteer's hand was kept at about 30 cm. The frame rate for video recording was set at 60 frames per second. A polarizer sheet was placed at the output of flashlight and an analyzer sheet in front of the camera. The polarizer and analyzer were orthogonally oriented to minimize the specular reflection at the skin surface so that the reflection signal from within the tissue sample could be maximized.

The medical grade contact-mode sensor-based pulse oxi-meter was used in parallel with the camera video recording, which provided the reference SpO$_2$ measurements that were used in the training process of the MLR algorithm to obtain the needed set of weighting coefficients (i.e., Eq. 15). The pulse oximeter was also used for the comparison of the measured SpO$_2$ derived from the conventional ratio of ratio method and the proposed MLR method here.

The standard medical grade manual pressure cuff was used to condition the oxygen saturation in the volunteer's hand to provide the SpO$_2$ values ranging from 90% to 100%, to which the contact-mode pulse oximeter and the remote-mode smartphone 100 measure. It should be noted that FIG. 2 illustrates the calibration (or training) process of smart-phone based on a commercial oximeter. During the measur-ing step, only smartphone 100 is used. For experimental demonstration, five healthy volunteers were enrolled in this study, with subject information shown in Table 1 including the skin color (indicated by the Fitzpatrick scale). All measurements were performed in a standard lab environ-ment. All room windows were covered so as to minimize the amount of stray light from any source other than the flash-light of the smartphone 300. Volunteers were instructed to sit comfortably and quietly on a chair. The experiment began after allowing 10-min accommodation of the lab environ-ment. The manual blood pressure cuff was placed on the left arm that was finely controlled to realize the SpO$_2$ at the hand ranging from 90% to 100%. The reference SpO$_2$ data was recorded using the contact-mode pulse oximeter positioned on the little finger, with a sampling time of 2-4 seconds and a reported accuracy of 2~3% between 70% and 100% of the SpO$_2$. In parallel, the video reflectance images from skin surface of the volunteer were recorded by the smartphone 100.

Multiple trials (n=3 to 5 depending on conditions during data recording) were conducted on each subject following the same procedure as described above. Each trial consisted of multiple levels of SpO$_2$ from 90% to 100% at the fingertip as measured by the pulse oximeter and controlled by the manual blood pressure cuff on the upper arm. At each level of SpO$_2$, the video images recorded by the iPhone were approximately 10-15 seconds in duration, but truncated to multiple 2-second non-overlapping segments (i.e., dataset) for later processing.

TABLE 1

Demographic information of the volunteers including skin color type (Fitzpatrick scale)

| Volunteer | 1 | 2 | 3 | 4 | 5 |
|---|---|---|---|---|---|
| Age | 38 | 26 | 32 | 37 | 25 |
| Gender | Male | male | male | male | female |
| Fitzpatrick Type | II | III | IV | III | II |

To obtain a more accurate estimation of oxygen satura-tion, valid data should obey the following two criterions. Firstly, during data recording, the reference oxygen satura-tion read at the pulse oximeter should maintain stable for more than 10 seconds. Secondly, the AC components of iPPG signal should not excess three times the average baseline of AC component. The datasets after passed this quality check were made available for further processing and evaluation. Listed in Table 2 are the numbers of valid datasets from all the volunteers participated in this study, with each dataset corresponding to its unique SpO$_2$ reading by the pulse oximeter in parallel.

TABLE 2

Number of valid datasets from the participating volunteers

| Volunteer | 1 | 2 | 3 | 4 | 5 |
|---|---|---|---|---|---|
| # in total | 128 | 93 | 64 | 53 | 17 |
| # for training | 64 | 50 | 30 | 0 | 0 |
| # for validating | 64 | 43 | 34 | 53 | 17 |

Figure 3A:
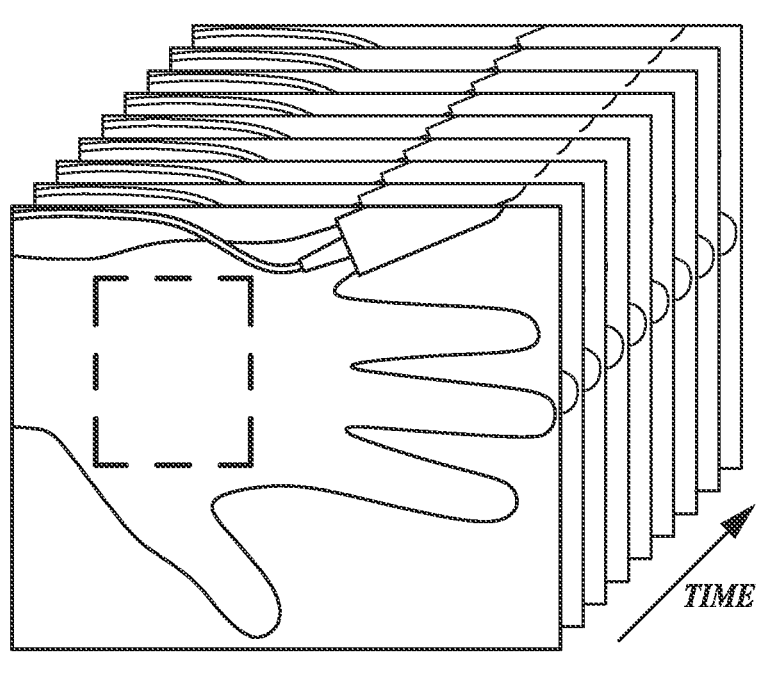
FIG. 3A is a video sequence is illustrated along the time axis where the region of interest (ROI) is marked with dotted line box for evaluation, in accordance with the present technology.
Figure 3B:
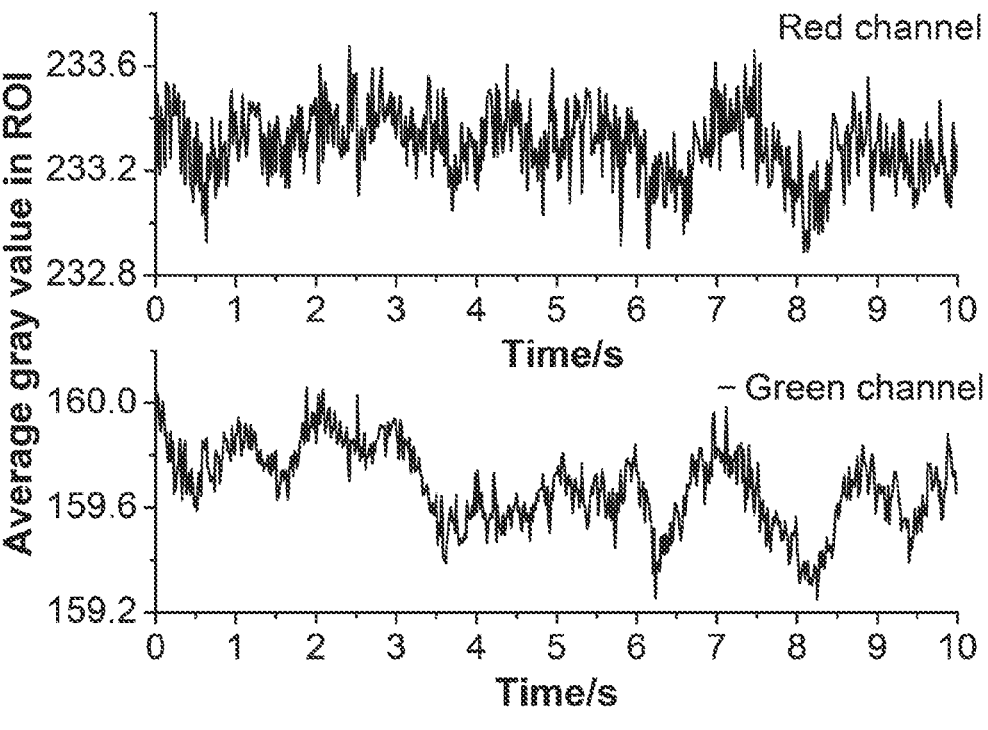
FIG. 3B is a graph of the evolution of the spatially-averaged values within the ROI, in accordance with the present technology.
Figure 3C:
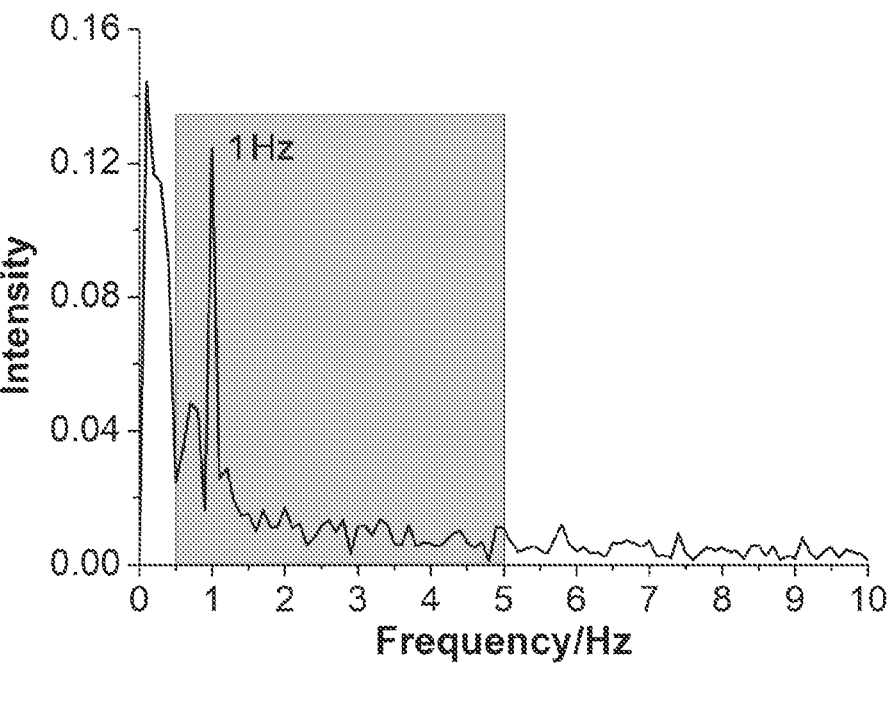
FIG. 3C is a graph of the Fourier spectra of the time series signal at the green channel, in accordance with the present technology.
Figure 3D:
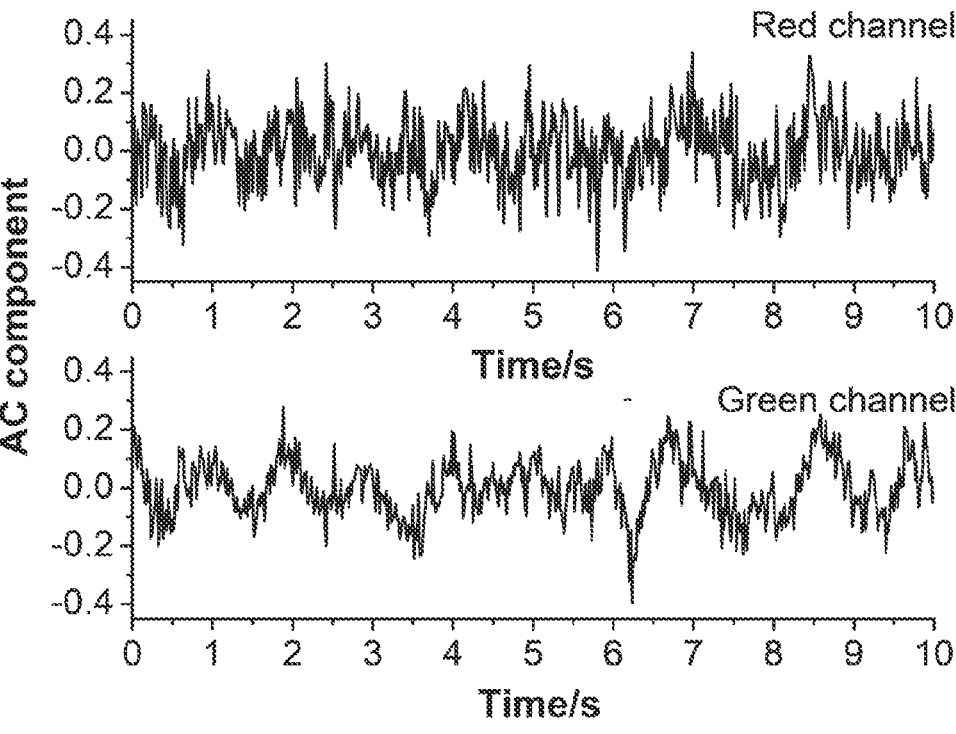
FIG. 3D is a graph of the AC components of Red (top) and Green (bottom) channels, in accordance with the present technology.

FIGS. 3A-3D demonstrate the extraction process of iPPG signals from a video sequence recorded by the remote smartphone 100 at 60 fps. FIG. 3A is a video sequence is illustrated along the time axis where the region of interest (ROI) is marked with dotted line box for evaluation, in accordance with the present technology. FIG. 3B is a graph of the evolution of the spatially-averaged values within the ROI, in accordance with the present technology. The time series of reflectance signal, during the recorded video at Red (top) and Green (bottom) channels, respectively, is illus-trated. On the horizontal axis is the time in seconds. On the vertical axis is the average gray value in ROI. FIG. 3C is a graph of the Fourier spectra of the time series signal at the green channel, in accordance with the present technology. FIG. 3C clearly shows the heartbeat frequency around 1 Hz. Band-pass filter (gray-marked between 0.5~5 Hz). This frequency is employed to extract AC components from the time series reflectance signals. FIG. 3D is a graph of the AC components of Red (top) and Green (bottom) channels, in accordance with the present technology.

In the data processing to extract the time series of reflec-tance signals, an ROI was first selected in the video image, which covered most of the hand backside, as shown in FIG. 3(*a*). At each time frame, a mean value was obtained through averaging all the pixel values within the ROI at each color channel to provide the time varying reflectance signals, representing red, green and blue channels, respectively (as shown in FIG. 3B), where red and green channels are given). The time series of reflectance signals exhibited low-fre-quency respiration signal, high-frequency heartbeat signal and noises. The fast Fourier transform (FFT) result of the signal from Green channel in FIG. 3B is shown in FIG. 3C, where the heartbeat frequency around 1 Hz is clearly con-trasted. A band-pass filter with a passband between the physiologically relevant frequency band of [0.5-5 Hz] was employed to acquire AC components (FIG. 2D). Similarly, the DC components were computed by passing time-traced signals through a low-pass filter with a cutoff frequency of 0.3 Hz. At this point, the ratio of ratios between red and green channels can then be calculated using Eq. (6).

To estimate the mean gray values from each RGB channel in Eq. (10) or Eq. (11), the 2-second videos were volume-averaged within the ROI to represent the reflectance values at the skin surface recorded by the red-, green- and blue-array sensors in the built-in smartphone camera 200 when illuminated by the flashlight 300.

To obtain the weighting coefficients of Eq. (15), about 50% of the datasets captured from the first 3 volunteers were randomly selected for the calibration process of the multiple linear regression algorithm. All the rest datasets were used to test and validate the algorithm to provide the SpO$_2$ readings through comparing these readings with those pro-vided by the pulse oximeter using the Bland and Altman method. The total numbers of datasets used for training and cross-validation are also given in Table 2 for information. Note that the datasets from the volunteers 4 and 5 were not participated in the training.

Figure 4A:
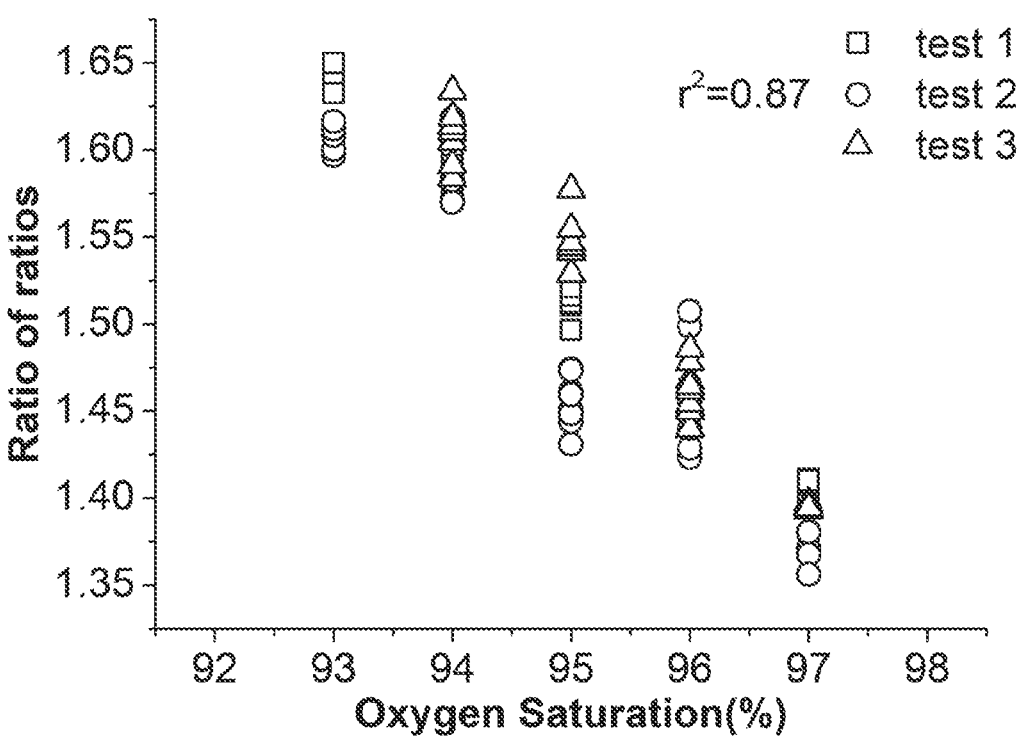
FIG. 4A is a graph of the relationship between the reference $SpO_2$ and the calculated ratio of ratios of a volunteer, in accordance with the present technology.
Figure 4B:
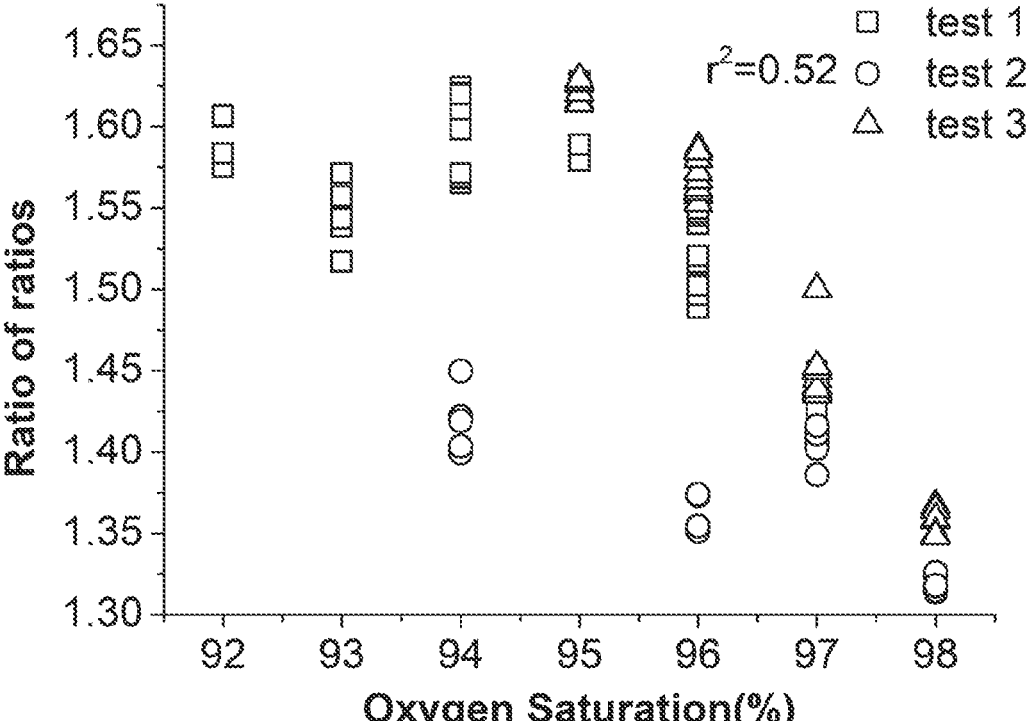
FIG. 4B is a graph of the relationship between the reference $SpO_2$ and the calculated ratio of ratios of another volunteer, in accordance with the present technology.

FIG. 4A-4B show the relationship between the reference $SpO_2$ and the calculated ratio of ratios. FIG. 4A is a graph of the relationship between the reference $SpO_2$ and the calculated ratio of ratios of a volunteer, in accordance with the present technology. FIG. 4B is a graph of the relationship between the reference $SpO_2$ and the calculated ratio of ratios of another volunteer, in accordance with the present technology. Results were obtained from three repeated trial tests: (FIG. 4A) volunteer 1, and (FIG. 4B) volunteer 2. The dependence of the ratio of ratios on the reference $SpO_2$ from two representative volunteers are shown in FIG. 4A-4B, where the data shown were from three repeated trials. As expected, the ratio of ratios increases gradually when the oxygen saturation is decreased. However, volunteer 1 (FIG. 4A) has better coefficient of determination (with r2=0.87) whereas volunteer 2 (FIG. 4B) presents worse correlation (with r2=0.52) between the ratio of ratios and the oxygen saturation. The relatively poor linearity shown in FIG. 4(b) may be caused by the variation of effective blood volume during data recording.

As discussed, the effective blood volume within the light interrogated tissue volume would directly impact the reflectance emerging at the tissue surface, represented as the change in the gray value of the images recorded by the smartphone camera 200. The relationships between the mean gray values from green, red and blue channels and the ratio of ratios were analyzed. The datasets from the first trial test shown in FIGS. 4A-4B were processed to show these relationships. The results of which are shown in FIGS. 5A-5D.

Figure 5A:
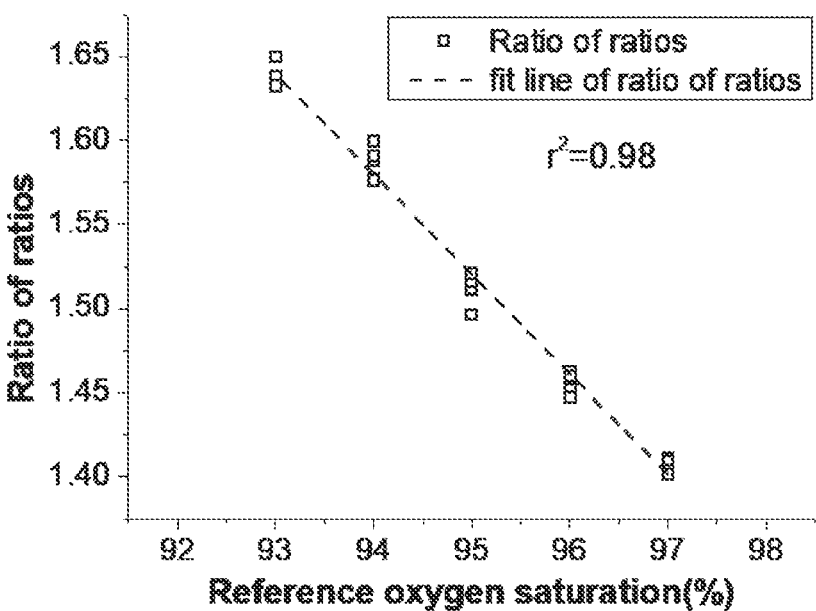
FIG. 5A is a graph of reference $SpO_2$ of a first volunteer, in accordance with the present technology.
Figure 5B:
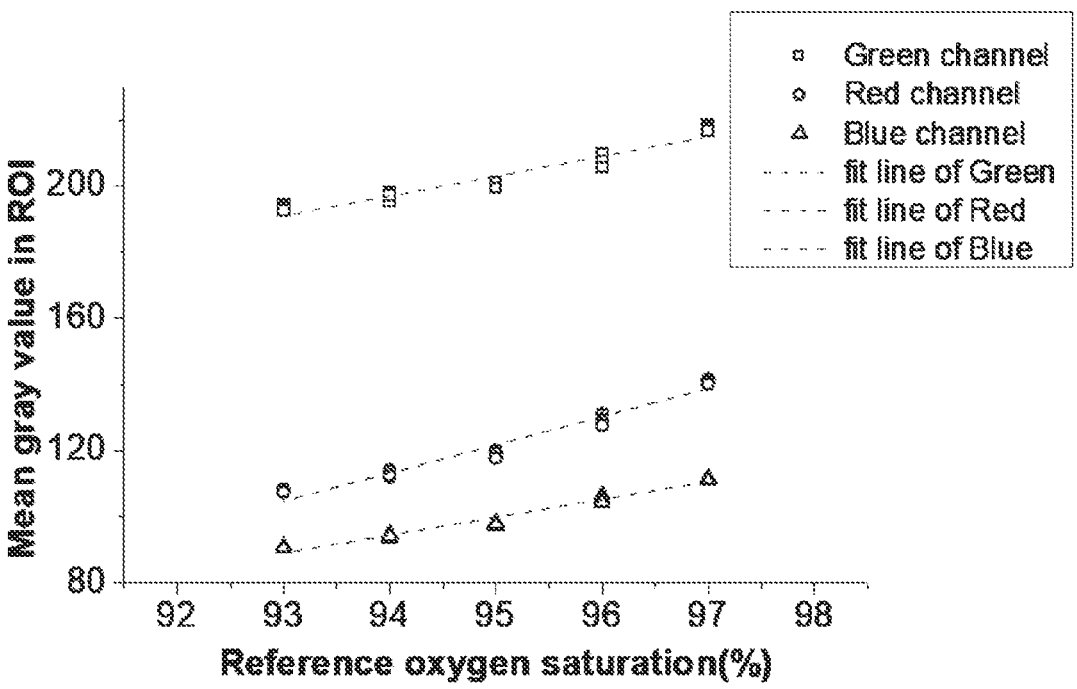
FIG. 5B is a change in the mean grey values of the first volunteer, in accordance with the present technology.
Figure 5C:
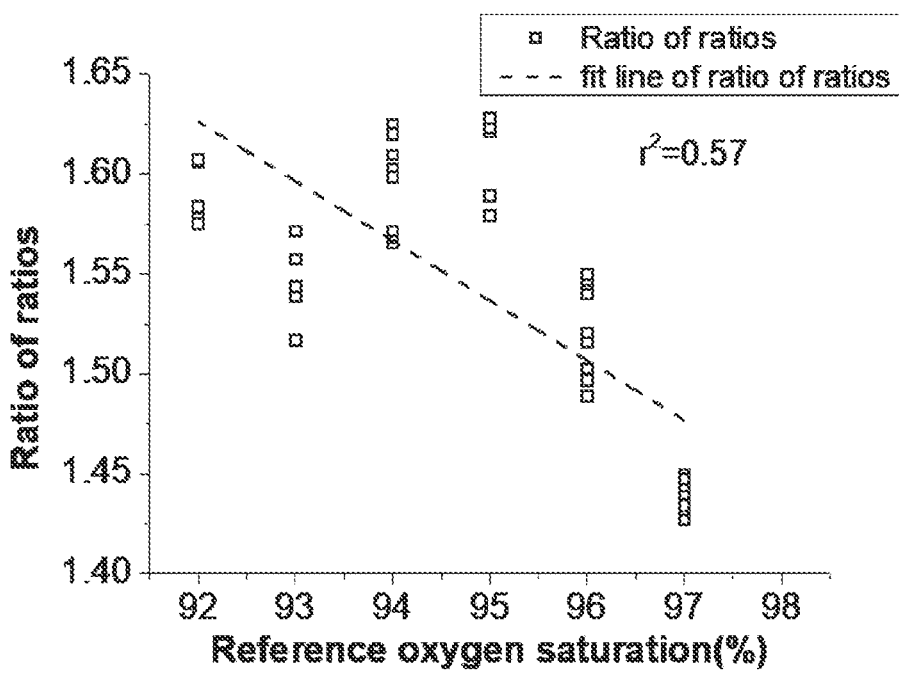
FIG. 5C is a graph of reference $SpO_2$ of a second volunteer, in accordance with the present technology.
Figure 5D:
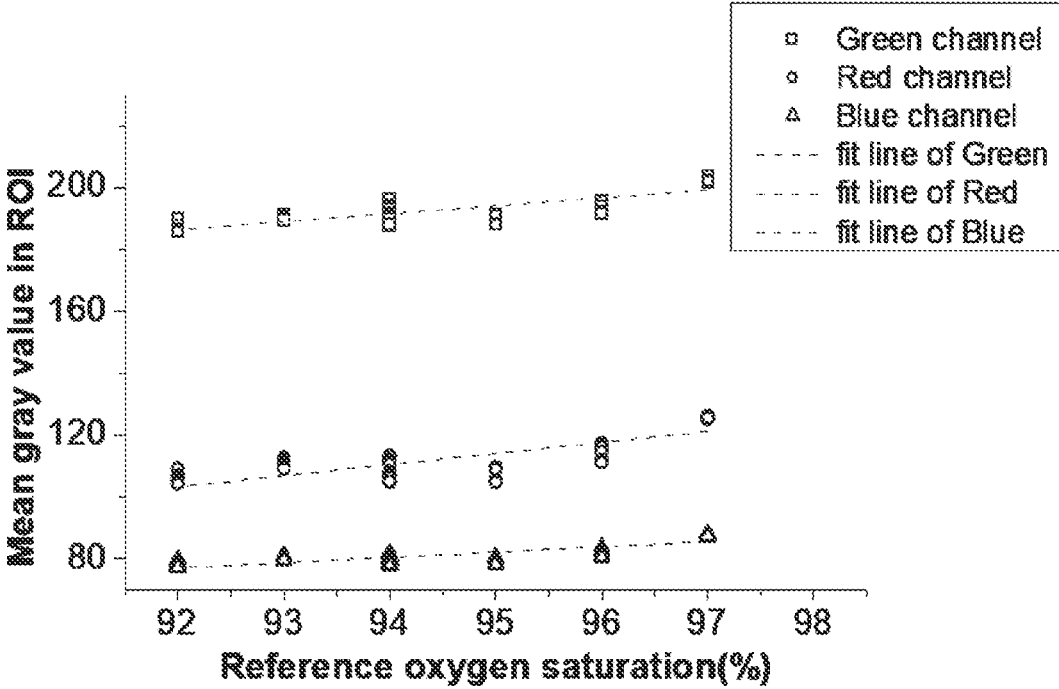
FIG. 5D is a change in the mean grey values of the second volunteer, in accordance with the present technology.

FIGS. 5A-5D show the relationship between the reference $SpO_2$ and the variables extracted from the smartphone recordings, in accordance with the present technology. The results shown are from the first trial test in FIGS. 4A-4B. Illustrated is the change in the ratio of ratios with the variation of the reference oxygen saturation. FIG. 5A is a graph of reference $SpO_2$ of a first volunteer, in accordance with the present technology. FIG. 5B is a change in the mean grey values of the first volunteer, in accordance with the present technology. FIG. 5C is a graph of reference $SpO_2$ of a second volunteer, in accordance with the present technology. FIG. 5D is a change in the mean grey values of the second volunteer, in accordance with the present technology. On the horizontal axis of FIGS. 5A-5D is the reference oxygen saturation in percentage. The dotted lines represent the linear fitting curves with r2 values as shown. FIGS. 5B and 5D show the changes in the mean gray values of green, red and blue channels with the variation of the reference oxygen saturation. Linear fitted lines of three channels are also shown with dotted lines. On the vertical axis is the mean gray value in the ROI. FIG. 5A and FIG. 5B were from volunteer 1. FIG. 5C and FIG. 5D were from volunteer 2.

The results from volunteer 1 presented an excellent coefficient of determination (r2=0.98) between the ratio of ratios and the reference oxygen saturation (FIG. 5A). The same volunteer also exhibited a good correlation between the mean gray values at the green, red and blue channels and the oxygen saturation, albeit with an opposite trend (FIG. 5B). However, a much variation in the results was seen in the volunteer 2 with a relatively poorer correlation between reference oxygen saturation and the ratio of ratios (r2=0.57) (FIG. 5C). While the linear relationships between the oxygen saturation and the mean gray values at the RGB channels exist (FIG. 5D), the coefficients of determination were relatively worse than that of volunteer 1. the coefficients of determination of the ratio of ratios, green channel, red channel and blue channel were tabulated from 4 trial tests in Table 3, where it was indicated that when the ratio of ratios presents a good coefficient of determination, the relationships between the $SpO_2$ and the mean gray values at the green, red and blue channels also show a good linearity, and vice versa.

TABLE 3

| Coefficients of determination resulted from linear fitting | | | | |
|---|---|---|---|---|
| Test number | 1 | 2 | 3 | 4 |
| Ratio of ratios | 0.98 | 0.85 | 0.57 | 0.48 |
| Green channel | 0.92 | 0.94 | 0.65 | 0.33 |
| Red Channel | 0.97 | 0.92 | 0.63 | 0.45 |
| Blue Channel | 0.97 | 0.89 | 0.64 | 0.36 |

After observing the behaviors of the extracted variables from the smartphone recordings with the change in the $SpO_2$, the improvement that the proposed MLR algorithm would provide to estimate the $SpO_2$ was tested and demonstrated. While there were more datasets available for training the MLR algorithm to obtain the needed weighting coefficients as expressed in Eq. 15, about 50% of valid datasets from the volunteers 1, 2 and 3 were randomly selected for the training and calibration. The rest of the datasets were used to cross-validate the MLR algorithm (See Table 2).

Figure 6A:
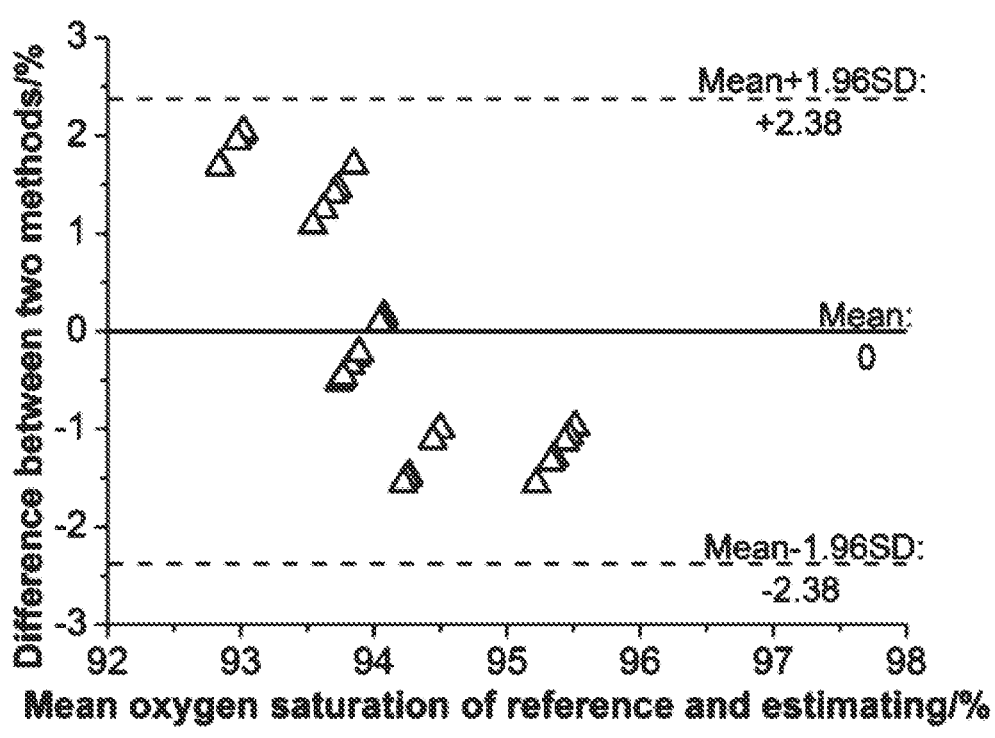
FIG. 6A is a graph of a Bland-Altman plot of estimated $SpO_2$ based on linear regression with the ratio of ratios method against the reference oximeter reading, in accordance with the present technology.
Figure 6B:
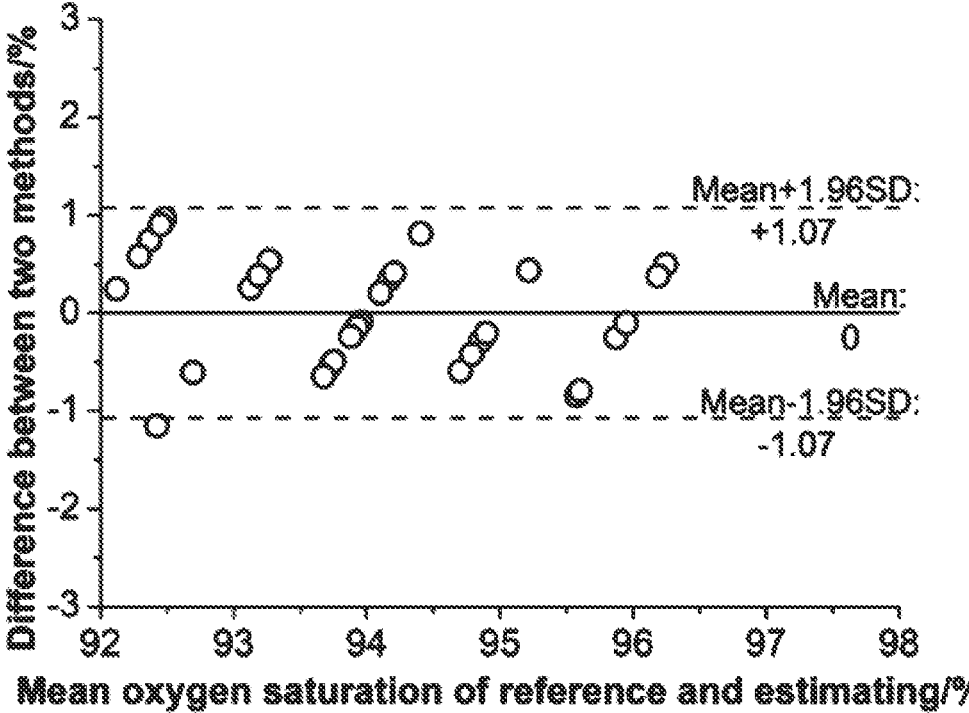
FIG. 6B is a graph of a Bland-Altman plot of estimated $SpO_2$ based on the MLR algorithm, in accordance with the present technology.

FIGS. 6A-6B are graphs of the test of the trained MLR algorithm on an intraclass scenario of Volunteer 2 against the reference oximeter readings. FIG. 6A is a graph of a Bland-Altman plot of estimated $SpO_2$ based on linear regression with the ratio of ratios method against the reference oximeter reading, in accordance with the present technology. On the horizontal axis is the mean oxygen saturation of reference and estimating in percentage. On the vertical axis is the difference between the two methods in percentage. The two dotted lines at either side of the mean line show $\mu \pm 1.96$ $\sigma=0\pm2.38$. FIG. 6B is a graph of a Bland-Altman plot of estimated $SpO_2$ based on the MLR algorithm, in accordance with the present technology. On the horizontal axis is the mean oxygen saturation of reference and estimating in percentage. On the vertical axis is the difference between the two methods in percentage. The two dotted lines at either side of the mean line show $\mu \pm 1.96$ $\sigma=0\pm1.07$.

After obtaining weighting coefficients from the training process, the MLR algorithm was tested for the volunteer 2 (i.e., intraclass testing because volunteer 2 was participated in the training). The Bland-Altman plots of the reference $SpO_2$ readings from the pulse oximeter and the estimated $SpO_2$ values from the ratio of ratios method and the proposed MLR method are shown in FIGS. 6A-6B. In this case, the measurement error of $SpO_2$ is $0\pm2.38\%$ ($\mu \pm 1.96$ $\sigma$) for the ratio of ratios method, showing a relatively big deviation relative to the reference oximeter (FIG. 6A). However, the accuracy of estimation based on MLR achieves $0\pm1.07\%$ (FIG. 6B), indicating an excellent 55% improvement compared to that of the ratio of ratios method.

Figure 7A:
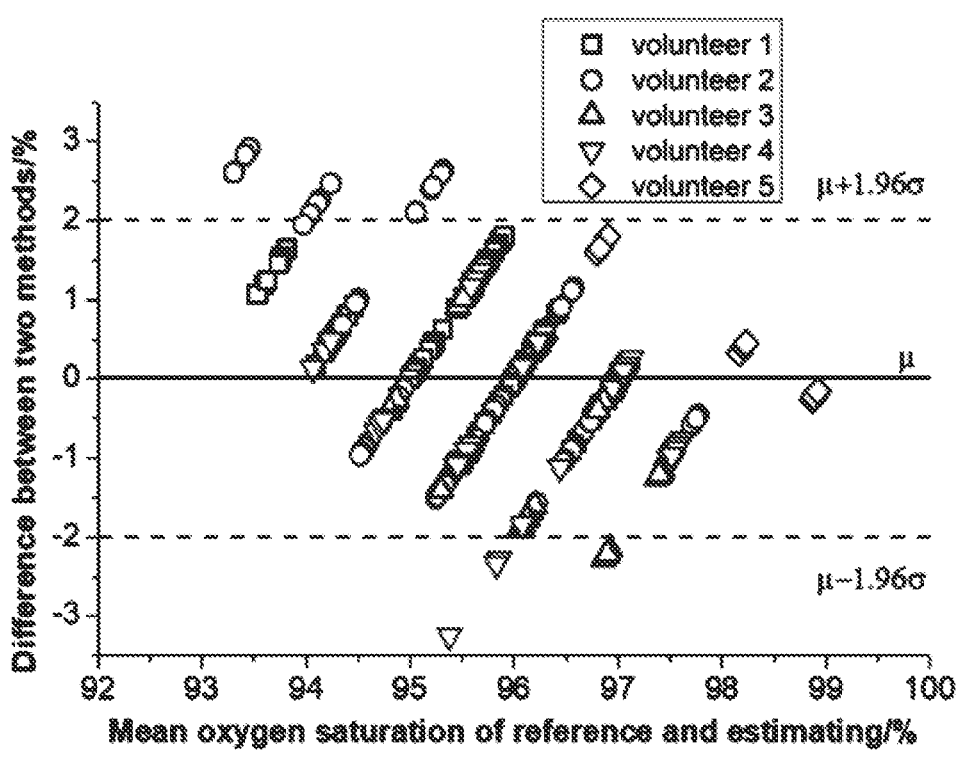
FIG. 7A is a graph of a Bland-Altman plot of estimated $SpO_2$ based on linear regression with the ratio of ratios method against the reference oximeter reading, in accordance with the present technology.
Figure 7B:
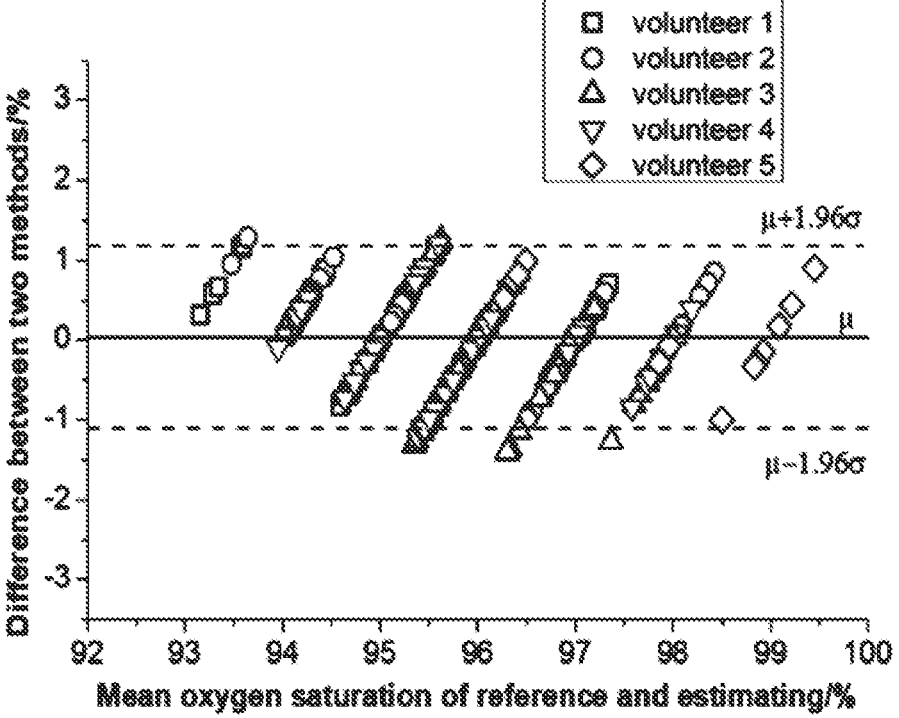
FIG. 7B is a Bland-Altman plot of estimated $SpO_2$ based on the MLR algorithm, in accordance with the present technology.

FIGS. 7A-7B show the test of the trained MLR algorithm on the datasets available from all the volunteers against the reference oximeter readings. FIG. 7A is a graph of a Bland-Altman plot of estimated $SpO_2$ based on linear regression with the ratio of ratios method against the reference oximeter reading, in accordance with the present technology. On the horizontal axis is the mean oxygen saturation of reference and estimating in percentage. On the vertical axis is the difference between the two methods in percentage. The two dotted lines at either side of the mean line ($\mu$) show $\mu \pm 1.96$ $\sigma = 0.008 \pm 2.008$. Each of the volunteers are shown with a series of shapes. FIG. 7B is a Bland-Altman plot of estimated $SpO_2$ based on the MLR algorithm, in accordance with the present technology. On the horizontal axis is the mean oxygen saturation of reference and estimating in percentage. On the vertical axis is the difference between the two methods in percentage. The two dotted lines at either side of the mean line ($\mu$) show $\mu \pm 1.96$ $\sigma = 0.008 \pm 2.008$. Each of the volunteers are shown with a series of shapes. The two dotted lines at either side of the mean line ($\mu$) show $\mu \pm 1.96$ $\sigma = 0.029 \pm 1.141$.

Next, the MLR algorithm was tested on the $SpO_2$ estimation on all the available validating datasets (Table 2), including those from the volunteers that were not included in the training. In this case, the cross-validation of leave-one-out technique was used. The resulted $SpO_2$ compared with those of reference oximeter are summarized, for the conventional ratio of ratios method (FIG. 7A) and the proposed MLR algorithm (FIG. 7B). The overall estimated error between the conventional ratio of ratios method and the reference oximeter was $\mu \pm 1.966 = 0.008 \pm 2.008\%$, whereas that for the MLR algorithm was $\mu \pm 1.96$ $\sigma = 0.029 \pm 1.141\%$, indicating a 43% improvement for the proposed method. A degradation in the performance was observed compared to the intraclass testing, probably because of the mixed skin colors across the volunteers.

The results presented herein show that compared to the conventional ratio of ratios method, the multiple linear regression (MLR) algorithm results in much better estimation of the $SpO_2$, delivering a very good agreement with the readings from a commercial medical grade pulse oximeter sensor. This improvement is attributed to the additional consideration of the changes in light scattering and absorption that are induced by the effective blood volume within the light interrogated skin tissue, giving rise to the changes in the reflectance images recorded at the RGB channels. It is noted that when dealing with the ratio of ratios method, some literature suggested to carefully select the regions of interest (ROI) by calculating signal-to-noise ratios for each ROI so that the best ROI was selected for improved estimation of the oxygenation saturation. Even with this complicated procedure, the ratio of ratios method still exhibits relatively poor coefficient of determination with oxygen saturation, affecting the accuracy of the final estimated $SpO_2$. In this study, it was found that the mean gray values from three RGB channels of smartphone camera 200 are correlated with the observed oxygen saturations. Taking these relationships as additional variables into the consideration for estimating $SpO_2$, the accuracy is demonstrated with great improvement using the proposed MLR algorithm. When compared to that of the ratio of ratios method, the measurement error for intraclass testing is reduced from $0 \pm 2.38$ ($\mu \pm 1.96$ $\sigma$) to $0 \pm 1.07$, indicating a ~55% improvement.

The overall improvement by including the volunteers not participated in the training is observed at 43%. The second advantage of the MLR method is a short sampling period. Non-contact detection of oxygen saturation has always required longer sampling time to acquire the datasets with good SNR. Most prior remote algorithms require 10~12 seconds sampling time. However, the sampling time-period of the proposed MLR algorithm in this paper was reduced to 2 seconds, which is similar to the fastest sampling time of commercial pulse oximeters. This merit is important because it could have great potential to improve the practicality of the non-contact smartphone-based approach to estimate the oxygen saturation in human subjects. Thirdly, because of the attributes of remote and non-contact measurement, the proposed MLR method delivers additional advantages of rapid survey and avoiding cross infection, which is particularly important for the current epidemic outbreak of COVID-19.

The reference standard used in this study was a commercial and medical grade pulse oximeter rather than blood-gas analysis. This could introduce possible errors when assessing the accuracy of this new algorithm because the algorithm relies on the absolute accuracy of the pulse oximeter. In some embodiments, the MLR algorithm can be calibrated with the gold standard blood-gas analysis for improved accuracy. On the other hand, the infrared light used in pulse oximeter has deeper penetration depth relative to the visible light employed in remote smartphone method. Therefore, the pulse oximeter provides the arterial oxygen saturation ($SaO_2$) measurement, whereas the remote smartphone method is more likely to measure the peripheral tissue oxygen saturation ($StO_2$). Although $SaO_2$ and $StO_2$ are correlated over limited ranges, no study has been conducted on humans so far. Large fluctuation on the ratio of ratios may be explained by the fact that, venous and capillary oxygen saturation would more likely be influenced by ambient variation relative to arterial oxygen saturation.

Considering the ever-growing utility of the smartphones in the community, mobile health (mHealth) is playing an increasingly important role in nowadays medical market, even for personal amusements. Heart/respiration rate monitoring, blood pressure surveillance, morphological features analysis and hemodynamics monitoring are all successful applications of mHealth to date. More opportunities of medical applications by leveraging the advances in the development of smartphones would help improve the medical environment in undeveloped areas, making it possible for remote monitoring of health conditions and realizing household health monitoring economically. Integration of accurate non-contact oxygen saturation measurement in the smartphone would thus accelerate the developments of mHealth.

The feasibility of using intact and unmodified smartphone to realize the remote measurement of peripheral oxygenation saturation ($SpO_2$) is disclosed herein. A multiple linear regression (MLR) algorithm has been proposed to accommodate the changes in light scattering and absorption due to the effective blood volume within the light interrogated skin tissue volume, for which the changes in the reflectance images recorded at RGB channels in the smartphone were used as a surrogate in the formulation of the algorithm. It has been shown that the proposed MLR algorithm delivers a significant improvement (55% improvement for intraclass testing, and 43% for overall testing) in the estimation of $SpO_2$ when compared with that of the conventional ratio of ratios method. In some embodiments, the RGB camera is on a communication device. Since the results were demonstrated with the built-in color camera and the built-in flashlight within a smartphone with a sampling time duration similar to the standard pulse oximeter, this development represents a significant advance to the current effort for developing accessible and cost-effective mHealth, particularly benefiting the populations living in the underserved and rural areas and in the developing countries.

EXAMPLE #2

Figure 8A:
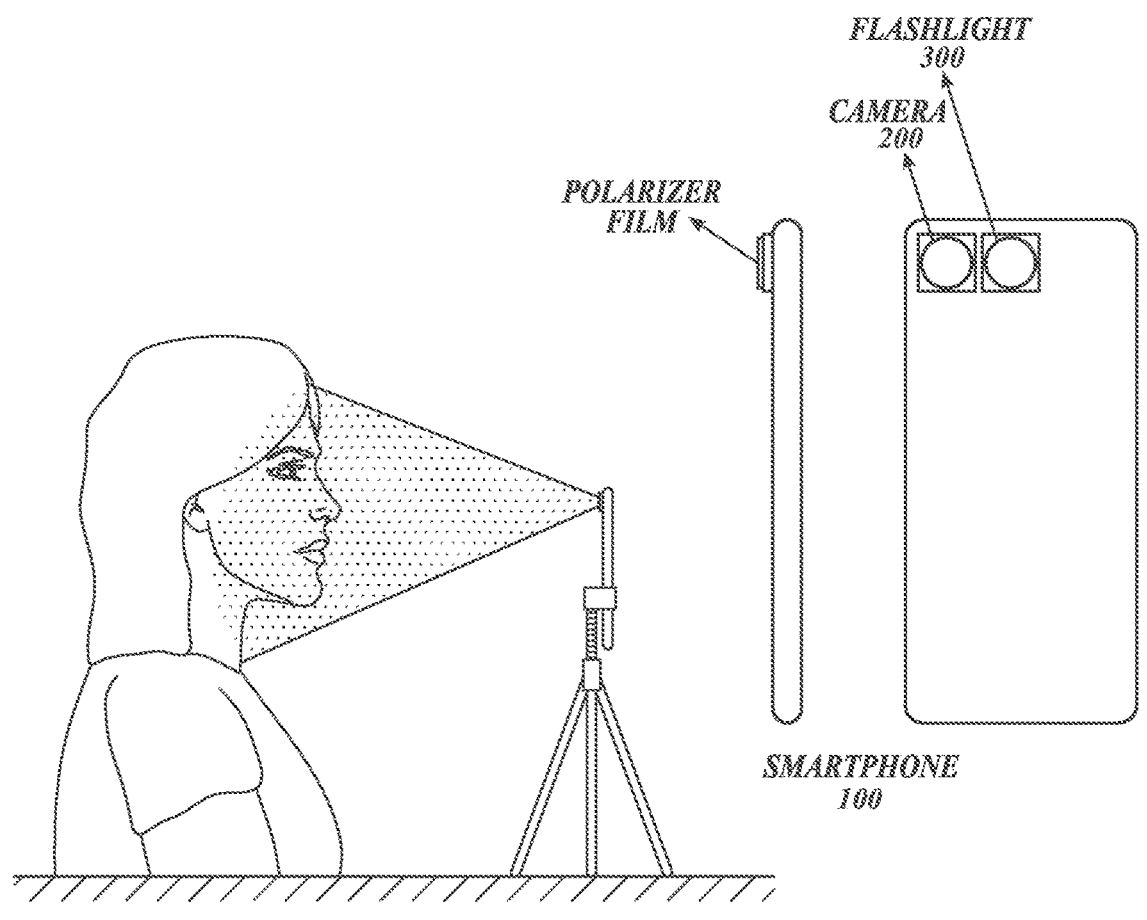
FIG. 8A is a schematic of the smartphone remote PPG (SP-rmPPG) system setup for video recording of the subject, in accordance with the present technology.
Figure 8B:
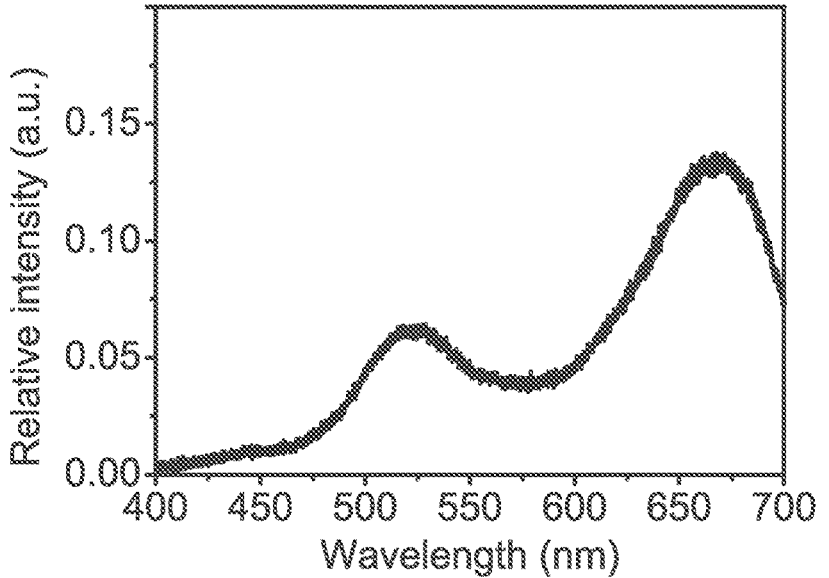
FIG. 8B is a spectral power distribution of the built-in flashlight in an example smartphone, in accordance with the present technology.
Figure 8C:
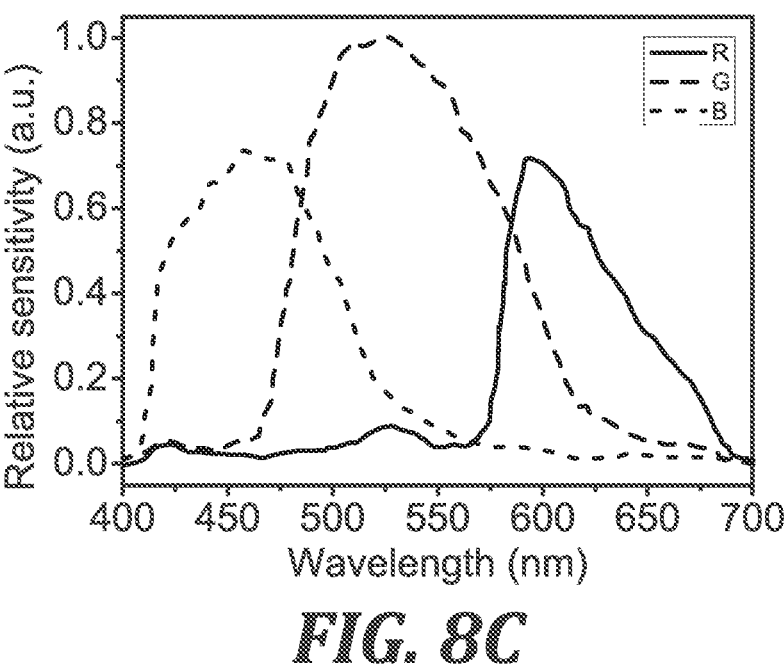
FIG. 8C is a spectral sensitivity of R, G and B channels of the smartphone camera used to record videos, in accordance with the present technology.
Figure 8D:
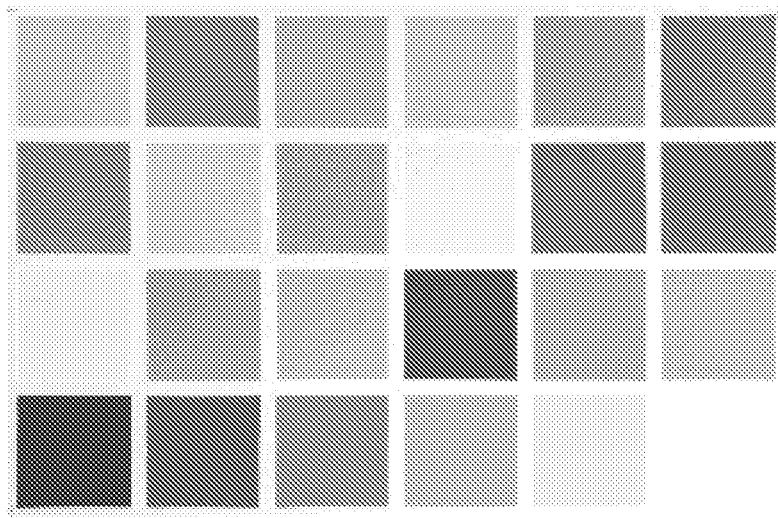
FIG. 8D is a gray-scale photograph of the standard color checker used to calibrate the smartphone for multispectral imaging, in accordance with the present technology.

FIG. 8A is a schematic of the smartphone 100 remote PPG (SP-rmPPG) system setup for video recording of the subject, in accordance with the present technology. FIG. 8B Spectral power distribution of the built-in flashlight 300 in an example smartphone, in accordance with the present technology. An iPhone 8, Apple Inc, USA was used to produce the graph in FIG. 8B, but any smartphone may be used. On the horizontal axis is the wavelength in nanometers. On the vertical axis is the relative intensity in arbitrary units. FIG. 8C is a spectral sensitivity of R, G and B channels of the smartphone camera 200 used to record videos, in accordance with the present technology. On the horizontal axis is the wavelength in nanometers. On the vertical axis is the relative sensitivity in arbitrary units. FIG. 8D is a gray-scale photograph of the standard color checker used to calibrate the smartphone for multispectral imaging, in accordance with the present technology. To verify the accuracy, the derived transformation matrix was applied on the RGB-mode image of the color checker to calculate its reconstructed reflectance data at multiple wavelengths of interest.

Set up and data recording Schematic of the experimental setup to demonstrate the proposed SP-rmPPG method is illustrated in FIG. 8A, where an unmodified smartphone was used to acquire video images of dynamic light reflectance emerging at the skin surface upon which to derive blood oxygenation and hemodynamics. In this study, an iPhone 8 (Apple, USA) was used for the demonstration purpose, but any types of smartphones can be used. The videos were collected by the smartphone rear camera under illumination from the built-in flashlight. The spectral power distribution of the flashlight is shown in FIG. 8B. The relative spectral sensitivities of the R, G and B channels in the smartphone camera 200 are given in FIG. 8C. A polarizer film was placed in front of the flashlight and an analyzer film in front of the camera lens. The film pairs were arranged orthogonally to minimize specular reflections from the skin surface. The illumination uniformity in the field of view (FOV) was tested with a standard 95% reflection board. U1 (Minimum/Average lux) and U2 (Minimum/Maximum lux) were assessed to be 0.99 and 0.92, respectively, indicating that the illumination is relatively uniform across the sample target. The room temperature was kept at around 23° C. and the humidity was around 50% during the experiments of video recording. Before recording the video, the volunteer was allowed to calmly sit in a chair for 5 minutes to get acquainted to the room environment and stabilize the heartbeat.

The smartphone was placed 30 cm away from the skin surface. In some embodiments, the one or more images is a video. In the smartphone, "ProMovie" from the App Store was installed and used it to acquire videos, representing the light reflectance emerging at the skin surface. In some embodiments, any form of video capture application or technology can be used. The image resolution was set at 2160×3840 pixels. The shutter speed, ISO and white balance were set to be $\frac{1}{60}$ seconds, 100 and 4000K, respectively. Normal healthy volunteers were enrolled in this study to demonstrate the feasibility of proposed methods. This study adhered to the tenets of the Declaration of Helsinki and was performed in accordance with the Health Insurance Portability and Accountability Act. Informed consent was obtained from the subjects prior to the start of each study session. Ethical approval was obtained from the Institutional Review Board of the University of Washington.

In some embodiments, the method further comprises calibrating the RGB camera with a Weiner estimation method and a color-checker. A Wiener estimation method was applied to calibrate the built-in RGB-mode camera in the smartphone to perform multispectral imaging. Briefly, a standard color checker (X-Rite ColorChecker Classic, FIG. 8D) was used in this study to calibrate the smartphone camera 200, where the images (or video) captured from the standard color checker were used as the training data set to determine a transformation matrix that is needed to convert the RGB color images into the multispectral images. Under the illumination provided by the built-in flashlight, the transformation matrix can be determined by the following equation:

$$W = \langle V'Vt \rangle \langle VVt \rangle^{-1} \tag{16}$$

where W is the reconstructed transformation matrix. $\langle \ \rangle$ is an ensemble-averaging operator. V'Vt is the correlation matrix between the multispectral reflectance of the color checker and the RGB responses in the smartphone camera 200.

The standard reflectance data of the color checker was provided by the manufacturer. In some embodiments, the multispectral data cube 500 represents spectral information at wavelengths of 450, 500, 550, 600, 650 and 700 nm. Here, 450, 500, 550, 600, 650 and 700 nm were selected as the wavelengths of interest in the calibration, though other wavelengths can be selected if needed. VVt is the autocorrelation matrix of the RGB sensor responses in the camera.

FIGS. 9A-9D shows the comparison between the standard reflectance and the reconstructed reflectance from the transformation matrix for each block in the color checker, in accordance with the present technology. In FIGS. 9A-9D, SR is the standard reflectance, and RR reconstructed reflectance. The comparison of standard and reconstructed reflectance data is shown in FIGS. 9A-9D. In addition, the goodness of fit coefficients (GFC) between the standard and reconstructed reflectance data was evaluated and labeled in the corresponding blocks in FIG. 9A-9D. The minimum, average and maximum GFC values were measured to be 0.9533, 0.9898 and 0.9999, indicating that the derived transformation matrix is accurate enough to estimate the real reflectance of the targets from their RGB-mode images.

Figures 9A, 9B:
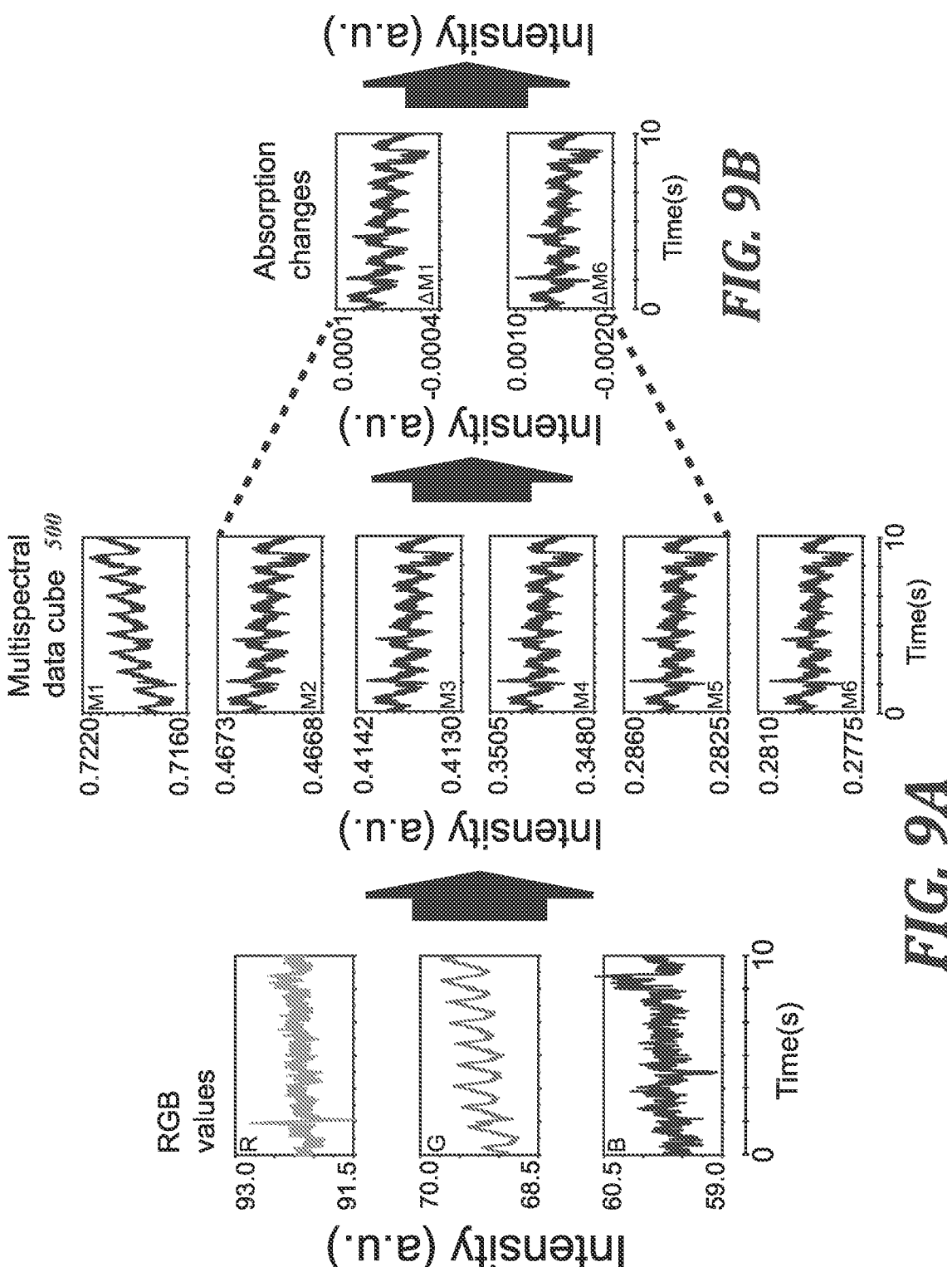
FIGS. 9A-9D show the comparison between the standard reflectance and the reconstructed reflectance from the transformation matrix for each block in the color checker, in accordance with the present technology.
Figures 9C, 9D:
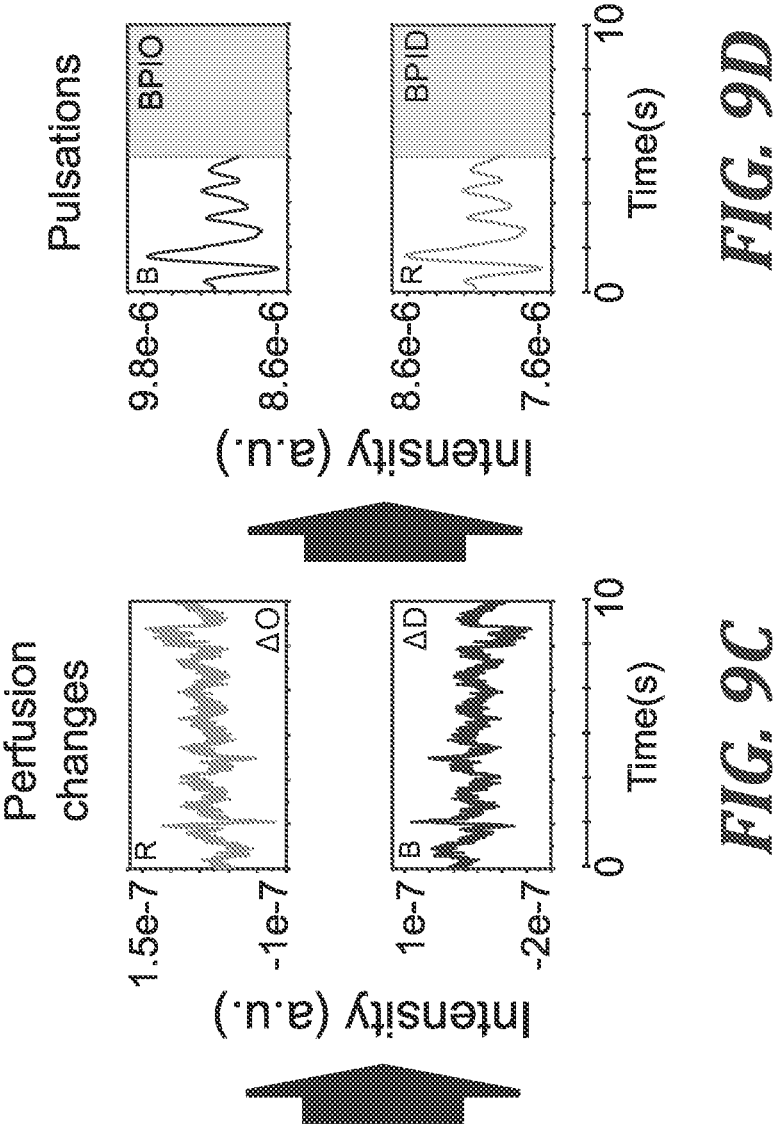

With the transformation matrix W obtained, the RGB-mode videos of the skin can then be converted into multispectral data cubes 500, as shown in FIG. 9A. The multispectral cube 500 thus obtained represents the spectral information at the six wavelengths of 450, 500, 550, 600, 650 and 700 nm, which can be written as:

$$\begin{bmatrix} M_1(x, y, t) \\ M_2(x, y, t) \\ \ldots \\ M_6(x, y, t) \end{bmatrix} = W \times \begin{bmatrix} R(x, y, t) \\ G(x, y, t) \\ B(x, y, t) \end{bmatrix} \tag{17}$$

where $M_i(x, y, t)$ is the reconstructed spectral value at pixel (x, y) and time t. i is the channel number (i=1, 2, ..., 6, representing 450, 500, 550, 600, 650 and 700 nm, respectively). R(x, y, t), G(x, y, t) and B(x, y, t) are the values at the pixel (x, y) and time t of the video from the red, green, and blue channels, respectively.

Numeric values shown in each block are the goodness of fit coefficients between SR and RR. Since extracting $HbO_2$ and Hb information was the goal in the dynamic blood perfusion, the wavelength selection could follow the requirements of pulse oximetry. That is, the absorption coefficients of $HbO_2$ and Hb should be approximately equal at one wavelength and differ considerably at another wavelength. Therefore, channel 2 was selected (500 nm, approximately at the isosbestic point) and channel 5 (650 nm, having considerable difference in absorption between $HbO_2$ and Hb) as the target wavelengths in further processing steps to derive oxygenation information, as shown in FIG. 9B. For the reconstructed signals at each channel, it was estimated the changes in light absorption with reference to the time zero by using the modified Beer-Lambert law, i.e., $$\Delta A = At - A0 = -\log (I_t/I_s) - (-\log (I_0/I_s)) = -\log (I_t/I_0) \quad (18)$$

where $\Delta A$ is the change in light absorption from the time t0 to t. At and A0 are the light absorbance at the time t and t0. It and I0 are the signal intensities in selected channels at the time t and t0. Is is the intensity of incident light. Assume that the light absorption in the skin is caused by melanin, $HbO_2$ and Hb chromophores. In the current study, it can safely be assumed the melanin concentration is constant over time. Thus, the change in light absorption (Eq. 19) would be dominated by the changes in $HbO_2$ and Hb concentrations within the blood volume. Consequently, Eq. 19 could be rewritten as:

$$\Delta A = \Delta c^{HbO2} \epsilon^{HbO2} l + \Delta c^{Hb} \epsilon_{Hb} l \quad (19)$$

where $\Delta c$ is the change in either $HbO_2$ or Hb concentrations. $\epsilon$ is the absorption extinction coefficient of either $HbO_2$ or Hb. l is the light interaction path length. It is assumed that the light interaction path lengths at different wavelengths to be the same. In order to decouple the changes in $HbO_2$ and Hb in Eq. 20, a weighting formula was constructed, below:

$$\Delta = \Delta A_2 - k\Delta A_5 = \Delta c^{HbO2} l \left( \varepsilon_2^{HbO2} - k\varepsilon_5^{HbO2} \right) + \Delta c^{Hb} l \left( \varepsilon_2^{Hb} - k\varepsilon_5^{Hb} \right) \quad (20)$$

where $\Delta$ is the result after weighted subtraction. $\Delta A2$ and $\Delta A5$ are the changes in the light absorbance at 500 nm and 650 nm, respectively. k is the subtraction weighting factor to be determined.

$$\varepsilon_2^{HbO2}, \varepsilon_5^{HbO2}, \varepsilon_2^{Hb} \text{ and } \varepsilon_5^{Hb}$$

are the absorption extinction coefficients of $HbO_2$ and Hb at 500 nm and 650 nm, respectively. It is clear that if the factor k is set to be $$\varepsilon_2^{Hb} \varepsilon_5^{Hb},$$

then the effect of the Hb changes on Eq. 20 would be eliminated. Thus, the change in $HbO_2$ concentration can be derived as:

$$\Delta c^{HbO2} = \frac{\Delta A_2 - k\Delta A_5}{l\left( \varepsilon_2^{HbO2} - k\varepsilon_2^{HbO2} \right)} \left( \text{where } k = \varepsilon_2^{HbO2} / \varepsilon_5^{Hbo2} \right) \quad (21)$$

Likewise, if the factor k is set to $\epsilon2HbO2\epsilon5HbO2/$, then the effect of the $HbO_2$ changes on Eq. 20 is eliminated. Thus:

$$\Delta c^{Hb} = \frac{\Delta A_2 - k\Delta A_5}{l\left( \varepsilon_2^{Hb} - k\varepsilon_5^{Hb} \right)} \left( \text{where } k = \varepsilon_2^{HbO2} / \varepsilon_5^{HbO2} \right) \quad (22)$$

Thus far, the effects of the changes in $HbO_2$ and Hb concentrations on the Eq. 18 that can be estimated from the color images captured over time by the smartphone after multispectral conversion have been decoupled (Eq. 17). In doing so at each pixel in the video image, the spatiotemporal changes of decoupled $HbO_2$ and Hb concentrations (i.e., $\Delta c^{HbO^2}$ and $\Delta c^{Hb}$) within the dynamic blood perfusion within the light interrogated tissue volume can be obtained but scaled by the light interaction path length. For simplicity, it is assumed that the light interaction path length for $HbO_2$ and Hb is constant and takes a value of 1 mm.

It is known that heart pumping leads to pulsatile blood volume propagating throughout the body tissue. This pulsatile modulation of the blood volume results in the absorption modulation of the light propagating within the skin, which in turn leads to the intensity modulation of light reflected from the skin tissue. Assuming that the oxygenated and deoxygenated bloods are responsible for this absorption, the derived spatiotemporal changes in $HbO_2$ and Hb concentrations would also behave pulsatile, which can be used to analyze and indicate the blood volume pulsations within the light interrogated skin tissue volume in this study. In some embodiments, the blood measurement is a set of blood pulsation amplitudes, a set of blood pulsation phases, or both. In some embodiments, obtaining the set of blood pulsation amplitudes further comprises applying a window-based lock-in amplification to the oxygenated blood information and the deoxygenated blood information. To recover spatiotemporal pulsation of the dynamic blood perfusion, a window-based lock-in amplification algorithm was applied on the time varying $HbO_2$ and Hb signals obtained by Eq. (21) and Eq. (22). First, a 5-second time window was selected starting from the first frame. In the window, a standard function with its temporal heart rate frequency was built. The heart rate was extracted by conducting fast Fourier transformation of the global perfusion data in the window. The standard function can be expressed as:

$$R(t) = \cos(\omega_h t) - i \sin(\omega_h t) = e^{-i\omega_h t} \quad (23)$$

where R(t) is the standard reference function constructed by the known heart beating frequency $\omega h$. The dynamic blood perfusion signal at each pixel (x, y) obtained from the last Section can be expressed through Fourier series expansion:

$$\Delta c(x, y, t) = \sum_m \sum_n AM_{mn}(x, y)\cos[\omega_m t + \theta_n(x, y)] =$$

$$\sum_m \sum_n \frac{AM_{mn}(x, y)}{2} \left\{ e^{i[\omega_m t + \theta_n(x,y)]} + e^{-i[\omega_m t + \theta_n(x,y)]} \right\} \quad (24)$$

where $\Delta c(x, y, t)$ is the input signal representing the changes in hemoglobin concentration contained in the dynamic blood volume at time t. $AMmn(x, y)$, $\omega m$ and $\theta n(x, y)$ are the amplitude, frequency and phase of the input signal at the pixel (x, y). Therefore, the signals solely due to the heartbeat at the frequency $\omega h$ embedded within $\Delta c(x, y, t)$ can be recovered by applying lock-in detection:

$$Z(x, y) = \sum_t R(t)\Delta c(x, y, t) =$$

$$\sum_t \sum_m \sum_n \frac{AM_{mn}(x, y)}{2} \left\{ e^{i[\omega_m t + \theta_n(x,y)]} + e^{-i[\omega_m t + \theta_n(x,y)]} \right\} \quad (25)$$

where Z(x, y) is the time integral of the product of the standard reference function R(t) and the input signal of $\Delta c(x,$ y, t). Per lock-in detection mechanism, when the components of input signals have the frequencies that differ from the standard reference frequency (i.e., ωh), the product would oscillate in time and approach to zero. However, when the signal is of the same frequency as ωh, the product would be retained and amplified. Assuming the phase of the heart cycle at pixel (x, y) is constant over time, the output of the lock-in detection can be simplified as:

$$Z(x, y) = \frac{AM_h(x, y)}{2} e^{i\theta} h(x, y) \tag{26}$$

where $AM_h(x, y)$ and $\theta_h(x, y)$ are the amplitude and phase of the extracted cardiac pulsation signal, respectively. Consequently, the pulsation amplitude at pixel (x, y) can be calculated as below:

$$AM_h(x, y) = 2\text{abs}[Z(x, y)] = 2\text{abs}\left[\sum_t R(t)\Delta c(x, y, t)\right] \tag{27}$$

By moving the evaluating time window along the time axis across the entire video frames, the spatial and time-resolved pulsation of blood perfusion within the light interrogated skin tissue volume can be obtained. Since the dynamic blood contains oxygenated and deoxygenated blood, the pulsation amplitudes separately evaluated from the $HbO_2$ and Hb signals (i.e., Eq. (21) or Eq. (22)) must be equal and the same as the pulsation amplitude of the whole blood volume.

Figure 10A:
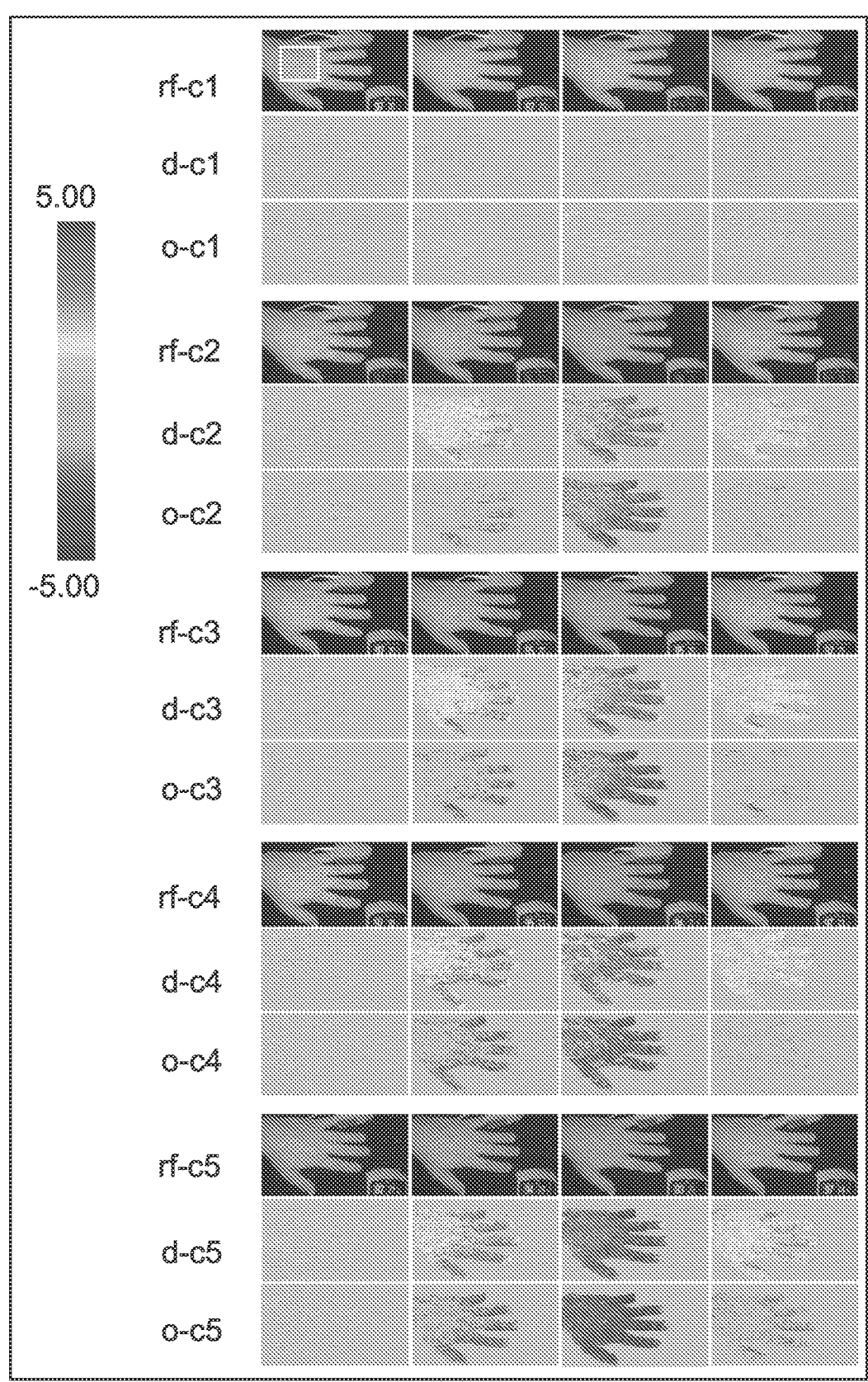
FIG. 10A is a RGB color video, in accordance with the present technology.
Figure 10B:
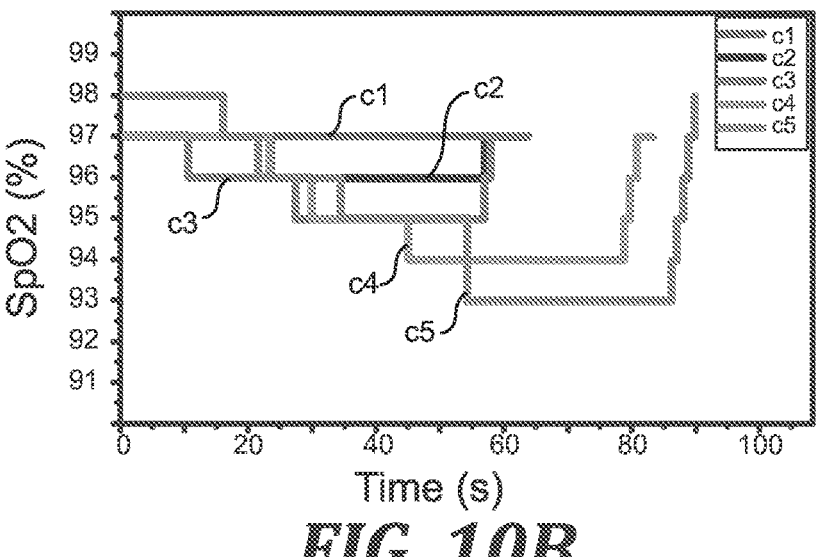
FIG. 10B is the time-varying spectral signals of selected wavelengths, in accordance with the present technology.
Figure 10C:
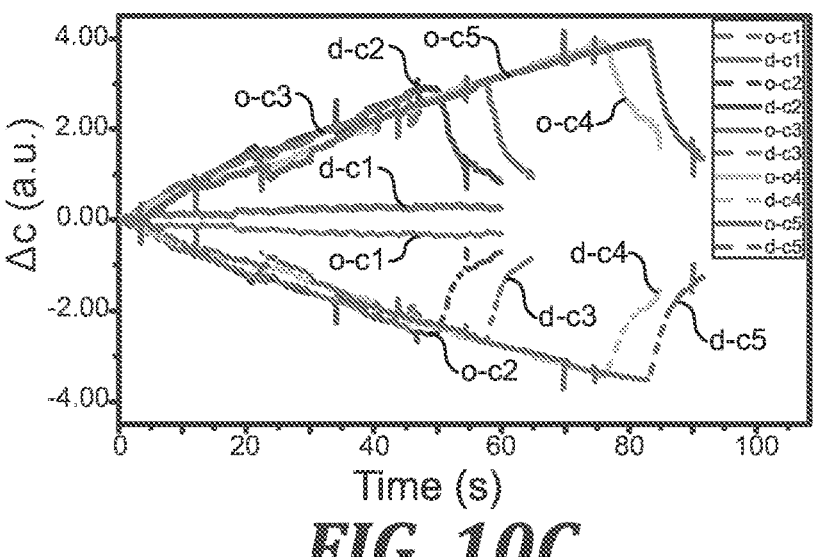
FIG. 10C shows the spatiotemporal changes in the $HbO_2$ and Hb concentrations in the blood volume within the light interrogated tissue volume, in accordance with the present technology.
Figure 10D:
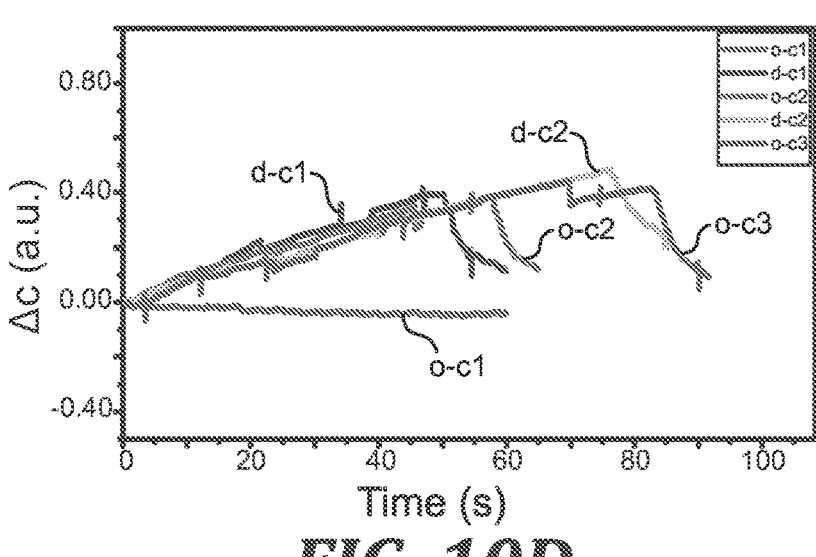
FIG. 10D shows an evaluated spatial pulsation amplitude, in accordance with the present technology.

FIGS. 10A-10D show the SP-rmPPG, which can provide information about spatiotemporal changes in oxygenated and deoxygenated blood within the light interrogated dorsal skin tissue in the hand during a routine blood cuff procedure applied on the upper arm. The changes in $HbO_2$ and Hb concentrations were estimated from the smartphone recorded videos of a volunteer's hand when the upper arm was applied with a pressure by the cuff, using the proposed SP-rmPPG algorithms. The results shown were obtained from 5 experimental trials: c1—0 mmHg/97% (control), c2—50 mmHg/96%, c3—70 mmHg/95%, c4—90 mmHg/94%, c5—110 mmHg/93%. FIG. 10A is an image of the representative reflectance, in accordance with the present technology. In FIG. 10A, the representative reflectance (rf), Hb (d) and $HbO_2$ (o) images are extracted from the spatiotemporal images at four-time instants: 1) the onset of the application of pressure cuff on the upper arm, 2) the time instant at the halfway of the video recording, 3) the time instant when the pressure cuff was released, and 4) the finishing time of the video recording. FIG. 10B is the time trace of measured oxygen saturation values from the pulse oximeter, in accordance with the present technology. FIG. 10C is the time traces of averaged values of decoupled $HbO_2$ and Hb changes within the selected ROI, in accordance with the present technology. The ROI is shown in the top left figure in FIG. 10A. FIG. 10D is multiple time traces of averaged values of the total hemoglobin changes within the selected ROI, in accordance with the present technology. In FIG. 10D, rf is the reflectance image, o is oxygenated blood, and d is deoxygenated blood.

FIGS. 10A-10D are schematics of signal processing steps to derive the spatiotemporal changes in $HbO_2$ and Hb and their pulsation amplitudes from the video images captured by the smartphone. FIG. 10A is a RGB color video. The RGB color video is first converted to hyperspectral video cube, where hyperspectral cube contains 6 wavelengths of 450, 500, 550, 600, 650 and 700 nm in this study. FIG. 10B is the time-varying spectral signals of selected wavelengths. The wavelengths shown are at 500 nm and 650 nm and are used to calculate the spatiotemporal changes in the $HbO_2$ and Hb. FIG. 10C shows the spatiotemporal changes in the $HbO_2$ and Hb concentrations in the blood volume within the light interrogated tissue volume. FIG. 10D shows an evaluated spatial pulsation amplitude, in accordance with the present technology. The spatial pulsation amplitude is taken from either dynamic $HbO_2$ or Hb signals resulted in from FIG. 10C.

A flow chart for the signal processing procedures described above is given in FIGS. 9A-9D. After the videos are captured by the smartphone, the time trace of signals in the RGB channels are first converted into the multispectral data cube 500 through the transformation matrix obtained by calibration (Eq. 17). The RGB colors were converted into the six spectral wavelengths at 450, 500, 550, 600, 650 and 700 nm, respectively. Then, the changes in light absorbance at 500 and 650 nm were calculated (Eq. 18) with reference to the frame at the time zero (i.e., the start of video frame of interest). Afterwards, the spatiotemporal changes in $HbO_2$ and Hb concentrations within the dynamic blood volume are decoupled by weighted subtraction method (Eq. 21 and Eq. 22). Finally, the spatiotemporal pulsation is mapped by the window-based lock-in detection mechanism (Eq. 25 and Eq. 26).

Having described the methods and formulations of SP-rmPPG to monitor the changes in $HbO_2$ and Hb concentrations and pulsatile blood volume in the light interrogated skin tissue from smartphone recorded videos, two experiments were conducted to demonstrate its feasibility to reveal oxygenation and pulsation changes during flow-challenged conditions. The first experiment was designed around the popular blood cuff maneuver at the upper arm to gradually occlude the blood draining venules. The second experiment was designed to simulate the occlusive external carotid artery (or more precisely the facial artery) that supplies the facial skin tissue beds.

In the 1st experiment (Experiment I), a standard medical grade manual blood cuff was applied to condition the blood supply and drainage in the left upper arm, and then used the SP-rmPPG system to monitor the development and evolution of blood hemodynamics in the dorsal skin of the left hand. Videos were taken by the smartphone while the cuff pressure was being applied. In parallel, a medical grade contact-mode sensor-based pulse oximeter (PC-66H Handheld Pulse Oximeter, CMI Health, USA) was used to monitor the peripheral oxygen saturation ($SaO_2$) at the left little finger. Five trials of the experiments were conducted by applying 0 (control), 50, 70, 90 and 110 mmHg cuff pressures on the upper arm until the $SaO_2$ as measured by the pulse oximeter reached a level of 97% (control), 96%, 95%, 94% and 93%, respectively. For each experimental trial, the video recording was started at the time when the cuff pressure was applied. After the target $SaO_2$ level was reached as monitored by the pulse meter and stabilized for 20 seconds, the cuff pressure was released and the video continued recording for next 10 seconds. These five trials were labeled as: c1—0 mmHg/97% (control), c2—50 mmHg/96%, c3—70 mmHg/95%, c4—90 mmHg/94%, c5—110 mmHg/93%. For example, for the trial c5 (110 mmHg/93%), the cuff pressure applied was 110 mmHg. The onset of the continuous video recording was at the time when the cuff pressure started at the upper arm. The cuff pressure was continuously being applied until the $SaO_2$ value measured by the pulse oximeter reached at the level of 93%, at which time the pressure was released. And the video recording continued for another 10 seconds.

The 2nd experiment (Experiment II) was designed to demonstrate whether the smartphone system is able to observe the changes in blood oxygenation and associated blood pulse strength at the facial skin when the external carotid artery that supplies maxillofacial region is challenged. There are two branches of the facial arteries symmetrically located at the lower jaw region near neck, supplying the nutritive blood to the facial skin tissue beds. The partial occlusive (or ischemic) condition was simulated within the skin tissue beds by gently pressing on the facial artery while continuously recording the videos of the light reflectance emerging at the facial skin surface using the smartphone. Below are the brief procedures of the experiment. First, the volunteer used the finger-touching method to locate the artery position by feeling pulse below the jawbone. Then, the smartphone started to continuously record the skin videos, initially without applying finger pressure on the artery. Approximately 15 seconds after the onset of the video recording, the volunteer applied a gentle pressure to press the artery to produce partial occlusion on the artery to limit the blood supply to the corresponding facial skin tissue beds. The applied pressure lasted for 20 seconds and was then removed. The video recording was finally ended at the time when a period of 60 seconds was reached. Two separate experiments were conducted using this procedure on the facial artery located at both sides of lower jaws: first on the left, and then on the right. Another set of experiment was also conducted without applying the pressure on the artery, which was treated as the control.

Figures 11A, 11B:
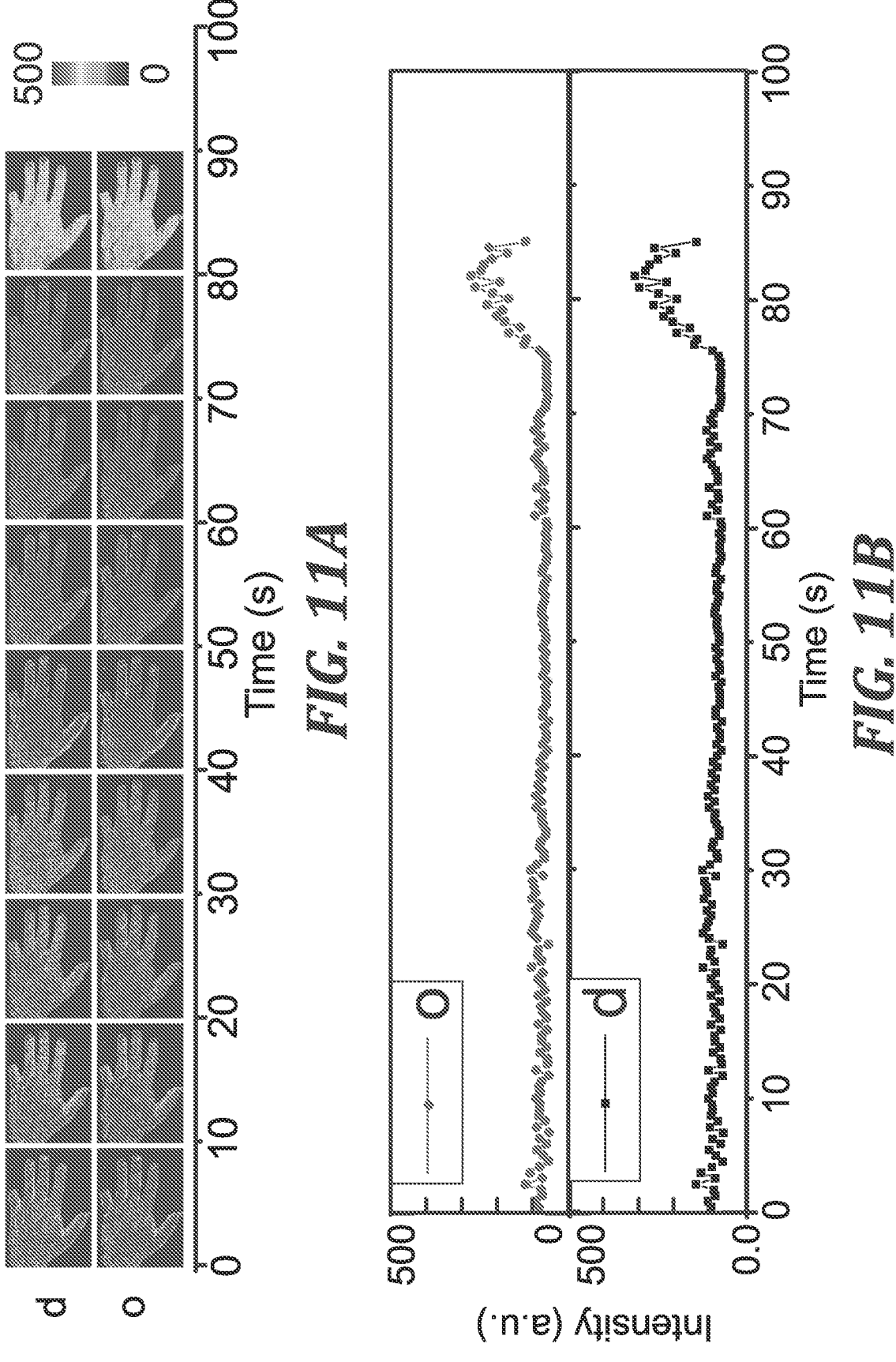
FIG. 11A is a series of representative pulsation maps, in accordance with the present technology.
FIG. 11B shows corresponding time traces of the pulsation strengths averaged from the selected ROI, in accordance with the present technology.

This experiment demonstrated changes in $HbO_2$ and Hb concentrations due to blood cuff maneuver on the arm. The maneuver of the blood cuff pressure on the upper arm progressively occludes the relatively superficial venules that drain the blood from the forearm. This action results in a gradual increase of the deoxygenated blood pooling at the downstream of skin beds and a gradual decrease of oxygenated blood. FIG. 11A shows the representative maps indicating the changes in $HbO_2$ and Hb concentrations at the dorsal skin tissue beds of the challenged left hand, extracted from the spatiotemporal images at four observation time points of each experimental trial: 1) the onset of the application of pressure cuff on the upper arm, 2) the time instant at the halfway of the video recording, 3) the time instant when the pressure cuff was released, and 4) the finishing time of the video recording. For all the experimental trials except for the zero-cuff pressure (i.e., the control), the decrease in $HbO_2$ concentration within the skin tissue beds were observed with the application of pressure cuff, whereas the opposite trends were true for Hb concentration. After releasing the cuff pressure on the upper arm, a rapid recovery of the $HbO_2$ and Hb was seen. Comparing among different trials, the degree of changes in $HbO_2$ and Hb concentration from onset to release agrees positively with the level of pressure applied.

In some embodiments, a region of a body is selected to calculate the blood oxygen levels. In some embodiments, the region of the body is a hand, a face, a neck, or an eye socket, but it may be any region of the body. To demonstrate the temporal profile of the measured signal, a region of interest (ROI) was selected on the dorsal hand skin and calculated the averaged values of the changes at each frame in the time course of spatiotemporal dynamic images. The averaging operation for a selected region was for the purpose of improving the signal quality and reducing the noises because the smartphone camera 200 that was used was only of 8-bit depth. The time traces of the measured $SaO_2$ values are shown in FIG. 10B. In FIG. 10C, which show the time traces of decoupled $HbO_2$ and Hb. As expected, the changes in $HbO_2$ concentration show a continuous decrease with the cuff on and a rapid recovery right after the cuff was released. The opposite trends are observed for the changes in Hb concentration. These results match well with the values of oxygen saturations read by the pulse oximeter (FIG. 10B). Decreased oxygenation values indicate decreased concentration of the oxygenated blood within the skin tissue beds. The changes in total hemoglobin concentration was also calculated for each experimental trial by summing corresponding changes in $HbO_2$ and Hb together (FIG. 10D). Except for the control, the changes in total hemoglobin concentration increase in all trials. Since venules are located more superficially than arteries in the upper arm, the application of cuff pressure causes severer occlusion in venules than arteries, leading to gradual blood pooling in the downstream of the forearm, indicating the validity of the results observed in the experiments. It is worthy to mention that all the values of concentration changes ($\Delta c$) were calculated when the light interaction path length (l) was assumed to be 1 mm. The real values of $\Delta c$ can be affected by this assumption, and can be improved by a more realistic l under specific illumination and imaging conditions.

FIGS. 11A-11B show dynamic blood pulsation maps can be obtained from the spatiotemporal changes in $HbO_2$ and Hb concentrations as evaluated from the smartphone recorded videos. FIG. 11A is a series of representative pulsation maps, in accordance with the present technology. At the time instants as shown derived from the respective Hb (top row) and $HbO_2$ signals (bottom row), when a 110-mmHg cuff pressure was applied at the upper arm, the oxygen saturation at the little finger reached 93% as monitored by the pulse oximeter, i.e., the experimental trial c5: 110 mmHg/93%. FIG. 11B shows corresponding time traces of the pulsation strengths averaged from the selected ROI, in accordance with the present technology. The results are derived from both the $HbO_2$ (Top) and Hb signals (bottom), respectively, evaluated from a time window of 10 s sliding through the entire recording time with a step time length of 0.5 s. Cuff releasing time was at ~80 s. Oxygenated blood is indicated by the label of "o", and deoxygenated blood by "d" in the FIGS. 11A-11B.

Pulsations of oxygenated and deoxygenated blood in cuff pressure experiments are also described herein. With the obtained spatiotemporal changes of oxygenated and deoxygenated blood due to the blood cuff maneuver at the upper arm, a window-based lock-in amplification algorithm as described in Section 2.4 was applied to map the spatial pulsation amplitudes at the skin tissue beds as imaged by the smartphone. Since the experiment was conducted with the subject in sitting position that made the forearm about 20 cm below the heat level, the blood pulsation in the hand skin beds would be relatively weaker when compared to the positions that are above the heart level, due to the gravity effect. Therefore, a longer time window of 10 seconds was applied to maximally extract the heart frequency signal. It was successful to map the blood pulsation strengths for all the experimental trials conducted. As an example, FIG. 11A shows the spatial pulsation maps resulted from the respective spatiotemporal changes of $HbO_2$ and Hb concentrations, when 110 mmHg cuff pressure was applied at the upper arm of the subject (i.e., the trial c5). FIG. 11B illustrates the corresponding time traces of the pulsation strength averaged within the selected ROI (square region marked in the upper left figure in FIG. 10A). It can be observed that the blood pulsations remain relatively weak when the cuff pressure was applied, while being approximately the same strength for both the oxygenated and deoxygenated blood volumes. These are expected because mathematically and physically, the pulsation derived from the dynamic concentrations of either $HbO_2$ or Hb should be the same as the total effective blood volume. Upon after releasing the cuff pressure, the blood pulsation shows a significant re-bound, indicating that both oxygenated and deoxygenated blood are experiencing a recovery associated with a strong pulsation, which is more clearly illustrated in the time trace curves of the average pulsation intensity in the selected ROI (FIG. 11B).

Figure 12B:
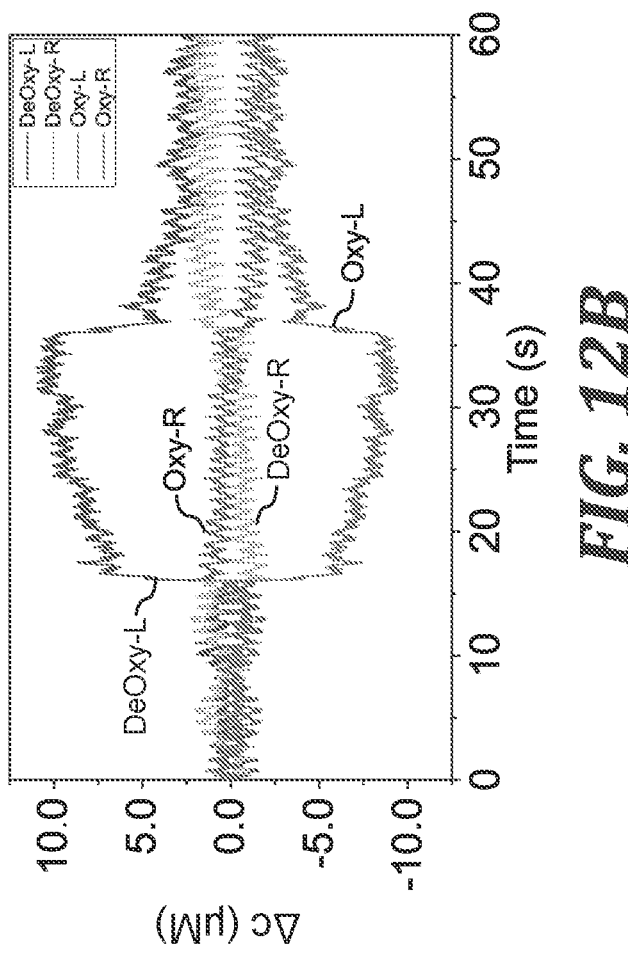
FIG. 12B shows time traces of averaged values of $HbO_2$ and Hb changes within the selected ROIs, in accordance with the present technology.
Figure 12A:
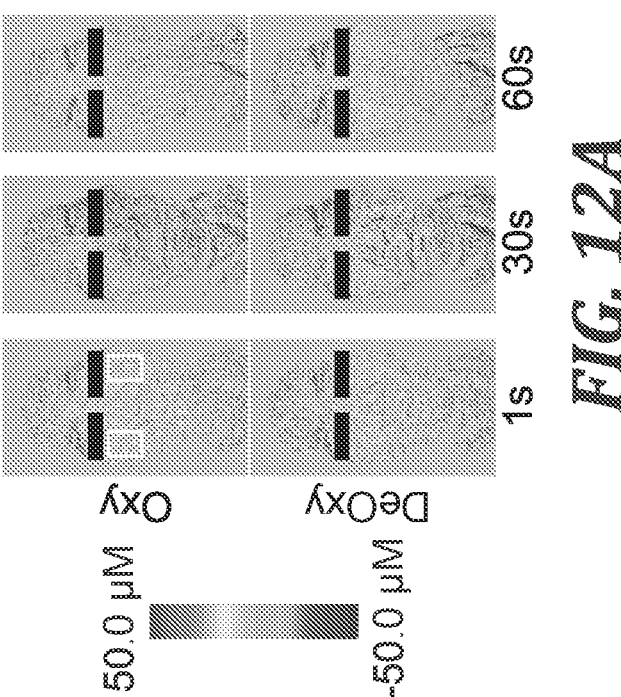
FIG. 12A shows the representative maps of $HbO_2$ (top row) and Hb (bottom row) changes of the facial skin at three time points, in accordance with the present technology.
Figure 12D:
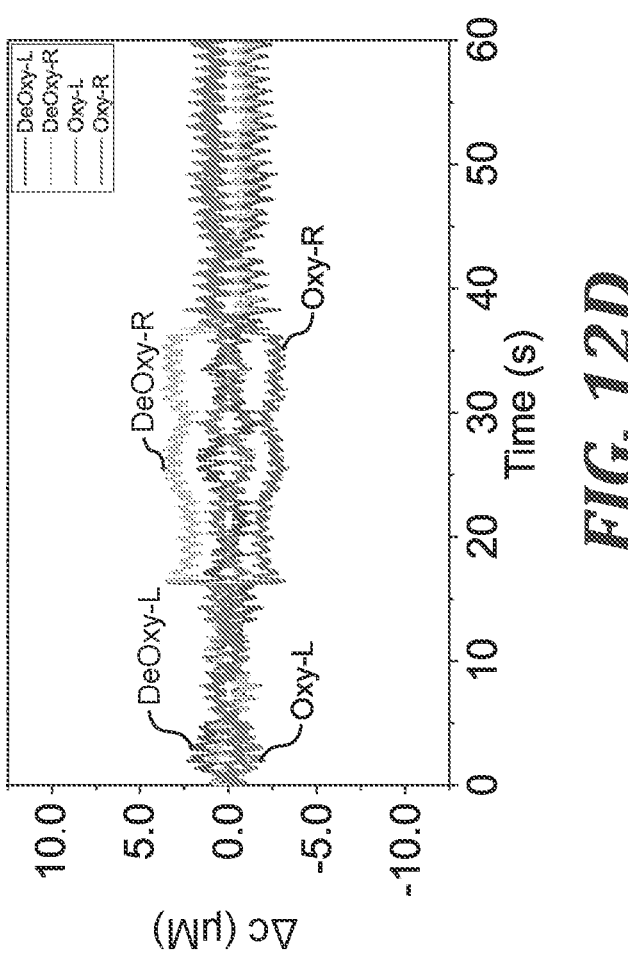
FIG. 12D shows time traces of averaged values of $HbO_2$ and Hb changes within the selected ROIs, in accordance with the present technology.
Figure 12C:
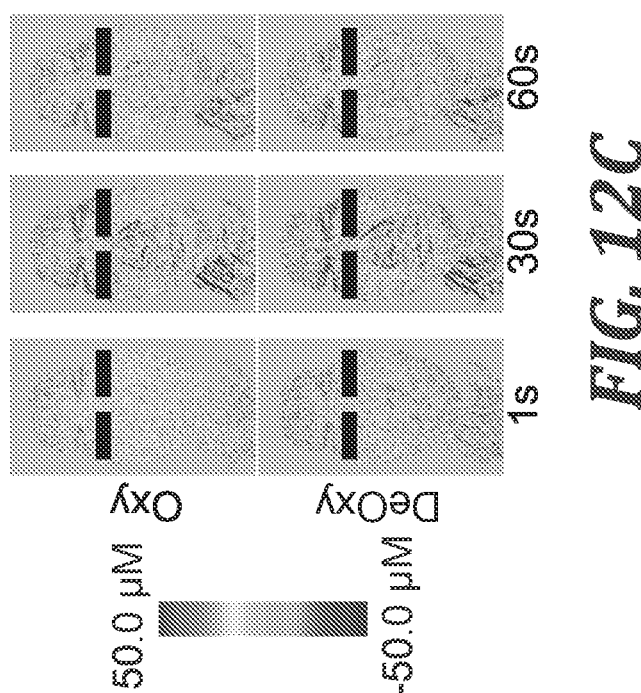
FIG. 12C shows the representative maps of $HbO_2$ (top row) and Hb (bottom row) changes of the facial skin at three time points, in accordance with the present technology.
Figure 12F:
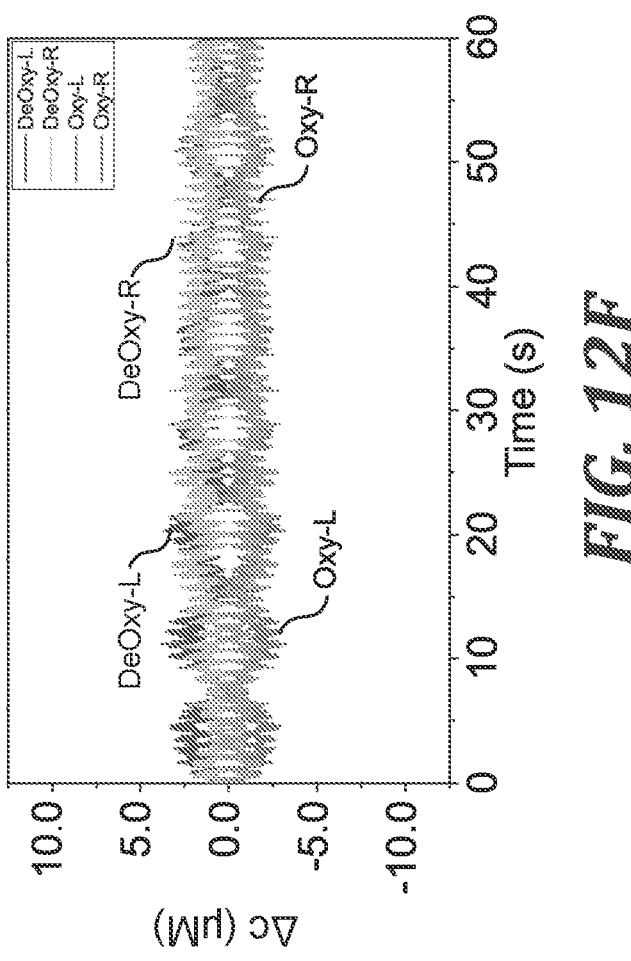
FIG. 12F shows time traces of averaged values of $HbO_2$ and Hb changes within the selected ROIs, in accordance with the present technology.
Figure 12E:
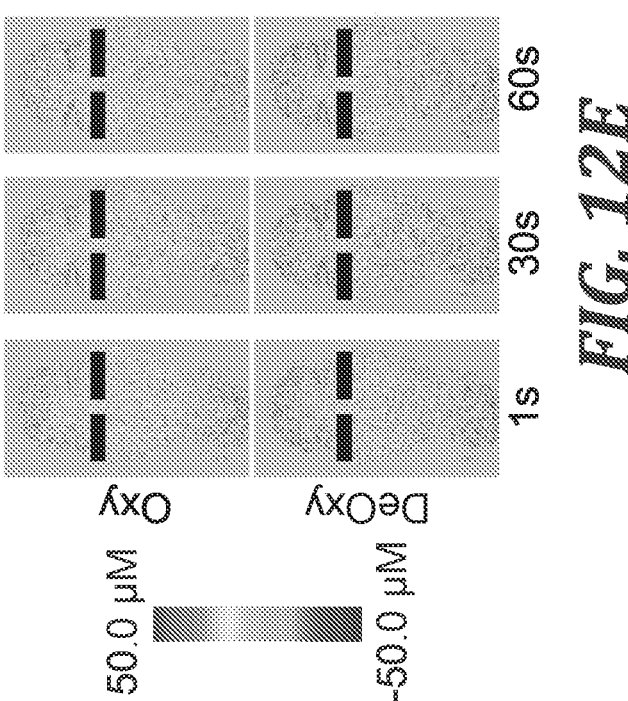
FIG. 12E shows the representative maps of $HbO_2$ (top row) and Hb (bottom row) changes of the facial skin at three time points, in accordance with the present technology.

FIGS. 12A-12D show the proposed SP-rmPPG can provide dynamic information of $HbO_2$ and Hb within the facial skin tissue beds when blood supply is limited by pressing the facial arteries in the lower jaw region. FIG. 12A shows the representative maps of $HbO_2$ (top row) and Hb (bottom row) changes of the facial skin at three time points, in accordance with the present technology. The three time points are 1 second, 30 seconds, and 60 seconds. When the left facial artery was pressed at the time of ~15 s after the onset of the video recording, the blood pulsation is seen. The white box area in the top left figure indicates the selected ROIs for evaluating the temporal time trace signals. FIG. 12B shows time traces of averaged values of $HbO_2$ and Hb changes within the selected ROIs, in accordance with the present technology. The ROIs are: R (right cheek) and L (left cheek) as shown in FIG. 12A. FIG. 12C shows the representative maps of $HbO_2$ (top row) and Hb (bottom row) changes of the facial skin at three time points, in accordance with the present technology. FIG. 12D shows time traces of averaged values of $HbO_2$ and Hb changes within the selected ROIs, in accordance with the present technology. FIG. 12C and FIG. 12D are the same as in FIG. 12A and FIG. 12B, respectively, but the right facial artery was limited. FIG. 12E shows the representative maps of $HbO_2$ (top row) and Hb (bottom row) changes of the facial skin at three time points, in accordance with the present technology. FIG. 12F shows time traces of averaged values of $HbO_2$ and Hb changes within the selected ROIs, in accordance with the present technology. FIG. 12E and FIG. 12F are the same as in FIG. 12A and FIG. 12B, but they show the control experiment, i.e. no pressing on the facial artery was applied.

Figure 13A:
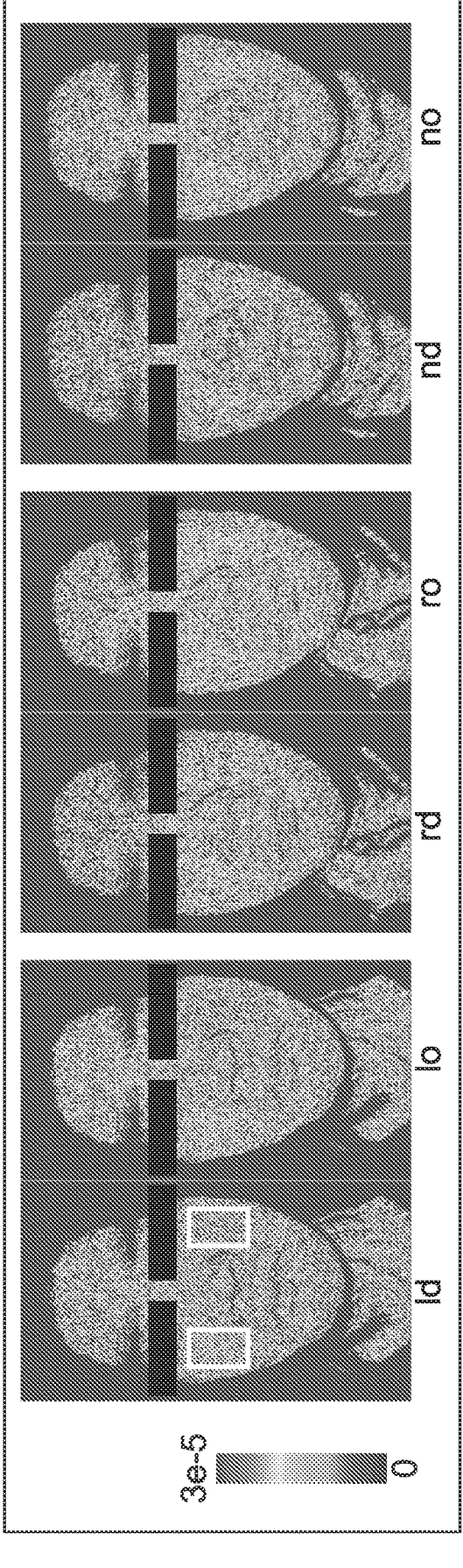
FIG. 13A is a series of representative pulsation maps extracted from dynamic images, in accordance with the present technology.
Figure 13B:
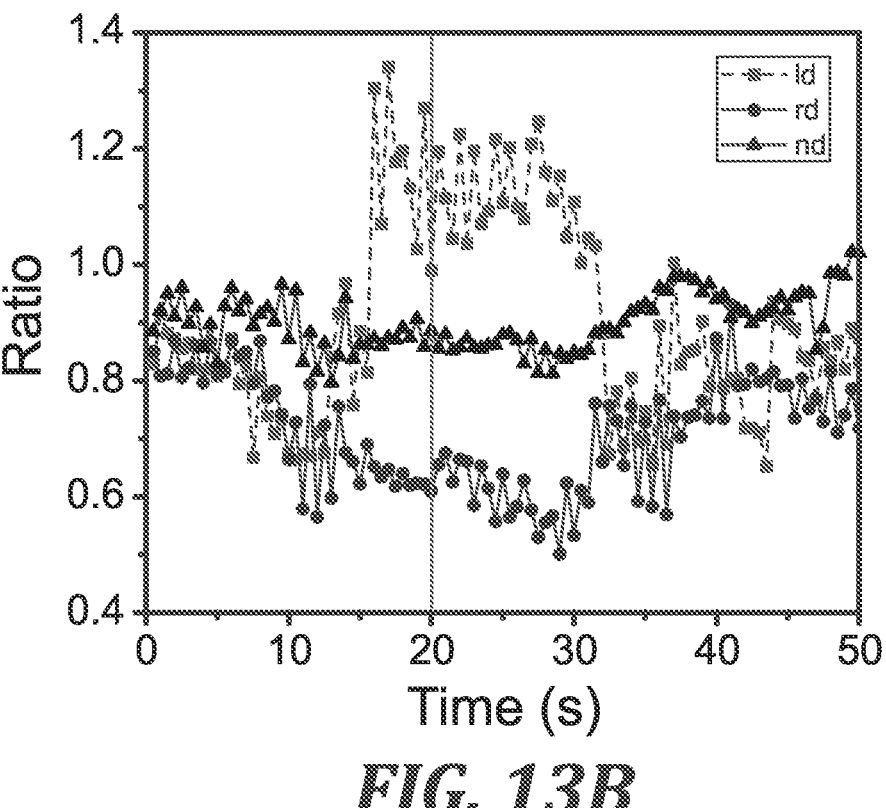
FIG. 13B are time traces of temporal ratios of averaged pulsation intensity values derived from dynamic Hb signals, in accordance with the present technology.

Changes in $HbO_2$ and Hb concentrations in facial skin were also observed and measured. After the conducted feasibility study using the popular blood cuff maneuver on the subject's upper arm, experiments to demonstrate whether the proposed SP-rmPPG can monitor the changes of $HbO_2$ and Hb within the facial skin tissue beds (See the procedure in Section 2.5) were performed. With the finger pressed on the facial arteries located at the lower jaw region to partially occlude the blood supply to the facial skin tissue beds for ~20 s duration at ~15 s after the onset of the video recording, FIG. 13A shows the representative dynamic facial skin maps of the changes in $HbO_2$ and Hb at the time instants of 1 s, 30 s and 60 s, respectively, when the left facial artery branch was pressurized. The corresponding time traces of $HbO_2$ and Hb changes on left and right cheeks are shown in FIG. 13B that were assessed by averaging the values within the regions of interest (the region marked by white boxes in the top left figure) at each frame for the entire time-period of video recording. During the first 15 s, both the $HbO_2$ and Hb signals are fluctuating around the zero level.

At the time when the left facial artery was challenged by applying pressure on it, the $HbO_2$ started to rapidly decrease and Hb to increase at the left cheek, while the changes at the right cheek region were minimal. With the pressure sustained at the position for a period of 20 s, the decrease in $HbO_2$ and increase in Hb sustained in the left cheek, but at a much slower rate. Afterwards, the changes rapidly rebounded when the pressure was released and then slowly approaching the initial normal level. Such behaviors of changes in $HbO_2$ and Hb are expected from normal physiology for a tissue region that experiences a temporary shortage of blood supply (i.e., a transient ischemic attack).

However, a slight opposite trend of changes in $HbO_2$ and Hb was observed at the contralateral right creek, where the blood supply was not limited, but the $HbO_2$ was seen slightly increase and Hb decrease during the partial occlusive maneuver on the left facial artery, and then the trend reversed after the pressure was lifted. This may be explained by the symmetrical relationship of arterial supply and venular drainage between the left and right cheeks where an ischemic impairment at one side would likely evoke a response at its dependent contralateral side, trying to balance circulation system likely due to microvascular or sympathetic nerve autoregulation.

FIGS. 12C and 12D show the spatiotemporal changes in the $HbO_2$ and HB of the skin tissue beds at both the right and left cheeks, albeit with the right facial artery challenged to limit the blood supply to right facial regions. The changes are observed the same as that of left-pressing experiment but with the trend reversed. However, the changes are in much smaller magnitude in this case, likely due to insufficient pressure on the right facial artery applied by the finger pressing. In FIGS. 12E and 12F, the spatiotemporal results of the control group are shown. As expected, the perfusion changes are moderate and stable over the time period of smartphone video recording. These results sufficiently demonstrate that the proposed SP-rmPPG method is feasible to detect the dynamic oxygenation status within the facial skin tissue beds, simply by the use of a widely available and cost-effective smartphone.

Figure 13C:
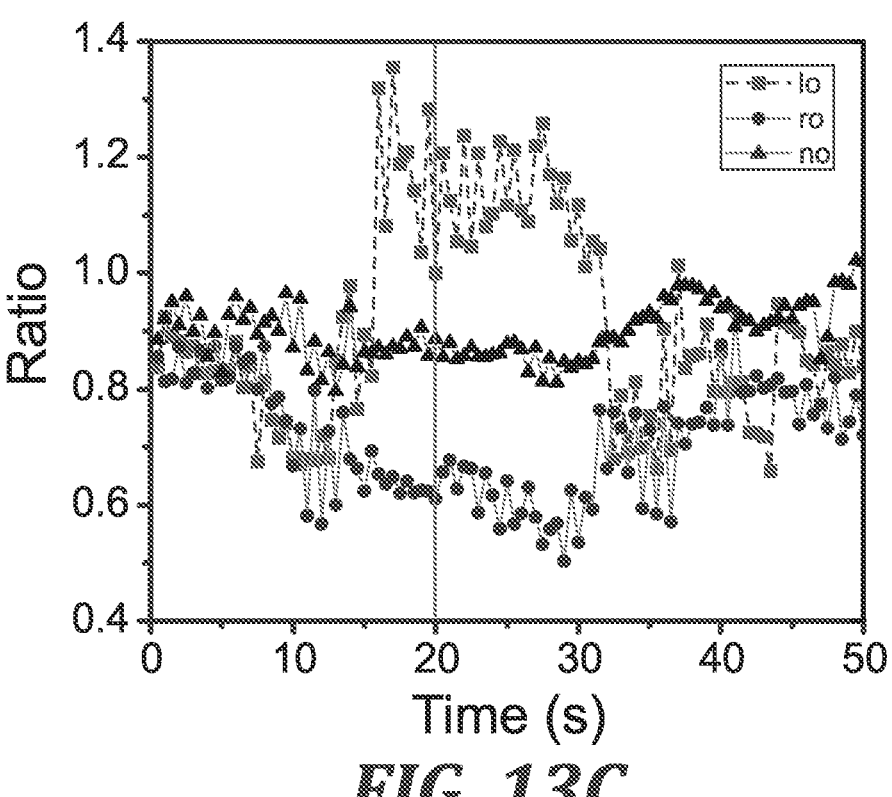
FIG. 13C shows time traces of temporal ratios of averaged pulsation intensity values derived from dynamic $HbO_2$ signals, in accordance with the present technology.

FIGS. 13A-13C show the SP-rmPPG is able to image dynamic changes of blood pulsation within the facial skin tissue beds upon the challenging of the blood supplying facial arteries. FIG. 13A is a series of representative pulsation maps extracted from dynamic images, in accordance with the present technology. FIG. 13A was taken at the time of 20-second, derived from the spatiotemporal $HbO_2$ (o) and Hb (d) signals obtained from the facial skin for three experimental trials (l: challenging on left supplying artery; r: challenging on right supplying artery; n: control group without challenging). FIG. 13B are time traces of temporal ratios of averaged pulsation intensity values derived from dynamic Hb signals, in accordance with the present technology. The dynamic Hb signals were derived between right and left cheeks at the selected ROIs (right/left). FIG. 13C shows time traces of temporal ratios of averaged pulsation intensity values derived from dynamic $HbO_2$ signals, in accordance with the present technology. As in FIG. 13B, the dynamic $HbO_2$ signals were derived between right and left cheeks at the selected ROIs (right/left).

Pulsations of oxygenated and deoxygenated blood in facial skin were also observed and measured. The spatiotemporal pulsation maps of the facial skin derived from the spatiotemporal changes in $HbO_2$ and Hb are shown in FIGS. 13A-13B for the facial artery challenging experiments. The representative pulsation maps at the time instant of 20 s extracted from the spatiotemporal images are shown in FIGS. 13A-13B, for the experimental trials of 1) left facial artery was challenged, 2) right facial artery was challenged, and 3) control. For the case of occluding left artery, lower pulsation amplitudes for both the $HbO_2$ and Hb are seen at the left side of the cheek compared to its contralateral right cheek, indicating that limiting the blood supply to the skin tissue beds in the left cheek reduces its blood pulsation. The opposite change is true for the case of right artery challenging. However, there is no observed difference between the left and right cheeks for the control group, i.e., they remain symmetrical. Since the signal to noise ratio is relatively low due to the use of smartphone that has limited bit-depths (8-bits), the averaged pulsation amplitudes within the selected regions of interest (ROI) were calculated at each frame in order to improve the signal to noise ratio. The ROIs were selected symmetrically at the right and left cheeks, marked as white boxes in left figure of FIG. 13A. The ratio of pulsation amplitudes between right and left cheeks in each time window were then calculated to further contrast the imbalance of blood pulsation within the skin tissue beds at the right and left cheeks. In doing so, the time traces of the ratios of either Hb (FIG. 13B) or $HbO_2$ (FIG. 13C) pulsation amplitude in three trials can be obtained. It is observed that for the control group, the ratio sways between 0.8 and 1.0.

However, for the left artery challenging case, the ratio reaches more than 1.3, while it becomes ~0.5 for the right artery challenge case. The ratios resulted from Hb (FIG. 13B) and $HbO_2$ (FIG. 13C) are almost identical, which is expected because the pulsations so evaluated should be the same and equal to the pulsation of total blood volume within the skin tissue beds. These results support the conclusion that the changes in blood pulsation due to the induced ischemia at the facial tissue beds can be measured by the smartphone, which may be useful in the applications of assessing cardiovascular diseases, for example strokes at risk where the obstruction of internal carotid artery is often the cause of stroke.

A SP-rmPPG method and system to monitor the spatiotemporal changes in oxygenated and deoxygenated hemoglobin concentrations in the effective blood volume within the light interrogated skin tissue beds, and further to map the blood pulsation amplitudes is demonstrated. The results of cuff pressure experiments on the upper arm provided the feasibility of the proposed method to reflect the impact of the occlusion at the upstream blood vessels on the downstream blood perfusion at the extremity of skin tissue beds. The results obtained by the proposed method agreed well with the parallel peripheral oxygenation measurements from the pulse oximeter. The spatiotemporal $HbO_2$ and Hb changes and the blood pulsations of the skin tissue beds at the challenged hand with and without cuff pressure at the upper arm also agreed with the expected changes in the cutaneous blood oxygenation in this well-known and popular blood cuff maneuver. The proposed method is capable of measuring the spatiotemporal changes in the oxygenated and deoxygenated blood within the facial skin when it was challenged by a transient ischemic event induced by artificially limiting the blood supply to the tissue region at the external carotid artery. The observed imbalance of the oxygen supply and the blood pulsations within the facial skin tissue beds between the left and right cheeks indicates that the method may be useful in detecting or monitoring certain cardiovascular diseases like carotid stenosis, and in doing so by only taking selfie videos with a cost-effective smartphone.

The values of spatiotemporal $HbO_2$ and Hb changes that were obtained were scaled by the light interaction path length in the skin tissue (Eq. 21 and Eq. 22). It was assumed that this path length was 1 mm in this study. From the measurements, it was estimated that the averaged concentration changes of Hb and $HbO_2$ was ~16.5 μM for every 1% decrease of the $SaO_2$ value from FIG. 11C. For a normal male subject, the concentration of total hemoglobin in the whole blood is approximately ~2500 μM. In this case, every 1% decrease of $SaO_2$ would theoretically cause concentration changes of Hb and $HbO_2$ at ~25 μM. Consequently, the measured changes by the smartphone were approximately in line with the theoretical predictions (which on the other hand, indicates the validity of the proposed SP-rmPPG method). Given the limited penetration depth of visible lights, thickness of epidermis and dermis in the dorsal skin of hand, and relatively weak illumination of the smartphone flashlight, the actual light interaction path length is likely to be smaller than 1 mm. If this is the case, then the measured values would be closer to the theoretical value. Therefore, there is still a room to improve the accuracy of the measured changes in $HbO_2$ and Hb by carefully determining the practical and more realistic values of the light interaction path length in biological tissue through, for example, using Monte Carlo simulations of the light (with the wavelengths of interest) propagating within the skin tissue taking into account the consideration of its proper optical properties possibly combined with the measurements of optical coherence tomography of depth-resolved skin morphology and microcirculation information.

Compared with the conventional single-wavelength PPG (swPPG), the multiple-wavelength PPG (mwPPG) has been demonstrated to have superior performance in detecting the blood pulsation in terms of its signal quality and robustness, thus increasingly gaining attentions from both academic researchers and industrial entrepreneurs. Most mwPPG sensors rely on the use of multiple light sources each with different wavelength or a more complicated spectrometer-like photodetector array, leading to a bulky system setup and associated complicated control to implement, let alone the cost issues. Nevertheless, such strategy has been adopted by many remote PPG (rm-PPG) systems. Due to the demand of the wide-field illumination and imaging, the system setup of a rm-PPG becomes even more complicated than mw-PPG does. A simple solution is to realize rm-PPG by employing unmodified and intact commercial smartphones through an algorithm that can convert the color images (video) captured by the built-in cameras into the multispectral video cubes. Due to the minimal constraints in hardware requirements, the proposed method provided an advantage of flexibility to select the wavelengths of interest and multi-channel processing. Though it is a "pseudo" multispectral imaging that was achieved, the method can still be used to decouple the dominant bio-chromophores from the videos of the dynamic light reflectance emerging at the skin tissue surface to realize a refined monitoring of skin hemodynamics. Besides, rather than simply detecting the heart rate and pulse waves, the method offers another perspective for the analysis and monitoring of spatiotemporal hemodynamic activities. For example, from the imbalanced hemodynamic responses between the left and right sides of the cheek, the existence of vascular disorder in corresponding carotid arteries can be measured.

The experiments conducted and analyzed in this study may be directly relevant to some clinical applications. The cuff pressure experiments on the upper limp could be a useful method in the assessment and monitoring of peripheral vascular diseases that cause the blood vessels outside of the heart and brain to narrow, block, or spasm, for example in the cases of arteriosclerosis, or even diabetes. The facial tissue imaging experiments may be useful in the assessment or prediction of possible obstruction of major blood supplying arteries to the downstream tissue beds, which might cause transient ischemic attacks and even stroke. The method can also be used to derive and spatially localize the lesion area from the field of view. In addition to the potential usage in clinical scenarios, there would also be a potential space for the SP-rmPPG system to be applied in general health care because of the current ever-growing accessibility and affordability of the smartphone to the general public. It may be envisioned that the future smartphone can have an ability to perform daily monitoring of the skin hemodynamics to support the early screening and interventions of the potential cardiovascular diseases.

Though as promising as it has been demonstrated, the limitations in the use of smartphone to realize rmPPG cannot be ignored. Since current commercial smartphones are not designed to fulfill the requirements for biomedical imaging, there are inherent limitations in their hardware design, including the camera sensor and the flashlight with limited wavelength range. Most smartphones employ 8~10-bit camera sensors and produce compressed 8-bit videos, presenting challenges to acquire blood pulse waveforms with high fidelity. Even with the compensation of illumination uniformity, the flashlight still provides limited irradiance to the target samples for imaging purposes and its available wavelengths are confined within the visible range limited by a near infrared filter within the housing. Due to these constraints, the measured spatiotemporal changes in $HbO_2$ and Hb by the proposed SP-rmPPG were inevitably noisy. A good averaging within a selected region of interest to improve the signal to noise ratio of temporal change signals to derive $HbO_2$, Hb and blood pulsation information had to be performed. These limitations may be partly reduced if one has the ability to access its raw videos and to remove its near infrared filter by working together with the smartphone manufacturers. Alternatively, if resources permit, these limitations can be removed by configuring a dedicated high-performance system that employs high bit-depth camera sensors and high irradiance light sources with appropriate working wavelengths of interest that extend from visible to near infrared region.

The experiments were used to simulate vascular diseases for a proof-of-concept study. It can be imagined that the real situation would be much more complicated and individualized. In some embodiments, in order to resolve data storage issues, cloud computing and deep learning technologies are used to store and process the acquired data.

In the method, the skin color videos captured by an unmodified smartphone camera 200 was first converted into the multispectral data cubes 500, upon which to derive the spatiotemporal changes in oxygenation status within the skin beds through a novel algorithm that can decouple the chromophore determinants of oxygenated and deoxygenated hemoglobin. The corresponding spatiotemporal blood pulsation were then mapped by a window-based lock-in amplification method. The feasibility of the proposed SP-rmPPG method using the popular blood cuff pressure maneuver on the upper arm to occlude the blood supply to the downstream tissue beds has been shown, where the measured dynamic information of oxygenated and deoxygenated blood in the downstream agreed well with the parallel measurements of oxygenation saturation provided by the standard pulse oximeter. It has also been demonstrated that the ability of the SP-rmPPG method to monitor the hemodynamic information within the facial skin tissue beds that were challenged by an transient ischemic event. Due to the ever-growing accessibility and affordability of the smartphone to the general public, the proposed system and method are expected to be useful in the vital sign monitoring, in the early screening of peripheral artery diseases and cardiovascular disorders, as well as in the investigations of vascular functions. In particular due to its attributes of low-cost, compactness and usability, it is expected to serve the health care systems well in the rural areas where the medical resources are severely limited.

EXAMPLE #3

Figure 14A:
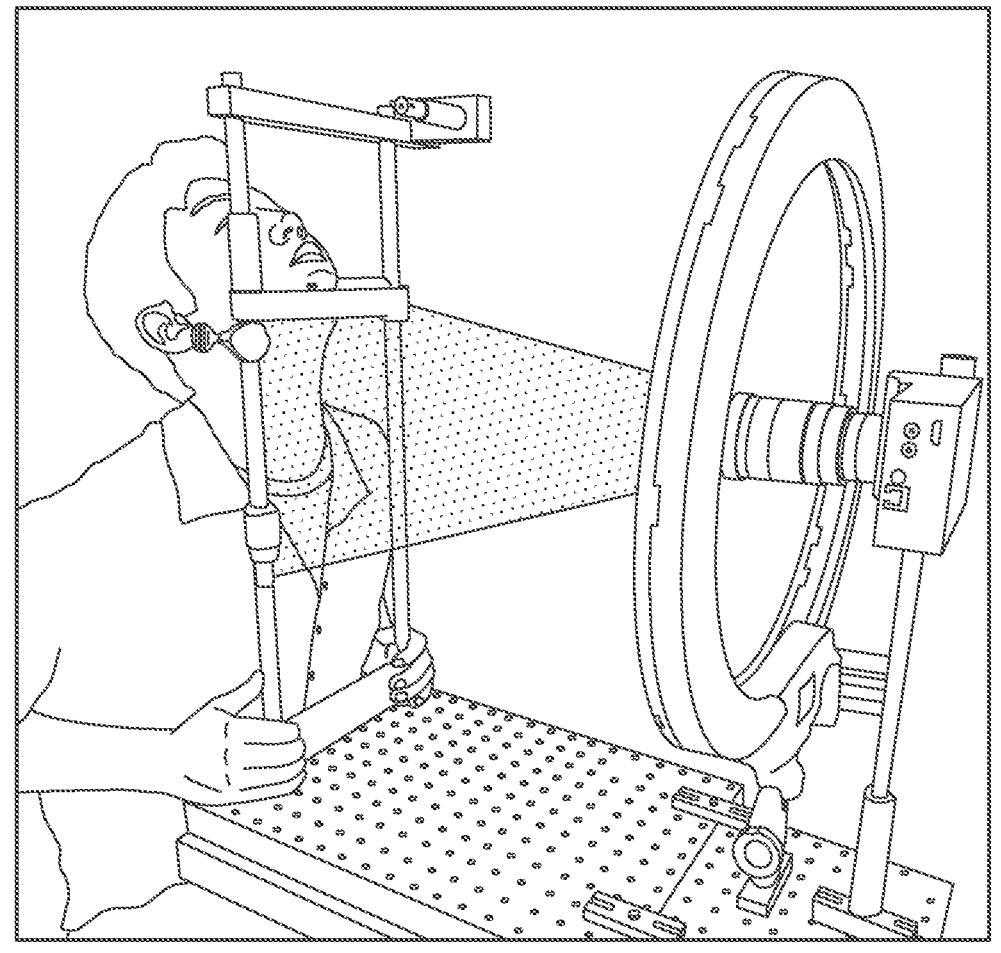
FIG. 14A is a schematic of μMI system setup, in accordance with the present technology.
Figures 14B, 14C, 14D, 14E:
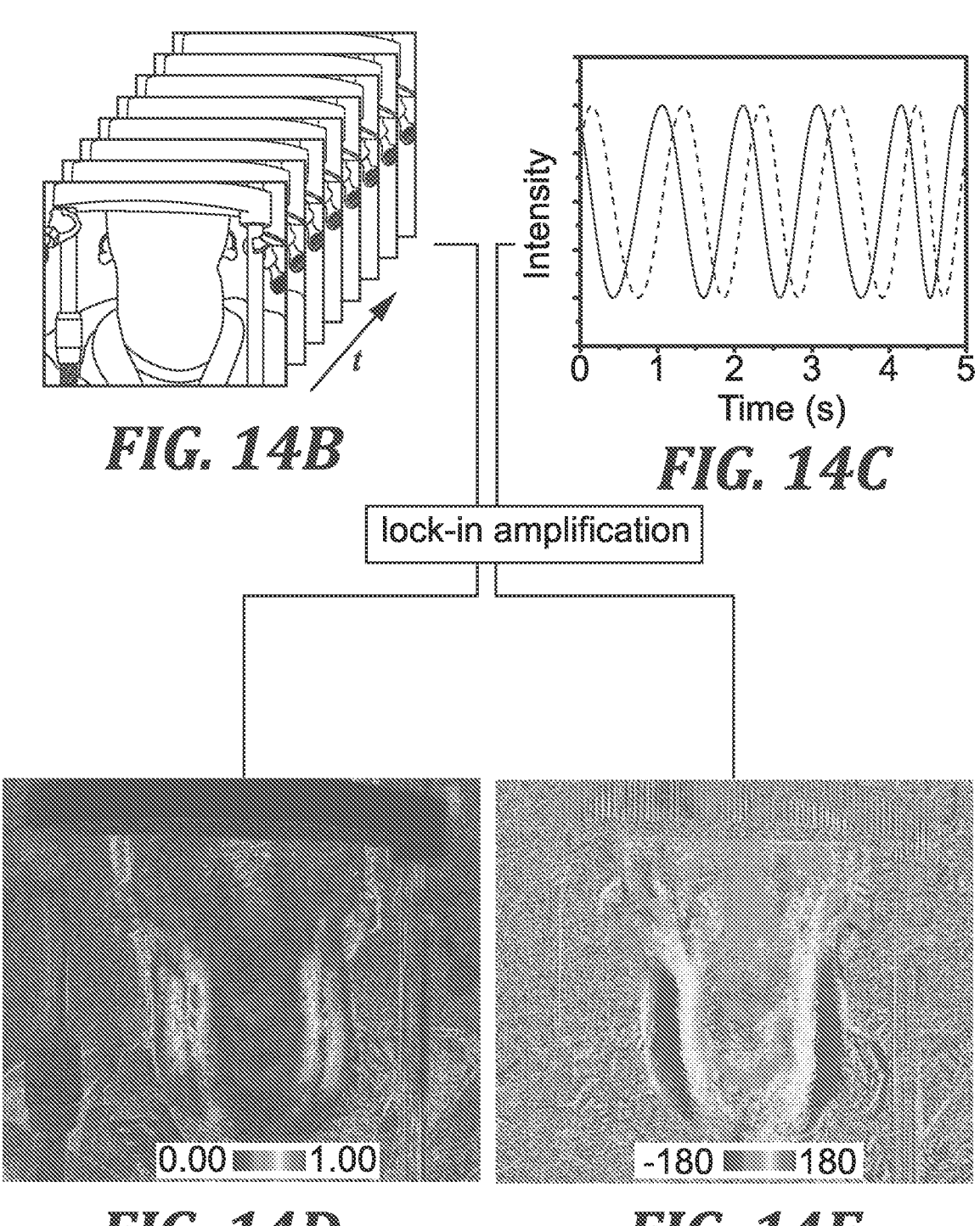
FIG. 14B is a still from a video of neck skin after motion correction, in accordance with the present technology.
FIG. 14C is a reference function in accordance with the present technology.
FIG. 14D is an amplitude map of heart-cycle-related micro-motion, in accordance with the present technology.
FIG. 14E is a phase map of heart-cycle-related micro-motion, in accordance with the present technology.

FIG. 14A is a schematic of µMI system setup, in accordance with the present technology. FIGS. 14B-14E are schematics of processing with the lock-in amplification algorithm. FIG. 14B is a still from a video of neck skin after motion correction, in accordance with the present technology. FIG. 14C is a reference function in accordance with the present technology. FIG. 14D is an amplitude map of heart-cycle-related micro-motion, in accordance with the present technology. FIG. 14E is a phase map of heart-cycle-related micro-motion, in accordance with the present technology.

The schematic setup of the proposed µMI system is illustrated in FIG. 14A, where the neck skin was illuminated by a ring LED white light and then imaged by a 16-bit-depth camera (Chronos 1.4, Kron Technologies Inc. Canada). The ring LED provided uniform illumination in the field of view, where the values of U1 and U2 (the metrics used to assess irradiance uniformity) were measured to be 0.99 and 0.96, respectively. The reason for the selection of 16-bit-depth camera in the setup was to ensure that the camera sensor can record pulsatile signals with higher fidelity. This is important because the motion induced reflectance change only represents a small fraction of the background reflectance. The change of reflection caused by neck pulsatile motions, mixing with signals from respirational motions, global motions and blood absorption signals, are recorded together in videos for further processing.

Five healthy volunteers were enrolled in this study to investigate the performance of the µMI method. This study adhered to tenets of the Declaration of Helsinki and was performed in accordance with the Health Insurance Portability and Accountability Act. Ethical approval was obtained from the Institutional Review Board of the University of Washington. Informed consent was obtained from the subject prior to the start of each study session.

Before imaging, the volunteer was asked to sit in a chair for 5 minutes to stabilize the heart cycle. Then, the volunteer was asked to put his/her jaw on the chin rest to expose neck skin for video recording. Deep breaths and swallowing were avoided during the recording. The video recording lasted for 5 seconds at 100 frames per second. The pixel resolution of each frame was set to be 640×512.

As stated earlier, the recorded video contains signals caused by various motions and blood absorptions. In some embodiments, generating the phase map and the amplitude map comprises filtering the first pulse signal and the second pulse signal with one or more heartbeat frequencies to generate a filtered signal, and using the filtered signal as a reference function to extract and amplify the first pulse signal and the second pulse signal with the same frequency as the filtered signal at each voxel of the video. To extract neck pulse waveforms, in some embodiments, the video signals needed to be filtered by filtering out other signal components to retain the pulse-enabled micro-motions. For this purpose, subpixel registration was applied to correct global motions caused by the instability of the system. Considering that pulse-induced micro-motions only exist in localized skin regions, it is important to guide the selection of target region for accurate extraction of the neck pulse waveforms. In some embodiments a lock-in amplification algorithm is applied to calculate the pulsation maps from the video signals, as described in Example #2. Briefly, pulsatile signals were extracted from whole skin videos (FIG. 14B) by filtering the signals with heartbeat frequencies to exclude other motion components. The resulted signal (FIG. 14C) was used as a reference function to extract and amplify the localized pulsatile signal with the same frequency component as in the reference function at each voxel of the video. This processing procedure resulted in amplitude and phase maps, FIGS. 14D and 14E, respectively. Note that these maps also include signals from the blood absorption, which fluctuates at heartrate frequencies as well, thus cannot be eliminated. However, in further analysis, it was demonstrated that by comparing with the motion-induced signal pulsation, the absorption-induced pulsation is much weaker, thus can be neglected from the results.

From the motion amplitude map in FIG. 14D, there appears four distinct linear regions with high motion amplitudes (roughly appearing in the middle of the image), located at the two sides of the neck. With reference to anatomy, it was reasoned that these signals (from left to right) should be caused by pulses from right jugular vein, right common carotid artery, left common artery and left jugular vein, respectively. As shown in the phase map in FIG. 14E, the two regions covering arteries appear to have a delayed phase, whereas the other two regions covering veins appear to have a leading phase. This indicates that pulsations between CP and JVP waves are in opposite phases. It is worth noting that the motion caused by a carotid artery always reflects a new incoming pulse that has not entered the downstream jugular vein, thus CP-induced motions show a delay rather than a leading phase. The phase map was used as the guidance because of its superior performance to differentiate the signals caused by CP and JVP. Following the guidance, the accurate selections of target regions were conducted and accordingly extracted pulse waveforms from the video signals. Since human respiration has different frequencies when compared to the heartrates, the extracted waveforms are further processed with a band pass filter in Fourier domain to remove the respirational signal components. Following all these steps, the CP and JVP waveforms were achieved for further analyses In some embodiments, the blood measurements are displayed on a second communication device.

Figures 15A, 15B:
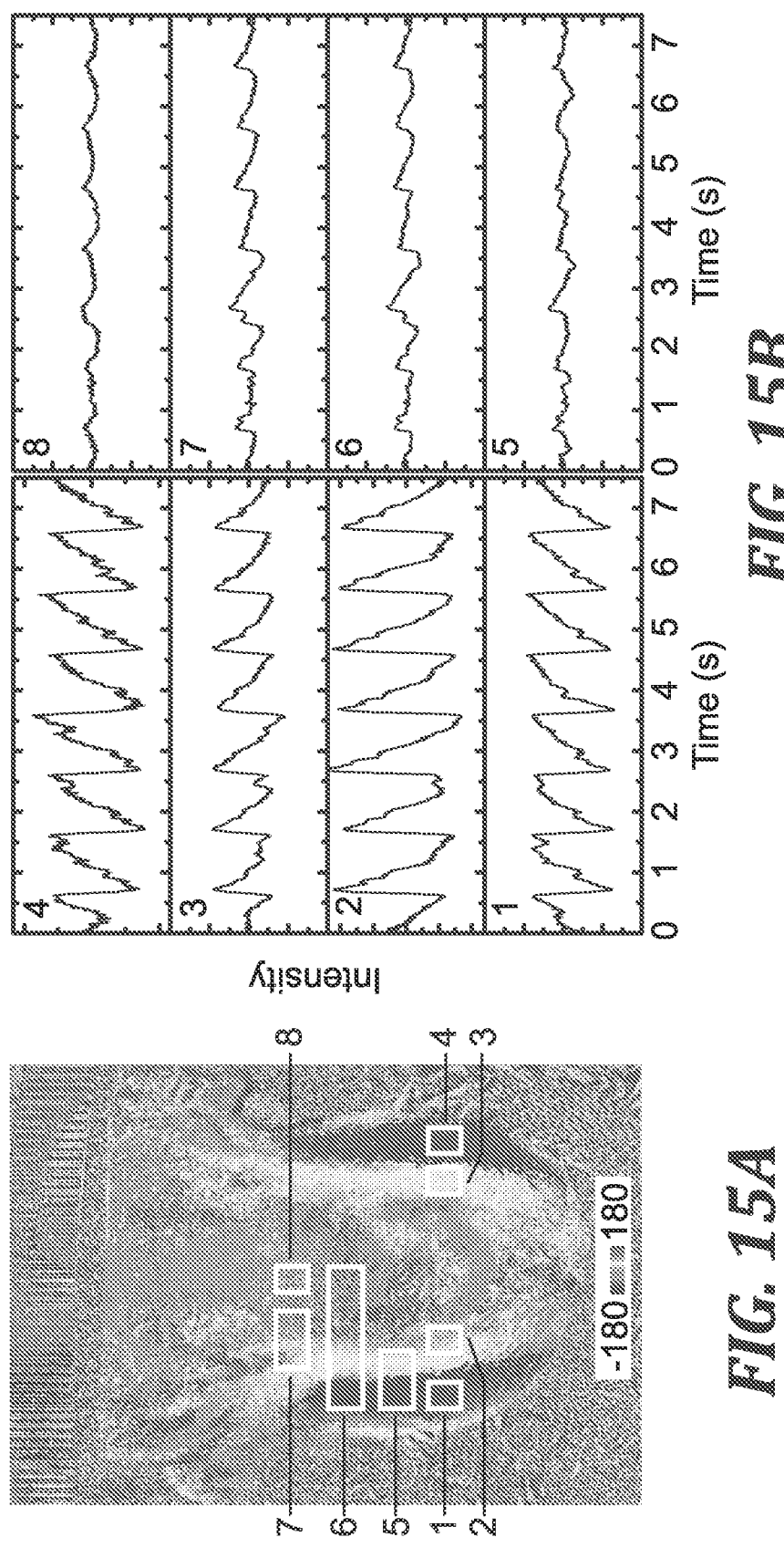
FIG. 15A is a resulting phase map of the pulsatile signals, in accordance with the present technology.
FIG. 15B is the extracted pulse waves in the corresponding 8 selected regions, in accordance with the present technology.

FIGS. 15A-15B show accurate extraction of the carotid pulse (CP) and jaguar vein pulse (CVP) from a camera-recorded video. FIG. 15A is a resulting phase map of the pulsatile signals, in accordance with the present technology. The resulting phase map is used to provide the selection of regions for the investigation of the fidelity of CP and CVP waveforms. Here, 8 regions were selected for pulse wave extraction, including: the right jugular vein only (region 1), the right common carotid artery only (region 2), the left common artery only (region 3), left jugular vein only (region 4), the right jugular vein and the right common carotid artery (region 5), the right jugular vein, the right common carotid artery and capillary (region 6), the right common carotid artery and capillary (region 7), and capillary (region 8). FIG. 15B is the extracted pulse waves in the corresponding 8 selected regions, in accordance with the present technology.

The calculated phase map was used as the reference to guide the extraction of regional pulse waves. To show the necessity of this guidance, the waveforms extracted from different skin regions were compared. As shown in FIG.

15A, 8 regions of interests were selected from the phase map. These regions were selected to indicate the right jugular vein only (region 1), the right common carotid artery only (region 2), the left common artery only (region 3), and the left jugular vein only (region 4). The region 5 was selected to cover an area across both the right jugular vein and the common carotid artery, the region 6 to encompass the right jugular vein, common carotid artery and capillary beds, and region 7 to include both the right common carotid artery and capillary beds. The region 8 was selected to indicate the capillary bed only. Note that the capillary signals, mainly due to the blood absorption, should appear in all the selected regions. However, the pulsation signal from the capillary beds is substantially weaker than those regions covering carotid and vein vessels (FIG. 14D), indicating that the signals due to capillary beds could be neglected in the study, which is aimed for extracting CP and JVP signals. FIG. 15B shows the extracted regional pulse waveforms accordingly, where the regions 2 and 3 give the typical PPG waveforms that attribute to the blood pulsation in the common carotid arteries. In the regions 1 and 4, the waveforms are shown to include the similar components like positive "a", "c", "v" and negative "x", "y" waves, indicating they are due to the jugular veins, i.e., the JVP waveforms. However, in the regions 5, 6 and 7, the pulse waveforms are severely contaminated because of the inaccurate selection of ROI, indicating that accurate selection of the appropriate regions for the extraction of CP and JVP waveforms is important. Region 8 shows the waveform caused by blood absorption of capillary beds, with much lower pulsatile amplitudes than CP and JVP waveforms. These experimental results confirm that the method can be used to guide the extraction of accurate and pure pulse waveforms.

Figures 16A, 16B, 16C, 16D, 16E:
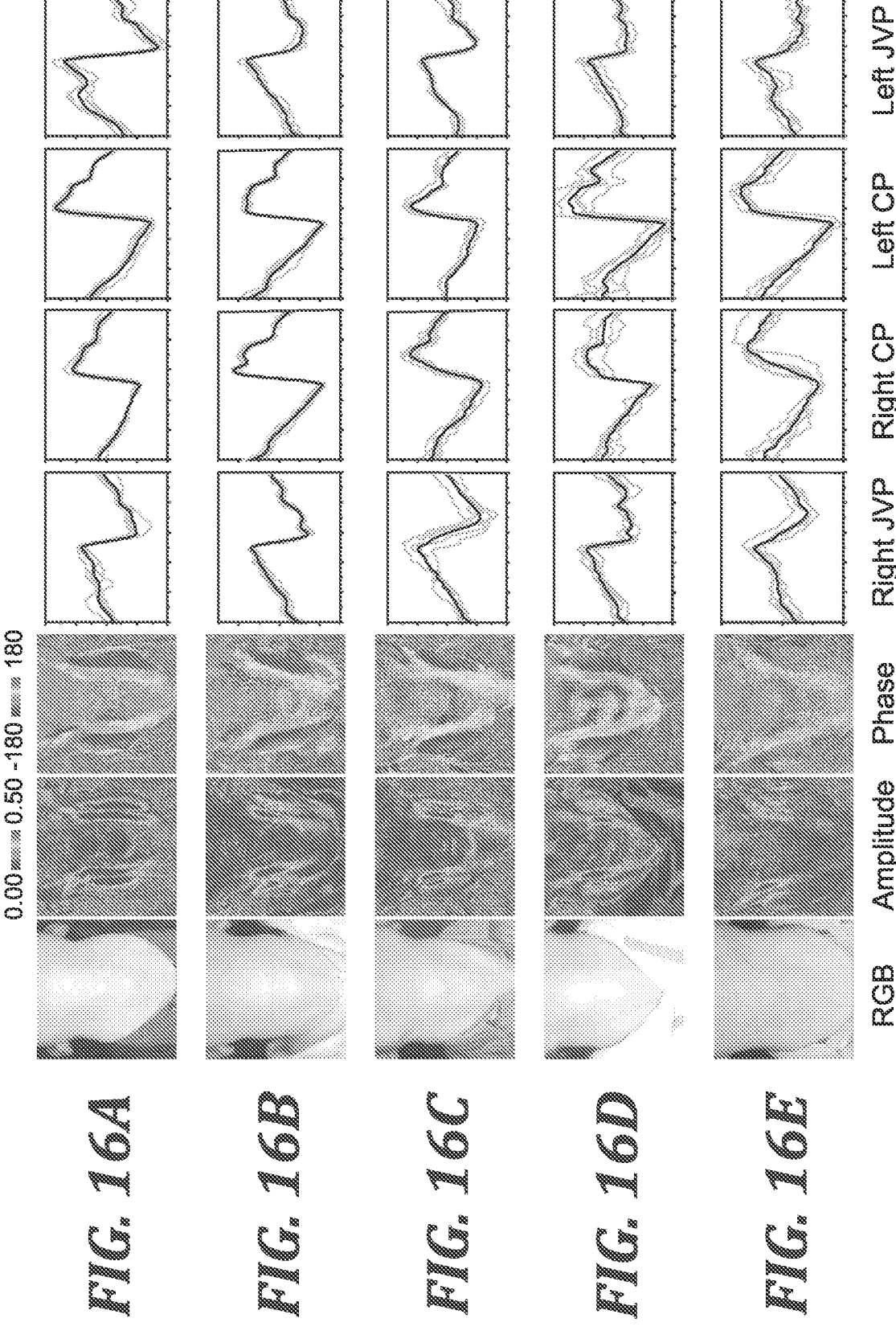
FIG. 16A is an example extraction from a volunteer in accordance with the present technology.
FIG. 16B is an example extraction from another volunteer in accordance with the present technology.
FIG. 16C is an example extraction from another volunteer in accordance with the present technology.
FIG. 16D is an example extraction from another volunteer in accordance with the present technology.
FIG. 16E is an example extraction from another volunteer in accordance with the present technology.

FIG. 16A-E show the extraction of JVP and CP waveforms from 5 volunteers. In these five cases: amplitude maps show four distinct linear regions with high motion amplitudes are located at the two sides of necks, indicating clear leading and delay phases; extracted CP waves consists of systolic peaks and dicrotic notches; most JVP waveforms contain positive "a", "c", "v" and negative "x", "y" waves. Photos in the left are shown for reference and represent one frame in the recorded video by the camera. FIG. 16A is an example extraction from a volunteer in accordance with the present technology. FIG. 16B is an example extraction from another volunteer in accordance with the present technology. FIG. 16C is an example extraction from another volunteer in accordance with the present technology. FIG. 16D is an example extraction from another volunteer in accordance with the present technology. FIG. 16E is an example extraction from another volunteer in accordance with the present technology.

To demonstrate the repeatability of the method, 5 volunteers were imaged resulting in FIG. 17A-17F. Though there are some individual differences, these participants still provide similar amplitude maps with 4 linear regions and phase maps with opposite phases in regions covering the common carotid arteries and the jugular veins. The CP and JVP waveforms from each subject (plots shown in FIGS. 16A-16E) were extracted and averaged from the videos under the guidance of phase maps. In doing so, the videos were recorded for 10 s from which CP and JVP waveforms were extracted according to the procedures described above. And then, the waveforms were aligned with their peak positions. Using the peak position as the mid-period time point, pulse waveforms of 5 consecutive periods were selected to calculate the averaged pulse waveforms, showing accordingly in the right of the figure. Though pulse waveforms from different subjects perform different shapes, right and left CP show clear systolic peaks and dicrotic notches. Besides, most JVP curves also include above-mentioned typical three positive and two negative waves. These extracted waveforms and features verified that the measurements are repeatable on different subjects.

Due to the symmetrical structures and functions in the human body, blood pulsations in the neck carotid arteries and jugular veins should appear highly bilateral symmetry in healthy normal subject. However, some cardiovascular malformations, for example unilateral carotid stenosis, would cause blood flows in the bilateral carotid arteries or jugular veins to appear asymmetry. In this case, the extracted CP and JVP waveforms from the method may be useful to provide a quick and cost-effective assessment of bilateral symmetry, which could potentially be used as a more straightforward biomarker to screen patients for stroke at high risk. To show the potential of the method for this application, in this study, a simple simulation experiment was demonstrated.

Figures 17A, 17B, 17C:
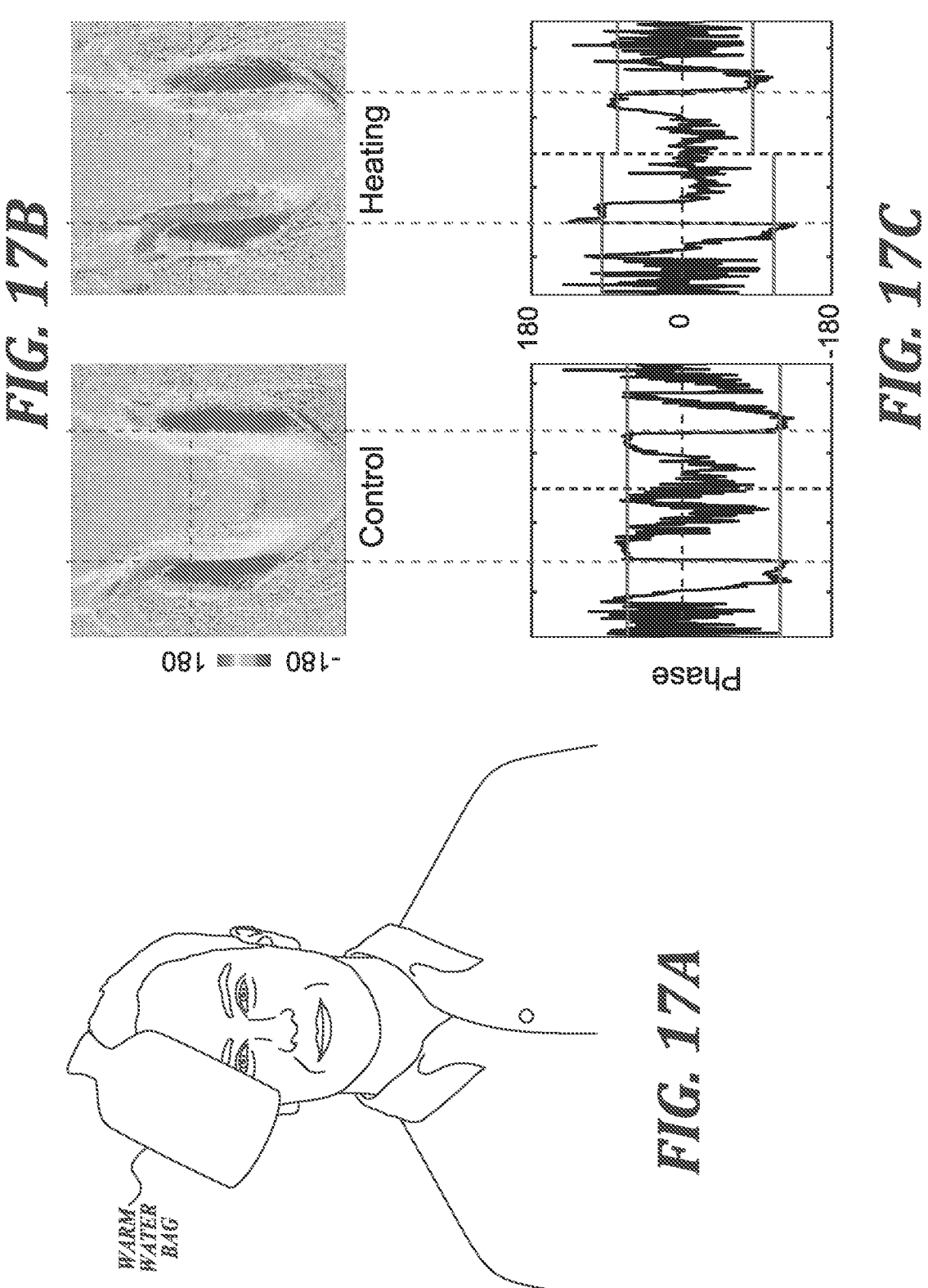
FIG. 17A is a schematic of warm-water pad stimulation on the hemisphere scalp tissue beds to reduce the blood flow resistance in the distal vascular tree, in accordance with the present technology.
FIG. 17B shows phase maps of the control group, in accordance with the present technology.
FIG. 17C shows phase profiles, in accordance with the present technology.
Figure 17D:
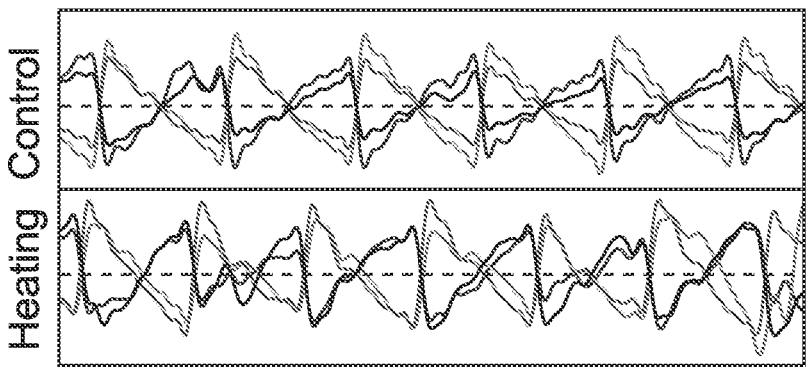
FIG. 17D shows extracted CP and JVP waveforms in stimulated and control groups.
Figure 17E:
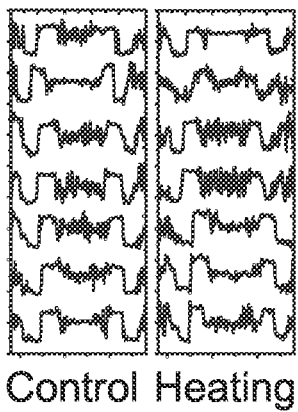
FIG. 17E shows phase profiles of control and heating groups, in accordance with the present technology.
Figure 17F:
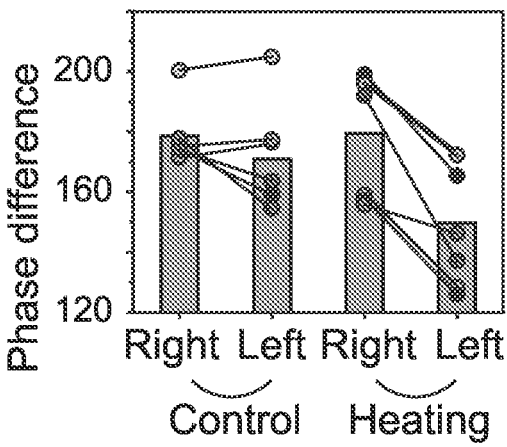
FIG. 17F is a quantification of averaged phase differences in multiple measurements, in accordance with the present technology.

FIGS. 17A-17F show the μMI method is feasible for assessing the symmetrical properties of the pulse waveforms in the bilateral arteries and veins in the neck regions. FIG. 17A is a schematic of warm-water pad stimulation on the hemisphere scalp tissue beds to reduce the blood flow resistance in the distal vascular tree, in accordance with the present technology. The application of the pad was on the right scalp which was away from the region of interest over the neck skin. FIG. 17B shows phase maps of the control group, in accordance with the present technology. Shown are the phase maps without warm stimulation (left image) and the heating group with warm stimulation on the right scalp (right image). FIG. 17C shows phase profiles, in accordance with the present technology. The phase profiles are at the location marked by horizontal dashed-lines in FIG. 17B, where the phase difference between CP and JVP is measured to be ~180° at both sides of the neck in the control group. However, in the stimulation group, the values are measured to be ~210° and ~170° at right and left sides, respectively. FIG. 17D shows extracted CP and JVP waveforms in stimulated and control groups. The darker lines represent the right jugular vein and the left jugular vein. The lighter lines represent the right common carotid artery and the left common carotid artery. FIG. 17E shows phase profiles of control and heating groups, in accordance with the present technology. The profiles were taken in seven measurement trials on volunteer 1, whose results have been presented in FIGS. 8B-8C, 9A-9D and 10A. FIG. 17F is a quantification of averaged phase differences in multiple measurements, in accordance with the present technology. The averaged phase differences are measured to be ~179±9°, ~171±16°, ~180±19° and ~150±19° in control right, control left, heating right and heating left groups, respectively. The connected spot's pair represents the bilateral phase differences in the same trial.

In the experiment, to induce the bilateral asymmetry in the pair of carotid arteries and jugular veins, the vascular resistance in the distal-end tissue beds were artificially modified. According to body tissue hemodynamics, the blood pulsation in the upstream artery would be reduced associated with reduced pulse transit time if the flow resistance at the distal-end tissue beds is reduced. To simulate the situation of reduced vascular resistance at the distal tissue beds, a warm-water pad was applied, covering the scalp of the right hemisphere in the volunteer (FIG. 17A). Previous studies proved that warm stimuli could cause local vasodilation, leading to the reduction of the regional vascular resistance. Therefore, theoretically, the application of the warm water pad on the right hemisphere of scalp would lead to the reduction of vascular resistance in the upstream right carotid artery, giving rise to a faster CP transmit time when compared to the carotid artery at the left side. It is then straightforward that the CP and JVP waves would become asymmetry. In the experiments, the video of a normal volunteer without the application of the water pad was recorded and treated as the control group. Then, the warm-water pad (measured at 42° C.) was applied on the scalp to cover the right hemisphere of head for 2 minutes (FIG. 17A). Afterwards, the video of neck skin of interest was collected and processed with the method described in the last section.

Compared with the phases of pulsatile neck motions, the imaging of amplitude suffers higher instability. Since the amplitude is sensitive to the change of signal intensities and other factors such as imaging angles and illumination uniformity. Therefore, the phase map was selected to conduct the analysis of bilateral symmetry. FIG. 17B shows the comparison of phase maps between control and stimulation groups from one representative subject. In the control group, the phase differences of CP- and JVP-related motions are almost equal on both sides of the neck. However, after warm-water stimulation, the right side shows increased phase difference. The same region of interest in both groups was selected and compared their profiles in FIG. 17C. The phase drop from CP to JVP shows obvious increase after stimulation, verified with visual observation. The phase difference was actually calculated between current JVP and next CP. Therefore, as shown in FIG. 17D, in a single heart cycle, warm stimulation would lead to a decreased phase difference around 17° between CP and JVP, which indicates a shortened pulse wave transit time around 40 ms from common carotid artery to jugular vein (for this subject). Stimulation on the right side of head leads to a vasodilation in the scalp tissue beds and thus decreased the resistance of homolateral blood vessels, eventually making the pulse wave transit time reduced. Multiple measurements on volunteer 1 under the same condition were taken and show the results illustrated in FIG. 17D-17F. In seven control groups, the averaged phase difference between JVP and CP were measured to be ~179±9° and ~171±16° at right and left sides, respectively. In seven heating groups, this value was measured to be ~180±19° and ~150±19°, respectively. From profiles and quantifications, the measurement of heat-induced bilateral asymmetrical phase was shown to be repeatable. These experimental results indicate the potential of the method to detect the bilateral asymmetry caused by cardiovascular abnormality.

Experimental results demonstrated the feasibility of this method to directly acquire, differentiate and analyze pulse waves in a non-contact and non-invasive manner. More importantly, the proposed approach is highly self-efficient in the data acquisition and processing, which can be independently operated without needed additional supports. For example, the amplitude and phase maps are self-derived from the video. In addition, more accurate CP and JVP waveforms are extracted from the recorded videos under the guidance of self-derived phase maps. Further, in the bilateral asymmetry assessment, the change in regional cardiovascular conditions can be also detected by self-referential measurements. Therefore, with a simple device setup without a need for an expert to operate, this technique is more easily accessible by public in their daily lives. This attribute would be extremely useful in the development of methods (either diagnostic or predictive) to prevent and early screen cardiovascular diseases, especially the carotid stenosis.

As discussed in FIGS. 16A-16E, motion-induced signals produce much stronger pulsation amplitudes. More importantly, comparing with former iPPG study which measures signals from distal capillary bed, μMI can directly access the information of carotid arteries and jugular veins, providing a more straightforward assessment for cardiovascular functions. Contact PPG approaches can also be devised to directly measure the heart pulse waveforms. However, jugular veins and common carotid arteries are closely located, which is easily to cause inaccurate positioning of the sensor probe, leading to a severe distortion of waveforms. An alternative would be to position the sensor probe under the guidance of other techniques, which would cause additional complexity and operation costs. Compared with these techniques, the μMI system and method provide more direct and accurate assessments with better usability.

There are still some limitations when using μMI to measure and analyze the CP and JVP waveforms from the neck region. Even though a 16-bit camera was employed in the current development, low light-tissue interaction efficiency and uncontrolled relative motions between the system and skin may impose a practical challenge in the data acquisition to guarantee the signal with sufficient signal quality. Besides, the information of motion amplitude had not been fully utilized. Compared with phase information, the amplitude derived from the method suffers instability due to the variation of imaging angles and individual conditions, which requires attention in the future endeavor of development aiming for wider applications.

A 16-bit camera was equipped in the system to record pulsatile motions with high fidelity. Lock-in amplification algorithm was used to derive the amplitude and phase of heart-cycle-related pulsatile motions. Guided by the pulse wave phase maps, CP and JVP waveforms were extracted from the acquired skin videos. Besides, based on the phase information, bilateral symmetry analysis was conducted on normal and unilateral stimulation on the distal-end tissue beds. Experimental results demonstrated that it is feasible to accurately extract CP and JVP waveforms and is capable of detecting bilateral differences between CP and/or CVP caused by stimulations on the scalp skin tissue beds. The proposed method revealed a possibility to realize these functions in a non-contact manner. Furthermore, since the measurement can be realized by simply recording a video of neck skin, it is easy to use without a need of expert to operate, which can be accessed by general public as an early screening tool for potential cardiovascular diseases.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of measuring blood oxygenation comprising:
acquiring one or more images of a portion of a body with an RGB camera;
converting RGB colors in the one or more images into a multispectral data imaging cube, wherein the multispectral data imaging cube comprises a red channel, a blue channel, and a green channel;
decoupling an oxygenated blood information and a deoxygenated blood information from the multispectral data imaging cube based on a first reflectance of the green channel and a second reflectance of the red channel, wherein decoupling the oxygenated blood information and the deoxygenated blood information comprises:
recording the first reflectance at the green channel and the second reflectance the red channel;
calculating a ratio of ratios from the first reflectance of the green channel and the second reflectance of the red channel, wherein the ratio of ratios is determined as:

$$R = \frac{\varepsilon_{Hb}(\lambda_1) + [\varepsilon_{HbO_2}(\lambda_1) - \varepsilon_{Hb}(\lambda_1)]SO_2}{\varepsilon_{Hb}(\lambda_2) + [\varepsilon_{HbO_2}(\lambda_2) - \varepsilon_{Hb}(\lambda_2)]SO_2}$$

where $\varepsilon_{Hb}$ is an extinction coefficient of the deoxygenated blood,
$\varepsilon_{HbO_2}$, is an extinction coefficient of the oxygenated blood,
$\lambda_1$ is a first wavelength;
$\lambda_2$ is a second wavelength, and
$SO_2$ is an oxygen saturation; and
measuring an average gray value of the red channel, green channel, and blue channel, wherein the average gray value is the sum of the gray values of all the pixels in the image divided by the number of pixels; and
determining a blood measurement based on the oxygenated blood information and the deoxygenated blood information.

2. The method of claim 1, wherein the multispectral data imaging cube represents spectral information at wavelengths of 450, 500, 550, 600, 650 and 700 nm.

3. The method of claim 1, wherein determining the blood measurement comprises applying a multiple linear regression algorithm to the oxygenated blood information and the deoxygenated blood information based on the calculated ratio of ratios and the averaged gray values of the red channel, green channel, and blue channel.

4. The method of claim 1, wherein the blood measurement is a set of blood pulsation amplitudes, a set of blood pulsation phases, or both.

5. The method of claim 4, wherein obtaining the set of blood pulsation amplitudes further comprises applying a window-based lock-in amplification to the oxygenated blood information and the deoxygenated blood information.

6. The method of claim 1, wherein the RGB camera is on a communication device.

7. The method of claim 6, wherein the communication device is a smartphone.

8. The method of claim 7, wherein the method further comprises displaying the blood measurement on a second communication device.

9. The method of claim 1, wherein the method further includes illuminating the portion of the body with a light source while acquiring the one or more images of the portion of the body.

10. The method of claim 9, wherein the light source is on communication device.

11. The method of claim 1, wherein the method further comprises calibrating the RGB camera with a Weiner estimation method and a color-checker.

12. The method of claim 1, wherein the method further comprises taking the oxygenated blood information and the deoxygenated blood information from a first region of a body and a second region of a body in an image.

13. The method of claim 1, wherein the one or more images comprise a video.

14. A method of measuring blood oxygenation comprising:

acquiring one or more images of a portion of a body with an RGB camera;

converting RGB colors in the one or more images into a multispectral data imaging cube, wherein the multispectral data imaging cube comprises a red channel, a blue channel, and a green channel;

decoupling an oxygenated blood information and a deoxygenated blood information from the multispectral data imaging cube based on a first reflectance of the green channel and a second reflectance of the red channel, and performing bilateral asymmetry analysis on the oxygenated blood information and the deoxygenated blood information of both the first region of the body and the second region of the body, wherein performing bilateral asymmetry analysis comprises:

generating a phase map and an amplitude map; and regionally extracting a first pulse signal from the first region of the body, and a second pulse signal from the second region of the body.

15. The method of claim 14, wherein generating the phase map and the amplitude map comprises:

filtering the first pulse signal and the second pulse signal with one or more heartbeat frequencies to generate a filtered signal; and using the filtered signal as a reference function to extract and amplify the first pulse signal and the second pulse signal with the same frequency as the filtered signal at each voxel of the image.

16. The method of claim 14, wherein the first region of the body comprises bilateral carotid regions of a neck and the second region of the body comprises bilateral jugular regions of a neck.

17. The method of claim 16, wherein the first pulse signal comprises a carotid pulse, and the second pulse signal comprises a jugular vein pulse.

18. A computer-implemented method comprising:

acquiring one or more images of a portion of a body with an RGB camera;

converting RGB colors in the one or more images into a multispectral data imaging cube, wherein the multispectral date imaging cube comprises a red channel, a blue channel, and a green channel;

decoupling an oxygenated blood information and a deoxygenated blood information from the multispectral data imaging cube based on a first reflectance of the green channel and a second reflectance of the red channel, wherein decoupling the oxygenated blood information and the deoxygenated blood information comprises:

recording the first reflectance at the green channel and the second reflectance the red channel;

calculating a ratio of ratios from the first reflectance of the green channel and the second reflectance of the red channel, wherein the ratio of ratios is determined as:

$$R = \frac{\varepsilon_{Hb}(\lambda_1) + \left[\varepsilon_{HbO_2}(\lambda_1) - \varepsilon_{Hb}(\lambda_1)\right]SO_2}{\varepsilon_{Hb}(\lambda_2) + \left[\varepsilon_{HbO_2}(\lambda_2) - \varepsilon_{Hb}(\lambda_2)\right]SO_2}$$

where $\varepsilon_{Hb}$ is an extinction coefficient of the deoxygenated blood, $\varepsilon_{HbO_2}$ is an extinction coefficient of the oxygenated blood, $\lambda_1$ is a first wavelength;

$\mu_2$ is a second wavelength, and $SO_2$ is an oxygen saturation; and measuring an average gray value of the red channel, green channel, and blue channel, wherein the average gray value is the sum of the gray values of all the pixels in the image divided by the number of pixels; and determining a blood measurement based on the oxygenated blood information and the deoxygenated blood information.

* * * * *